US011298433B2

(12) United States Patent
Lahoutte et al.

(10) Patent No.: US 11,298,433 B2
(45) Date of Patent: Apr. 12, 2022

(54) RADIOLABELLED ANTIBODY FRAGMENTS FOR USE IN TREATING CANCER

(71) Applicant: VRIJE UNIVERSITEIT BRUSSEL, Brussels (BE)

(72) Inventors: Tony Lahoutte, Ganshoren (BE); Matthias D'Huyvetter, Antwerp (BE); Jens De Vos, Strombeek-Bever (BE); Nick Devoogdt, Eppegem-Zemst (BE)

(73) Assignee: VRIJE UNIVERSITEIT BRUSSEL, Brussels (BE)

( * ) Notice: Subject to any disclaimer, the term of this patent is extended or adjusted under 35 U.S.C. 154(b) by 454 days.

(21) Appl. No.: 15/742,161

(22) PCT Filed: Jul. 15, 2016

(86) PCT No.: PCT/EP2016/066934
§ 371 (c)(1),
(2) Date: Jan. 5, 2018

(87) PCT Pub. No.: WO2017/013026
PCT Pub. Date: Jan. 26, 2017

(65) Prior Publication Data
US 2018/0200393 A1 Jul. 19, 2018

Related U.S. Application Data

(60) Provisional application No. 62/193,700, filed on Jul. 17, 2015.

(30) Foreign Application Priority Data

Jan. 29, 2016 (EP) ..................... 16153372

(51) Int. Cl.
*A61K 51/10* (2006.01)
*C07K 16/32* (2006.01)
*A61P 35/00* (2006.01)
*C07K 16/30* (2006.01)
*A61K 39/00* (2006.01)

(52) U.S. Cl.
CPC ...... *A61K 51/1096* (2013.01); *A61K 51/1051* (2013.01); *A61K 51/1093* (2013.01); *A61P 35/00* (2018.01); *C07K 16/30* (2013.01); *C07K 16/32* (2013.01); *A61K 2039/505* (2013.01); *A61K 2039/54* (2013.01); *C07K 2317/22* (2013.01); *C07K 2317/565* (2013.01); *C07K 2317/569* (2013.01)

(58) Field of Classification Search
None
See application file for complete search history.

(56) References Cited

U.S. PATENT DOCUMENTS 9,855,348 B2 * 1/2018 Devoogdt .......... A61K 51/1078
2005/0037421 A1 2/2005 Honda et al.
2009/0304590 A1 12/2009 Gill
2010/0209343 A1 * 8/2010 Bander .............. A61K 51/0482
424/1.49
2016/0030606 A1 2/2016 Devoogdt et al.
2018/0036442 A1 * 2/2018 Lahoutte ............ C07K 16/3015
2020/0276340 A1 9/2020 Lahoutte et al.

FOREIGN PATENT DOCUMENTS

| EP | 1 134 231 A1 | 9/2001 |
|---|---|---|
| EP | 1 433 793 A1 | 6/2004 |
| WO | 1994/004678 A1 | 3/1994 |
| WO | 1994/025591 A1 | 11/1994 |
| WO | 1995/004079 A1 | 2/1995 |
| WO | WO 1996/008565 A2 | 3/1996 |
| WO | 1996/034103 A1 | 10/1996 |
| WO | 1997/049805 A2 | 12/1997 |
| WO | 1999/037681 A2 | 7/1999 |
| WO | 2000/040968 A1 | 7/2000 |
| WO | 2000/043507 A1 | 7/2000 |
| WO | 2000/065057 A1 | 11/2000 |
| WO | 2001/021817 A1 | 3/2001 |
| WO | 2001/040310 A2 | 6/2001 |
| WO | 2001/044301 A1 | 6/2001 |
| WO | 2001/090190 A2 | 11/2001 |
| WO | 2002/048193 A2 | 6/2002 |
| WO | 2003/035694 A2 | 5/2003 |
| WO | 2003/050531 A2 | 6/2003 |
| WO | 2003/054016 A2 | 7/2003 |
| WO | 2003/055527 A2 | 7/2003 |

(Continued)

OTHER PUBLICATIONS

D'Huyvetter et al. (Expert Opinion on Drug Delivery, 11(12): 1939-1954, 2014).*
Kijanka et al. (Eur J Med Mol Imaging, 40: 1718-1729, 2013).*
Vaidyanathan et al. (Nuclear Medicine and Biology, 29: 1-11, 2002).*
Muruganandam et al. (2002) "Selection of phage-displayed llama single-domain antibodies that transmigrate across human blood-brain barrier endothelium," Faseb J. 16(2):240-2.
Muyldermans (2001) "Single domain camel antibodies: current status," Reviews in Molecular Biotechnology. 74(4):277-302.

(Continued)

*Primary Examiner* — Nelson B Moseley, II
(74) *Attorney, Agent, or Firm* — Lathrop GPM LLP; James H. Velema; Judith L. Stone-Hulslander

(57) ABSTRACT

Provided herein are methods, kits, and compositions for stratifying and treating subjects, e.g., subjects having cancer. In some examples, the methods involve use of a radiolabelled heavy chain variable domain derived from a heavy chain antibody ($V_{HH}$), or a functional fragment thereof, as both a screening agent and a treatment agent. In some examples, the $V_{HH}$, or a functional fragment thereof, that is radiolabelled with a radioisotope that is both a γ-emitter and β-emitter.

33 Claims, 3 Drawing Sheets
Specification includes a Sequence Listing.

(56) References Cited

FOREIGN PATENT DOCUMENTS

| WO | 2004/041862 A2 | 5/2004 | | |
|---|---|---|---|---|
| WO | 2004/041863 A2 | 5/2004 | | |
| WO | 2004/041865 A2 | 5/2004 | | |
| WO | 2004/041867 A2 | 5/2004 | | |
| WO | 2004/062551 A2 | 7/2004 | | |
| WO | WO 2009/068625 | * | 6/2009 | ............ C07K 16/46 |
| WO | WO 2010/004432 A1 | 1/2010 | | |
| WO | WO 2010/042815 A2 | 4/2010 | | |
| WO | WO 2011/051327 A1 | 5/2011 | | |
| WO | WO 2013/110531 A2 | 8/2013 | | |
| WO | WO 2014/140376 A1 | 9/2014 | | |
| WO | WO 2015/073746 A2 | 5/2015 | | |

OTHER PUBLICATIONS

Muyldermans et al. (1994) "Sequence and structure of VH domain from naturally occurring camel heavy chain immunoglobulins lacking light chains," Protein Eng. 7(9):1129-3.

Muyldermans et al. (1999) "Unique single-domain antigen binding fragments derived from naturally occurring camel heavy-chain antibodies," J. Mol. Recognit. 12(2):131-40.

Muyldermans et al. (2001) "Recognition of antigens by single-domain antibody fragments: the superfluous luxury of paired domains," Trends Biochem Sci. 26(4):230-5.

Nguyen et al. (1998) "The specific variable domain of camel heavy-chain antibodies is encoded in the germline," J. Mol. Biol. 275(3):413-8.

Nguyen et al. (1999) "Loss of splice consensus signal is responsible for the removal of the entire C(H)1 domain of the functional camel IGG2A heavy-chain antibodies," Mol. Immunol. 36(8):515-24.

Nguyen et al. (2000) "Camel heavy-chain antibodies: diverse germline V(H)H and specific mechanisms enlarge the antigen-binding repertoire," EMBO J. 19(5):921-30.

Nguyen et al. (2001) "Functional heavy-chain antibodies in Camelidae," Adv. Immunol. 79:261-96.

Nguyen et al. (2002) "Heavy-chain antibodies in Camelidae; a case of evolutionary innovation," Immunogenetics. 54(1):39-47.

Nguyen et al. (2003) "Heavy-chain only antibodies derived from dromedary are secreted and displayed by mouse B cells," Immunology. 109(1):93-101.

Nicaise et al. (2004) "Affinity transfer by CDR grafting on a nonimmunoglobulin scaffold," Protein Sci. 13(7):1882-91.

Omidfar et al. (2004) "Production and characterization of a new antibody specific for the mutant EGF receptor, EGFRvIII, in Camelus bactrianus," Tumour Biol 25(4):179-87.

Omidfar et al. (2004) "Production of a novel camel single-domain antibody specific for the type III mutant EGFR," Tumour Biol. 25(5-6):296-305.

Perez et al. (2001) "Thermal unfolding of a llama antibody fragment: a two-state reversible process," Biochemistry. 40(1):74-83.

Pleschberger et al. (2003) "Generation of a functional monomolecular protein lattice consisting of an s-layer fusion protein comprising the variable domain of a camel heavy chain antibody," Bioconjug. Chem. 14(2):440-8.

Pleschberger et al. (2004) "An S-layer heavy chain camel antibody fusion protein for generation of a nanopatterned sensing layer to detect the prostate-specific antigen by surface plasmon resonance technology," Bioconjug. Chem. 15(3):664-71.

Pruszynski et al. (Feb. 27, 2014) "Improved tumor targeting of anti-HER2 nanobody through N-succinimidyl 4-guanidinomethyl-3-iodobenzoate radiolabeling," J. Nucl. Med. 55(4):650-656.

Pruszynski et al. (Nov. 15, 2012) "Targeting breast carcinoma with radioiodinated anti-HER2 Nanobody," Nucl. Med. Biol. 40(1):52-9.

Renisio et al. (2002) "Solution structure and backbone dynamics of an antigen-free heavy chain variable domain (VHH) from Llama," Proteins. 47(4):546-55.

Riechmann aet al. (1999) "Single domain antibodies: comparison of camel VH and camelised human VH domains," J. Immunol. Methods. 231(1-2):25-38.

Saerens et al. (2004) "Single domain antibodies derived from dromedary lymph node and peripheral blood lymphocytes sensing conformational variants of prostate-specific antigen," J. Biol. Chem. 279(50):51965-72.

Sheriff et al. (1996) "Redefining the minimal antigen-binding fragment," Nat. Struct. Biol. 3(9):733-6.

Spinelli et al. (1996) "The crystal structure of a llama heavy chain variable domain," Nat. Struct. Biol. 3(9):752-7.

Spinelli et al. (2000) "Camelid heavy-chain variable domains provide efficient combining sites to haptens," Biochemistry. 39(6):1217-22.

Spinelli et al. (2001) "Lateral recognition of a dye hapten by a llama VHH domain," J. Mol. Biol. 311(1):123-9.

Spinelli et al. (2004) "Domain swapping of a llama VHH domain builds a crystal-wide beta-sheet structure," FEBS Lett. 564(1-2):35-40.

Stijlemans et al. (2004) "Efficient targeting of conserved cryptic epitopes of infectious agents by single domain antibodies. African trypanosomes as paradigm," J Biol. Chem. 279(2):1256-61.

Su et al. (2002) "Adaptive evolution of variable region genes encoding an unusual type of immunoglobulin in camelids," Mol. Biol. Evol. 19(3):205-15.

Szynol et al. (2004) "Bactericidal effects of a fusion protein of llama heavy-chain antibodies coupled to glucose oxidase on oral bacteria," Antimicrob. Agents Chemother. 48(9):3390-5.

Thomassen et al. (2002) "Large-scale production of VHH antibody fragments by *Saccharomyces cerevisiae*," Enzyme Microb. Technol. 30:273-8.

Transue et al. (1998) "Camel single-domain antibody inhibits enzyme by mimicking carbohydrate substrate," Proteins. 32(4):515-22.

Van Der Linden et al. (1999) "Comparison of physical chemical properties of llama VHH antibody fragments and mouse monoclonal antibodies," Biochim. Biophys. Acta. 1431(1):37-46.

Van Der Linden et al. (2000) "Improved production and function of llama heavy chain antibody fragments by molecular evolution," J. Biotechnol. 80(3):261-70.

Van Der Linden et al. (2000) "Induction of immune responses and molecular cloning of the heavy chain antibody repertoire of Lama glama," J. Immunol. Methods. 240(1-2):185-95.

Van Der Vaart (2002) "Expression of VHH antibody fragments in *Saccharomyces cerevisiae*," Methods Mol. Biol. 178:359-66.

Van Koningsbruggen et al. (2003) "Llama-derived phage display antibodies in the dissection of the human disease oculopharyngeal muscular dystrophy," J. Immunol. Methods. 279(1-2):149-61.

Verheesen et al. (2003) "Beneficial properties of single-domain antibody fragments for application in immunoaffinity purification and immuno-perfusion chromatography," Biochim. Biophys. Acta. 1624(1-3):21-8.

Vranken et al. (2002) "Solution structure of a llama single-domain antibody with hydrophobic residues typical of the VH/VL interface," Biochemistry. 41(27):8570-9.

Vu et al. (1997) "Comparison of llama VH sequences from conventional and heavy chain antibodies," Mol. Immunol. 34(16-17):1121-31.

Woolven et al. (1999) "The structure of the llama heavy chain constant genes reveals a mechanism for heavy-chain antibody formation," Immunogenetics. 50(1-2):98-101.

Yau et al. (2003) "Selection of hapten-specific single-domain antibodies from a non-immunized llama ribosome display library," J. Immunol. Methods. 281(1-2):161-75.

Yau et al. (2005) "Affinity maturation of a V(H)H by mutational hotspot randomization," J. Immunol. Methods. 297(1-2):213-24.

Zarebski et al. (2005) "Llama single domain antibodies as a tool for molecular mimicry," J. Mol. Biol. 349(4):814-24.

Zhang et al. (2004) "Pentamerization of single-domain antibodies from phage libraries: a novel strategy for the rapid generation of high-avidity antibody reagents," J. Mol. Biol. 335(1):49-56.

International Search Report with Written Opinion corresponding to International Patent Application No. PCT/EP2016/066934, dated Oct. 27, 2016.

Atarhouch et al. (1997) "cDNA sequence coding for the constant region of the dromedary g3 heavy-chain antibody," Journal of Camel Practice and Research. 4:177-182.

(56) References Cited

OTHER PUBLICATIONS

Bond et al. (2003) "Contributions of CDR3 to V H H domain stability and the design of monobody scaffolds for naive antibody libraries," J. Mol. Biol. 332(3):643-55.
Bond et al. (2005) "A structure-based database of antibody variable domain diversity," J. Mol. Biol. 348(3):699-709.
Choi et al. (Aug. 1, 2014) "N-Succinimidyl guanidinomethyl iodobenzoate protein radiohalogenation agents: Influence of isomeric substitution on radiolabeling and target cell residualization," Nucl. Med. Biol. 41(10):1802-812.
Chothia et al. (1989) "Conformations of immunoglobulin hypervariable regions," Nature. 342:877-883.
Conrath et al. (2001) "Beta-lactamase inhibitors derived from single-domain antibody fragments elicited in the camelidae," Antimicrob. Agents Chemother. 45(10):2807-12.
Conrath et al. (2001) "Camel single-domain antibodies as modular building units in bispecific and bivalent antibody constructs," J. Biol. Chem. 276(10):7346-50.
Conrath et al. (2003) "Emergence and evolution of functional heavy-chain antibodies in Camelidae," Dev. Comp. Immunol. 27(2):87-103.
Cortez-Retamozo et al. (2002) "Efficient tumor targeting by single-domain antibody fragments of camels," Int. J. Cancer. 98(3):456-462.
Cortez-Retamozo et al. (2004) "Efficient cancer therapy with a nanobody-based conjugate," Cancer Res. 64(8):2853-7.
Davies et al. (1994) "'Camelising' human antibody fragments: NMR studies on VH domains," FEBS Lett. 339(3):285-90.
Davies et al. (1995) "Antibody VH domains as small recognition units," Biotechnology (NY). 13(5):475-9.
Davies et al. (1996) "Single antibody domains as small recognition units: design and in vitro antigen selection of camelized, human VH domains with improved protein stability," Protein Eng. 9(6):531-7.
De Genst et al. (2002) "Kinetic and affinity predictions of a protein-protein interaction using multivariate experimental design," J. Biol. Chem. 277(33):29897-907.
De Genst et al. (2004) "Chemical basis for the affinity maturation of a camel single domain antibody," J. Biol. Chem. 279(51):53593-601.
De Genst et al. (2005) "Strong in vivo maturation compensates for structurally restricted H3 loops in antibody repertoires," J. Biol. Chem. 280(14):14114-21.
Decanniere et al. (1999) "A single-domain antibody fragment in complex with RNase A: non-canonical loop structures and nanomolar affinity using two CDR loops," Structure Fold. Des. 7(4):361-70.
Decanniere et al. (2000) "Canonical antigen-binding loop structures in immunoglobulins: more structures, more canonical classes?" J. Mol. Biol. 300(1):83-91.
Decanniere et al. (2001) "Degenerate interfaces in antigen-antibody complexes," J. Mol. Biol. 313(3):473-8.
Dekker et al. (2003) "Intracellularly expressed single-domain antibody against p15 matrix protein prevents the production of porcine retroviruses," J. Virol. 77(22):12132-9.
Desmyter et al. (1996) "Crystal structure of a camel single-domain VH antibody fragment in complex with lysozyme," Nat. Struct. Biol. 3(9):803-11.
Desmyter et al. (2001) "Antigen specificity and high affinity binding provided by one single loop of a camel single-domain antibody," J. Biol. Chem. 276(28):26285-90.
Desmyter et al. (2002) "Three camelid VHH domains in complex with porcine pancreatic alpha-amylase. Inhibition and versatility of binding topology," J. Biol. Chem. 277(26):23645-50.
D'Huyvetter et al. (2012) "Development of 177Lu-nanobodies for radioimmunotherapy of HER2-positive breast cancer: evaluation of different bifunctional chelators," Contrast. Media Mol. Imaging. 7(2):254-64.
D'Huyvetter et al. (Apr. 25, 2014) "Targeted radionuclide therapy with A 177Lu-labeled anti-HER2 nanobody," Theranostics. 4(7):708-20.
Dolk et al. (2005) "Induced refolding of a temperature denatured llama heavy-chain antibody fragment by its antigen," Proteins. 59(3):555-64.
Dolk et al. (2005) "Isolation of llama antibody fragments for prevention of dandruff by phage display in shampoo," Appl. Environ. Microbiol. 71(1):442-50.
Dumoulin et al. (2002) "Single-domain antibody fragments with high conformational stability," Protein Sci. 11(3):500-15.
Dumoulin et al. (2003) "A camelid antibody fragment inhibits the formation of amyloid fibrils by human lysozyme," Nature. 424(6950):783-8.
Dumoulin et al. (2005) "Reduced global cooperativity is a common feature underlying the amyloidogenicity of pathogenic lysozyme mutations," J. Mol. Biol. 346(3):773-88.
Ewert et al. (2002) "Biophysical properties of camelid V(HH) domains compared to those of human V(H)3 domains," Biochemistry 41(11):3628-36.
Ferrat et al. (2002) "A peptide mimic of an antigenic loop of alpha-human chorionic gonadotropin hormone: solution structure and interaction with a llama V(HH) domain," Biochem. J. 366(Pt 2):415-22.
Frenken et al. (1998) "Recent advances in the large-scale production of antibody fragments using lower eukaryotic microorganisms," Res Immunol. 149(6):589-99.
Frenken et al. (2000) "Isolation of antigen specific llama VHH antibody fragments and their high level secretion by *Saccharomyces cerevisiae*," J. Biotechnol. 78(1):11-21.
Ghahroudi et al. (1997) "Selection and identification of single domain antibody fragments from camel heavy-chain antibodies," FEBS Lett. 414(3):521-6.
Gharoudi et al. (1995) "Identification of soluble, stable camel VH antibody fragments expressed in *E. coli*, with specificity and neutralizing activity for tetanus toxoid," Mededelingen Faculteit Landbouwkundige en Toegepaste Biologische Wetenschappen Universiteit Gent. 60(4A-B):2097-2100.
Hamers-Casterman et al. (1993) "Naturally occurring antibodies devoid of light chains," Nature. 363(6428):446-8.
Harmsen et al. (2000) "Llama heavy-chain V regions consist of at least four distinct subfamilies revealing novel sequence features," Mol. Immunol. 37(10):579-90.
Harmsen et al. (2002) "Stimulation of chymosin secretion by simultaneous expression with chymosin-binding llama single-domain antibody fragments in yeast," Appl. Microbiol. Biotechnol. 60(4):449-54.
Hoogenboom (2005) "Selecting and screening recombinant antibody libraries," Nature Biotechnology. 23(9):1105-1116.
Huang et al. (2005) "Protein studies in dysferlinopathy patients using llama-derived antibody fragments selected by phage display," Eur. J. Hum. Genet. 13(6):721-30.
Jobling et al. (2003) "Immunomodulation of enzyme function in plants by single-domain antibody fragments," Nat. Biotechnol. 21(1):77-80.
Joosten et al. (2003) "The production of antibody fragments and antibody fusion proteins by yeasts and filamentous fungi," Microb. Cell Fact. 2(1):1. pp. 1-15.
Joosten et al. (2005) "Expression and production of llama variable heavy-chain antibody fragments (V(HH)s) by *Aspergillus awamori*," Appl. Microbiol. Biotechnol. 66(4):384-92.
Lah et al. (2003) "Recognition of the intrinsically flexible addiction antidote MazE by a dromedary single domain antibody fragment. Structure, thermodynamics of binding, stability, and influence on interactions with DNA," J. Biol. Chem. 278(16):14101-11.
Lauwereys et al. (1998) "Potent enzyme inhibitors derived from dromedary heavy-chain antibodies," EMBO J. 17(13):3512-20.
Ledeboer et al. (2002) "Preventing phage lysis of Lactococcus lactis in cheese production using a neutralizing heavy-chain antibody fragment from llama," J. Dairy Sci. 85(6):1376-82.
Li et al. (2003) "A soft docking algorithm for predicting the structure of antibody-antigen complexes," Proteins. 52(1):47-50.
Loris et al. (2003) "Crystal structure of the intrinsically flexible addiction antidote MazE," Biol. Chem. 278(30):28252-7.

(56) References Cited

OTHER PUBLICATIONS

Meddeb-Mouelhi et al. (2003) "Immunized camel sera and derived immunoglobulin subclasses neutralizing Androctonus australis hector scorpion toxins," Toxicon. 42(7):785-91.
U.S. Appl. No. 14/802,077, filed Jul. 17, 2015, 2016/0030606, Feb. 4, 2016, U.S. Pat. No. 9,855,348, Jan. 2, 2018, Nick Devoogdt.
U.S. Appl. No. 15/742,161, filed Jan. 5, 2018, 2018/0200393, Jul. 19, 2018, Tony Lahoutte.
U.S. Appl. No. 15/329,860, filed Nov. 1, 2017, 2018/0036442, Feb. 8, 2018, Tony Lahoutte.
U.S. Appl. No. 16/827,032, filed Mar. 23, 2020, Tony Lahoutte.
Byers, "What Can Randomized Controlled Trials Tell Us About Nutrition and Cancer Prevention?", CA Canver Journ, Nov./Dec. 1999, vol. 49, No. 6, pp. 353-361.
Colman, "Effects of amino acid sequence changes on antiboby-antigen interactions", Research in Immunology, 1994, vol. 145, pp. 33-36.
Cortez-Retamozo et al., "$^{99m}$Tc-Labeled nanobodies: a new type of targeted probes for imaging antigen expression," Current Radiopharmaceuticals, 2008, 1(1):37-41.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody", Journal of Immunology, 2002, vol. 169, pp. 3076-3084.
D'Huyvetter et al., "Targeted Radionuclide Therapy with A 177Lu-labeled Anti-HER2 Nanobody," Theranostics, 2004, 4(7):708-720.
D'Huyvetter et al., "Development of 177Lu-nanobodies for radioimmunotherapy of HER2-positive breast cancer: evaluation of different bifunctional chelators," Contrast Media and Molecular Imaging, 2012, 7:254-264.
D'Huyvetter et al., "Nanobody-based Targeted Radiotherapy for Cancer Treatment," In; The European Cooperation in the field of Science and Technology Meeting 2013: Theragnostics Imaging and Therapy: An Action to Develop Novel Nanosized Systems for Imaging-Guided Drug Delivery. Action TD1004, Sep. 1-3, 2013, Athens, Greece—Meeting abstract only.
D'Huyvetter, "Evaluation of bivalent antiHER2 Nanobody constructs for improved cellular retention and in vivo tumor targeting," Abstract for Poster Presentation No. P529 Presented In; The World Molecular Imaging Congress, 2012, Dublin, Ireland. 2 pgs.
D'Huyvetter, "Evaluation of bivalent antiHER2 Nanobody constructs for improved cellular retention and in vivo tumor targeting," Poster for Poster Presentation No. P529 Presented In; The World Molecular Imaging Congress, 2012, Dublin, Ireland. 1 pg.
Eyer et al., "Single-domain antibody fragments derived from heavy-chain antibodies: a review," Veterinarni Medicina, Sep. 2012, 57:439-513.
Gainkam et al., "Comparison of the biodistribution and tumor targeting of two 99mTc-labeled anti-EGFR nanobodies in mice, using pinhole SPECT/micro-CT," J. Nucl. Med., 2008, 49(5):788-795.
Gainkam et al., "Correlation Between Epidermal Growth Factor Receptor-Specific Nanobody Uptake and Tumor Burden: A Tool for Noninvasive Monitoring of Tumor Response to Therapy," Mol. Imaging Biol., 2010 13(5):940-948.
Gibbs, "Nanobodies", Scientific American, 2005, vol. 293, No. 2, pp. 67-71.
Granziero et al., "Adoptive immunotherapy prevents prostate cancer in a transgenic animal model", European Journal of Immunology, 1999, vol. 29, pp. 1127-1138.
Huang et al., "SPECT imaging with $^{99m}$Tc-labeled EGFR-specific nanobody for in vivo monitoring of EGFR expression," Molecular Imaging and Biology, 2008, 10(3):167-175.
International Preliminary Report on Patentability corresponding to International Patent Application No. PCT/EP2015/066430, completed Jun. 22, 2016.
International Search Report with Written Opinion corresponding to International Patent Application No. PCT/EP2015/066430, dated Nov. 10, 2015.

MacCallum et al., "Antibody-antigen Interactions: Contact Analysis and Binding Site Topography", Journal of Molecular Biology, 1996, vol. 262, pp. 732-745.
Massa, "Site-specific coupling of Nanobodies® directed against the membrane protein HER2 for non-invasive, multi-modal imaging in pre-clinical cancer models," Master's Thesis for the fulfillment of the degree of Master of Bioscience Engineering: Cell and Gene Biotechnology—Medical Biotechnology. Vrije Universiteit Brussel. Brussels, Belgium, 2011, with English machine translation.
Oliveira et al., "Targeting Tumors with Nanobodies for Cancer Imaging and Therapy," J. Controlled Release, 2013, 172(3):607-617.
Pruszynski et al., "Improved Tumor Targeting of Anti-HER2 Nanobody Through N-Succinimidyl 4-Guanidinomethyl-3-Iodobenzoate Radiolabeling," The Journal of Nuclear Medicine, 2014, 55(4):650-656.
Pruszynski et al., "Targeting breast carcinoma with radioiodinated anti-HER2 Nanobody", Nuclear Medicine and Biology, 2013, vol. 40, pp. 52-59.
Rudikoff et al., "Single amino acid substitution altering antigen-binding specificity", Proc. Natl. Acad. Sci. USA, Mar. 1982, vol. 79, No. 6, pp. 1979-1983.
Schoonooghe et al., "Novel applications of nanobodies for in vivo bio-imaging of inflamed tissues in inflammatory diseases and cancer," Immunobiology, 2012, 217(12):1266-1272.
Search Report with Search Opinion corresponding to European Patent Application No. 14178943.8, dated Apr. 28, 2015.
Siontorou, "Nanobodies as novel agents for disease diagnosis and therapy," International Journal of Nanomedicine, Nov. 2013, 8:4215-4227.
Stabin et al., "OLINDA/EXM: the second-generation personal computer software for internal dose assessment in nuclear medicine," J. Nucl. Med., 2005, 46:1023-1027.
Szpakowska, "Selection of HER2-Specific Internalising Nanobodies," Master's Thesis for the partial fulfillment of the degree of Master of Biomolecular Sciences, 2010, Vrije Universiteit Brussel. Brussels, Belgium.
Tijink et al., "Improved tumor targeting of anti-epidermal growth factor receptor Nanobodies through albumin binding: taking advantage of modular Nanobody technology," Molecular Cancer Therapeutics, 2008, 7(8):2288-2297.
Van Gassen, "Characterization of anti-HER2 Nanobodies for non-invasive imaging of HER2 Positive Tumors," Master's Thesis for the fulfillment of the degree of Master of Biology: Genetics, Cellular and Developmental Biology. Vrije Universiteit Brussel. Brussels, Belgium, 2009, with English machine translation.
Vaneycken et al., "Preclinical screening of anti-HER2 nanobodies for molecular imaging of breast cancer", The FASEB Journal—Research Communication, Jul. 2011, vol. 25, pp. 2433-2446.
Vosjan et al., "Facile labelling of an anti-epidermal growth factor receptor Nanobody with 68Ga via a novel bifunctional desferal chelate for immuno-PET," Eur. J. Nucl. Med. Mol. Imaging, 2011, 38(4):753-763.
Vosjan et al., "Nanobodies Targeting the Hepatocyte Growth Factor: Potential New Drugs for Molecular Cancer Therapy," Molecular Cancer Therapeutics, 2012, 11(4):1017-1025.
Xavier et al., "Synthesis, Preclinical Validation, Dosimetry, and Toxicity of 68Ga-NOTA-Anti-HER2 Nanobodies for iPET Imaging of HER2 Receptor Expression in Cancer," J. Nucl. Med., 2013, 54(5):776-784.
Xavier et al., "Anti-HER2 Nanobodies: Novel Theranostic Tools," In; The Abstracts of 7th World Molecular Imaging Congress Scientific Session 08: SS 46, Seoul, South Korea, Mol Imaging Biol, 2015, vol. 17, Suppl. 1, S1-S1352.
Chakravarty et al., "Nanobody: The "Magic Bullet" for Molecular Imaging?", Theranostics, 2014, 4(4): 386-398.
Debie et al., "Effect of Dye and Conjugation Chemistry on the Biodistribution Profile of Near-Infrared-Labeled Nanobodies as Tracers for Image-Guided Surgery", Mol Pharm., Apr. 3, 2017,14(4): 1145-1153.
Devoogdt et al., "Molecular Imaging Using Nanobodies: A Case Study", Methods in Molecular Biology, 2012, vol. 911.

(56) References Cited

OTHER PUBLICATIONS

D'Huyvetter et al., "Radiolabeled nanobodies as theranostic tools in targeted radionuclide therapy of cancer", Expert Opin Drug Deliv., Dec. 2014, 11(12): 1939-1954.

D'Huyvetter et al., "$^{131}$I-labeled Anti-HER2 Camelid sdAb as a Theranostic Tool in Cancer Treatment", Clin Cancer Res., Nov. 1, 2017, 23(21): 6616-6628.

D'Huyvetter, et al., Expert Opinion on Drug Delivery, 2014, vol. 11, No. 12, pp. 1939-1954.

Goldstein et al., "Developments in single photon emission computed tomography and PET-based HER2 molecular imaging for breast cancer", Expert Rev Anticancer Ther., Mar. 2013, 13(3): 359-373.

International Preliminary Report on Patentability corresponding to International Patent Application No. PCT/EP2015/067424, dated Jan. 31, 2017.

International Preliminary Report on Patentability corresponding to International Patent Application No. PCT/EP2016/066934, dated Jan. 23, 2018.

International Search Report with Written Opinion corresponding to International Patent Application No. PCT/EP2015/067424, dated Nov. 11, 2015.

Keyaerts et al., "Phase I Study of 68Ga-HER2-Nanobody for PET/CT Assessment of HER2 Expression in Breast Carcinoma", The Journal of Nuclear Medicine, vol. 57, No. 1, Jan. 2016, pp. 27-33.

Kijankka et al., "Rapid optical imaging of human breast tumour xenografts using anti-HER2 VHHs site-directly conjugated to IRDye 800CW for image-guided surgery", European Journal of Molecular Imaging, 2013, vol. 40, pp. 1718-1729.

Massa et al., "Site-Specific Labeling of Cysteine-Tagged Camelid Single-Domain Antibody-Fragments for Use in Molecular Imaging", Bioconjg Chem., May 21, 2014, 25(5): 979-988.

Meng et al., "Molecular Imaging Probes for Diagnosis and Therapy Evaluation of Breast Cancer", Int'l Journal of Biomedical Imaging, 2013, Article ID 230487, pp. 1-14.

Muyldermans et al., "Identification of Camel-Derived Antibodies for Screening Breast Cancer Patients", 2012, pp. 29-31.

Patris et al., "Nanoimmunoassay onto a screen printed electrode for HER2 breast cancer biomarker determination", Talenta, Dec. 2014, 130: 164-170.

Vaidyanathan et al., "Improved xenograft targeting of tumor-specific anti-epidermal growth factor receptor variant III antibody labeled using N-succinimidyl 4-guanidinomethyl-3-iodobenzoate", Nuclear Medicine and Biology, 2002, vol. 29, pp. 1-11.

Vaneycken et al., "Immuno-imaging using nanobodies", Curr Opin in Bio., 2011, 22(6): 877-881.

Vaneycken et al., "Synthesis and first in vivo evaluation of 18F-anti-HER2-Nanobodies: a new probe for PET imaging of HER2 expression in breast cancer", Journal of Nuclear Medicine, Apr. 2011,52(4): 664.

Wang et al., "Antibody-Based Imaging of HER-2: Moving into the Clinic", Current Molecular Medicine, Dec. 2013, 13(10): 1523-1537.

U.S. Appl. No. 14/802,077 filed Jul. 17, 2015, U.S. Publication No. 2016/0030606 filed Feb. 4, 2016, U.S. Pat. No. 9,855,348 filed Jan. 2, 2018, Nick Devoogdt.

U.S. Appl. No. 15/742,161 filed Jan. 5, 2018, U.S. Publication No. 2018/0200393, filed Jul. 19, 2018, Tony Lahoutte.

U.S. Appl. No. 15/329,860 filed Jan. 5, 2018, U.S. Publication No. 2018/0036442 filed Feb. 8, 2018, Tony Lahoutte.

U.S. Appl. No. 16/827,032 filed Mar. 23, 2020, U.S. Publication No. 2020/0276340 filed Sep. 3, 2020, Tony Lahoutte.

\* cited by examiner

RADIOLABELLED ANTIBODY FRAGMENTS FOR USE IN TREATING CANCER

RELATED APPLICATIONS

This application is a 35 U.S.C. § 371 filing of International Patent Application No. PCT/EP2016/066934, filed Jul. 15, 2016, which claims priority to U.S. Provisional Patent Application Ser. No. 62/193,700, filed Jul. 17, 2015, and European Patent Application No. 16153372.4, filed Jan. 29, 2016, the entire disclosures of which are hereby incorporated herein by reference in their entirety.

FIELD OF THE INVENTION

The present disclosure relates to the field of radiolabelled antibody fragments and uses thereof for stratification of subjects for treatment. In particular, the present disclosure relates to radiolabelled antibody fragments for use in the stratification of subjects for treatment of cancer.

BACKGROUND

Successful treatment of cancer remains difficult, in part due to the heterogeneity of cancer in different individuals. There remains a need to develop methods for selecting subjects that are likely to respond to a particular cancer treatment in order to improve the likelihood of successful treatment.

SUMMARY OF THE INVENTION

In some aspects, the disclosure provides methods, kits, and compositions for selecting a subject for treatment and subsequently treating the selected subject utilizing a screening dose and a therapeutic dose of the same radiolabelled antibody fragment, e.g., a heavy chain variable domain derived from a heavy chain antibody (also referred to herein as a $V_{HH}$). In some embodiments, the screening dose is used to determine that the radiolabelled antibody fragment is capable of binding to a cancer cell or solid tumor in the subject, thereby indicating that the subject is a candidate for treatment with the same radiolabelled antibody fragment at a therapeutic dose. Without wishing to be bound by theory, it is believed that use of the same radiolabelled antibody fragment as both the screening agent and the therapeutic agent will increase the likelihood that the subject selected for treatment using the screening agent will respond to the therapeutic agent.

In some aspects, the disclosure provides a method of treating cancer, the method comprising:
selecting a subject having cancer for treatment on the basis of detection in the subject of a screening dose of a radiolabelled, heavy chain variable domain derived from a heavy chain antibody ($V_{HH}$), or a functional fragment thereof, which specifically binds to a target protein that is present on a cancer cell or solid tumor; and
administering to the subject a therapeutic dose of the radiolabelled $V_{HH}$, or functional fragment thereof,
wherein the $V_{HH}$, or functional fragment thereof, is radiolabelled with a radioisotope that is both a γ-emitter and β-emitter. In some embodiments, the method further comprises:
administering the screening dose to the subject and detecting the presence of the radiolabelled $V_{HH}$, or functional fragment thereof, at a tumor site in the subject prior to selecting the subject.

In some embodiments of any one of the methods described herein, detecting the presence of the radiolabelled $V_{HH}$, or functional fragment thereof, comprises imaging the subject. In some embodiments, the imaging is gamma camera imaging such as planar gamma camera imaging, single photon emission computed tomography or positron emission tomography, optionally combined with a non-nuclear imaging technique such as X-ray imaging, computed tomography and/or magnetic resonance imaging.

In some embodiments of any one of the methods described herein, the radioisotope is Iodine-131, Lutetium-177, Yttrium-90, Copper-67, Rhenium-186, or Rhenium-188.

In some embodiments of any one of the methods described herein, the radioisotope is attached to the $V_{HH}$, or functional fragment thereof, via a linker.

In some embodiments of any one of the methods described herein, the $V_{HH}$, or functional fragment thereof, is radiolabelled with Iodine-131 using N-succinimidyl-4-guanidinomethyl-3-[I-131]iodobenzbate ([I-131]-SGMIB) or a suitable derivative or variant thereof.

In some embodiments of any one of the methods described herein, the screening dose is between 37 MBq and 370 MBq and the therapeutic dose is between 370 MBq and 18500 MBq.

In some embodiments of any one of the methods described herein, the radiolabelled $V_{HH}$, or functional fragment thereof, specifically binds to HER2. In some embodiments of any one of the methods described herein, the radiolabelled $V_{HH}$, or functional fragment thereof, does not compete with the monoclonal antibody Trastuzumab (Herceptin®) or the monoclonal antibody Pertuzumab (Perjeta®) for binding to HER2, as determined using a competition assay.

In some embodiments of any one of the methods described herein, the radiolabelled $V_{HH}$, or a functional fragment thereof, comprises one of the CDR combinations chosen from the group comprising:
a CDR1 region having SEQ ID NO:1, a CDR2 region having SEQ ID NO:2, and a CDR3 region having SEQ ID NO:3, and
a CDR1 region having SEQ ID NO:4, a CDR2 region having SEQ ID NO:5, and a CDR3 region having SEQ ID NO:6.

In some embodiments of any one of the methods described herein, the radiolabelled $V_{HH}$, or the functional fragment thereof, has at least 80% amino acid identity with at least one of the amino acid sequences of SEQ ID NOs:7 and 8. In some embodiments of any one of the methods described herein, the radiolabelled $V_{HH}$, or the functional fragment thereof, is identical with at least one of the amino acid sequences of SEQ ID NOs: 7 and 8.

In some embodiments of any one of the methods described herein, the screening dose and the therapeutic dose of the radiolabelled $V_{HH}$, or functional fragment thereof, are each independently administered to the subject intravenously, intraperitoneally, or intrathecally.

In some embodiments of any one of the methods described herein, the radiolabelled $V_{HH}$, or functional fragment thereof, is present in a monovalent format. In some embodiments of any one of the methods described herein, the radiolabelled $V_{HH}$, or functional fragment thereof, is devoid of a cysteine-containing tag, preferably a GGC-tag. In some embodiments of any one of the methods described herein, the radiolabelled $V_{HH}$, or functional fragment thereof, is non-lifetime extended. In some embodiments of any one of the methods described herein, the radiolabelled $V_{HH}$, or functional fragment thereof, is untagged.

In some embodiments of any one of the methods described herein, the cancer is a solid tumor. In some embodiments of any one of the methods described herein, the cancer is a hematological cancer. In some embodiments of any one of the methods described herein, the cancer is breast cancer, ovarian cancer, gastric cancer, multiple myeloma, or lymphoma.

Other aspects of the disclosure relate to a kit, comprising:
a screening dose of a radiolabelled $V_{HH}$, or functional fragment thereof, which specifically binds to a target protein that is present on a cancer cell or solid tumor, and
a therapeutic dose of the radiolabelled $V_{HH}$, or functional fragment thereof,
wherein the $V_{HH}$, or functional fragment thereof, is radiolabelled with a radioisotope that is both a γ-emitter and β-emitter.

In some embodiments of any one of the kits described herein, the radioisotope is Iodine-131, Lutetium-177, Yttrium-90, Copper-67, Rhenium-186, or Rhenium-188.

In some embodiments of any one of the kits described herein, the radioisotope is attached to the $V_{HH}$, or functional fragment thereof, via a linker.

In some embodiments of any one of the kits described herein, the $V_{HH}$, or functional fragment thereof, is radiolabelled with Iodine-131 using N-succinimidyl-4-guanidinomethyl-3-[I-131]iodobenzbate ([I-131]-SGMIB) or a suitable derivative or variant thereof.

In some embodiments of any one of the kits described herein, the screening dose is between 37 MBq and 370 MBq and the therapeutic dose is between 370 MBq and 18500 MBq.

In some embodiments of any one of the kits described herein, the radiolabelled $V_{HH}$, or functional fragment thereof, specifically binds to HER2. In some embodiments of any one of the kits described herein, the radiolabelled $V_{HH}$, or functional fragment thereof, does not compete with the monoclonal antibody Trastuzumab (Herceptin®) or the monoclonal antibody Pertuzumab (Perjeta®) for binding to HER2, as determined using a competition assay.

In some embodiments of any one of the kits described herein, the radiolabelled $V_{HH}$, or a functional fragment thereof, comprises one of the CDR combinations chosen from the group comprising:
a CDR1 region having SEQ ID NO:1, a CDR2 region having SEQ ID NO:2, and a CDR3 region having SEQ ID NO:3, and
a CDR1 region having SEQ ID NO:4, a CDR2 region having SEQ ID NO:5, and a CDR3 region having SEQ ID NO:6.

In some embodiments of any one of the kits described herein, the radiolabelled $V_{HH}$, or the functional fragment thereof, has at least 80% amino acid identity with at least one of the amino acid sequences of SEQ ID NOs:7 and 8. In some embodiments of any one of the kits described herein, the radiolabelled $V_{HH}$, or the functional fragment thereof, is identical with at least one of the amino acid sequences of SEQ ID NOs: 7 and 8.

In some embodiments of any one of the kits described herein, the screening dose and the therapeutic dose of the radiolabelled $V_{HH}$, or functional fragment thereof, are each independently formulated for administration to the subject intravenously, intraperitoneally, or intrathecally.

In some embodiments of any one of the kits described herein, the radiolabelled $V_{HH}$, or functional fragment thereof, is present in a monovalent format. In some embodiments of any one of the kits described herein, the radiolabelled $V_{HH}$, or functional fragment thereof, is devoid of a cysteine-containing tag, preferably a GGC-tag. In some embodiments of any one of the kits described herein, the radiolabelled $V_{HH}$, or functional fragment thereof, is non-lifetime extended. In some embodiments of any one of the kits described herein, the radiolabelled $V_{HH}$, or functional fragment thereof, is untagged.

DETAILED DESCRIPTION

Figure 1:
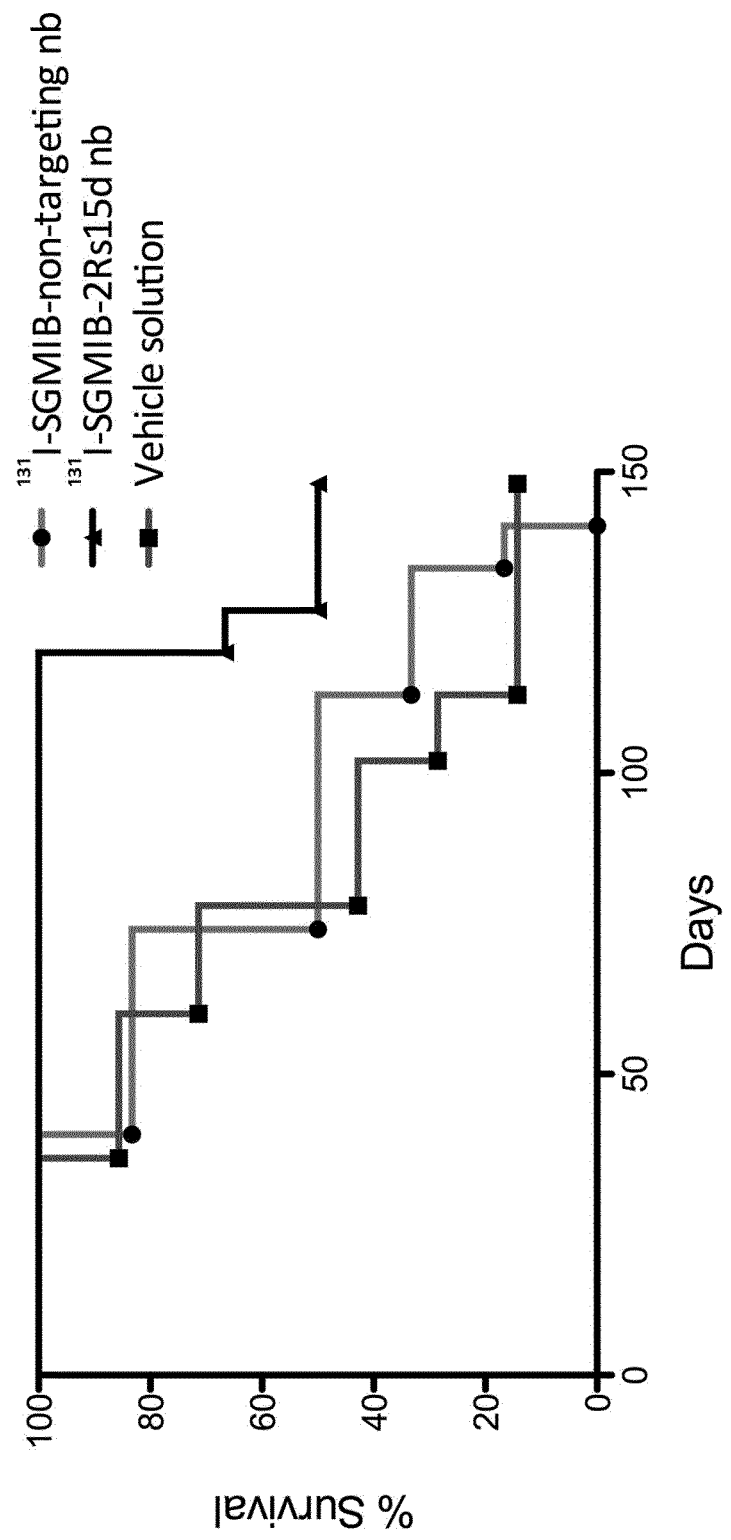
FIG. 1 shows the therapeutic effect of untagged monovalent [$^{131}$I]SGMIB-labeled anti-HER2 VHH 2Rs15d. Animals (n=6/7 per group) were treated with a weekly injection of untagged monovalent [$^{131}$I]SGMIB-labeled anti-HER2 VHH 2Rs15d ($^{131}$I-SGMIB-2Rs15d nb) and in the control groups with vehicle solution (vehicle solution) or untagged monovalent [$^{131}$I]SGMIB-labeled non-targeting control VHH ($^{131}$I-SGMIB-non-targeting nb). Animals were euthanized when more than 20% weight loss or a tumor volume of more than 1 cm$^3$ was reached. Survival of the animals in the different groups is shown.

Before the present invention is described, it is to be understood that this invention is not limited to particular methods and experimental conditions disclosed herein; as such methods and conditions may vary. It is also to be understood that the terminology used herein is for the purpose of describing particular embodiments only, and is not intended to be limiting, since the scope of the present invention will be limited only by the appended claims.

Furthermore, the practice of the invention employs, unless otherwise indicated, conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2$^{nd}$ edition).

I. Definitions

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting.

Generally, nomenclatures used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

As used herein, the singular forms "a", "an", and "the" include both singular and plural referents unless the context clearly dictates otherwise.

The terms "comprising", "comprises" and "comprised of" as used herein are synonymous with "including", "includes", "containing", or "contains", and are inclusive or open-ended and do not exclude additional, non-recited members, elements or method steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate with respect to the disclosure. It is to be understood that the value to which the modifier "about" refers is itself also specifically, and preferably, disclosed.

As used herein, amino acid residues will be indicated either by their full name or according to the standard three-letter or one-letter amino acid code.

As used herein, the terms "polypeptide", "protein", "peptide", and "amino acid sequence" are used interchangeably, and refer to a polymeric form of amino acids of any length, which can include coded and non-coded amino acids, chemically or biochemically modified or derivatized amino acids, and polypeptides having modified peptide backbones.

As used herein, the terms "nucleic acid molecule," "polynucleotide," "polynucleic acid," "nucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein, the term "homology" denotes at least secondary structural similarity between two macromolecules, particularly between two polypeptides or polynucleotides, from same or different taxons, wherein said similarity is due to shared ancestry. Hence, the term "homologues" denotes so-related macromolecules having said secondary and optionally tertiary structural similarity. For comparing two or more nucleotide sequences, in some embodiments, the "(percentage of) sequence identity" between a first nucleotide sequence and a second nucleotide sequence may be calculated using methods known by the person skilled in the art, e.g. by dividing the number of nucleotides in the first nucleotide sequence that are identical to the nucleotides at the corresponding positions in the second nucleotide sequence by the total number of nucleotides in the first nucleotide sequence and multiplying by 100% or by using a known computer algorithm for sequence alignment such as NCBI Blast. In determining the degree of sequence identity between two amino acid sequences, in some embodiments, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Possible conservative amino acid substitutions will be clear to the person skilled in the art. Amino acid sequences and nucleic acid sequences are said to be "exactly the same" if they have 100% sequence identity over their entire length.

The term "affinity", as used herein, refers to the degree to which a polypeptide, in particular an immunoglobulin, such as an antibody, or an immunoglobulin fragment, such as a $V_{HH}$, binds to an antigen so as to shift the equilibrium of antigen and polypeptide toward the presence of a complex formed by their binding. Thus, for example, where an antigen and antibody (e.g., antibody fragment) are combined in relatively equal concentration, an antibody (e.g., antibody fragment) of high affinity will bind to the available antigen so as to shift the equilibrium toward a high concentration of the resulting complex. The dissociation constant is commonly used to describe the affinity between the protein binding domain and the antigenic target. Typically, the dissociation constant is lower than $10^{-5}$ M. In some embodiments, the dissociation constant is lower than $10^{-6}$ M, more preferably, lower than $10^{-7}$ M, most preferably, lower than $10^{-8}$ M, such as lower than $10^{-9}$ M.

The terms "specifically bind" and "specific binding", as used herein, generally refers to the ability of a polypeptide, in particular an immunoglobulin, such as an antibody, or an immunoglobulin fragment, such as a $V_{HH}$ or functional fragments thereof, to preferentially bind to a particular antigen that is present in a homogeneous mixture of different antigens. In certain embodiments, a specific binding interaction will discriminate between desirable and undesirable antigens in a sample, in some embodiments more than about 10 to 100-fold or more (e.g., more than about 1000- or 10,000-fold).

Accordingly, an amino acid sequence, in particular an antibody fragment, such as a $V_{HH}$ or functional fragments thereof, as disclosed herein is said to "specifically bind to" a particular target when that amino acid sequence has affinity for, specificity for and/or is specifically directed against that target (or for at least one part or fragment thereof).

In some embodiments, an amino acid sequence, in particular an antibody fragment, such as a $V_{HH}$ or functional fragments thereof, as disclosed herein is said to be "specific for a first target antigen of interest as opposed to a second target antigen of interest" when it binds to the first target antigen of interest with an affinity that is at least 5 times, such as at least 10 times, such as at least 100 times, and preferably at least 1000 times higher than the affinity with which that amino acid sequence as disclosed herein binds to the second target antigen of interest. Accordingly, in certain embodiments, when an amino acid sequence as disclosed herein is said to be "specific for" a first target antigen of interest as opposed to a second target antigen of interest, it may specifically bind to (as defined herein) the first target antigen of interest, but not to the second target antigen of interest.

The "specificity" of an amino acid sequence, in particular an antibody fragment, such as a $V_{HH}$, or functional fragments thereof as disclosed herein can be determined based on affinity and/or avidity. The "affinity" of an amino acid sequence as disclosed herein is represented by the equilibrium constant for the dissociation of the amino acid sequence as disclosed herein and the target protein of interest to which it binds. The lower the $K_D$ value, the stronger the binding strength between the amino acid sequence as disclosed herein and the target protein of interest to which it binds. Alternatively, the affinity can also be expressed in terms of the affinity constant ($K_A$), which corresponds to $1/K_D$. The binding affinity of an amino acid sequence as disclosed herein can be determined in a manner known to the skilled person, depending on the specific target protein of interest. The "avidity" of an amino acid sequence as disclosed herein is the measure of the strength of binding between the amino acid sequence as disclosed herein and the pertinent target protein of interest. Avidity is related to both the affinity between a binding site on the target protein of interest and a binding site on the amino acid sequence as disclosed herein and the number of pertinent binding sites present on the amino acid sequence as disclosed herein. In some embodiments, the amino acid sequences as disclosed herein will bind to a target protein of interest with a dissociation constant ($K_D$) of less than about 1 micromolar (1 µM), and preferably less than about 1 nanomolar (1 nM) [i.e., with an association constant ($K_A$) of about 1,000,000 per molar ($10^6$ $M^{-1}$, 1E6/M) or more and preferably about 1,000,000,000 per molar ($10^9$ $M^{-1}$, 1E9/M) or more]. A $K_D$ value greater than about 1 millimolar is generally considered to indicate non-binding or non-specific binding. It is generally known in the art that the $K_D$ can also be expressed as the ratio of the dissociation rate constant of a complex, denoted as $k_{Off}$ (expressed in seconds$^{-1}$ or $s^{-1}$), to the rate constant of its association, denoted $k_{On}$ (expressed in molar$^{-1}$ seconds$^{-1}$ or $M^{-1}$ $s^{-1}$). In some embodiments, an amino acid sequence as disclosed herein will bind to the target protein of interest with a $k_{Off}$ ranging between 0.1 and 0.0001 $s^{-1}$ and/or a $k_{On}$ ranging between 1,000 and 1,000,000 $M^{-1}$ $s^{-1}$. Binding affinities, $k_{Off}$ and $L_{On}$ rates may be determined by means or methods known to the person skilled in the art, for example ELISA methods, isothermal titration calorimetry, surface plasmon resonance, fluorescence-activated cell sorting analysis, and the more.

In some embodiments, an amino acid sequence, in particular an antibody fragment, such as a $V_{HH}$, as disclosed herein is considered to be "(in) essentially isolated (form)" as used herein, when it has been extracted or purified from the host cell and/or medium in which it is produced.

In respect of the amino acid sequences, in particular antibody fragments, such as a $V_{HH}$'s or functional fragments thereof, as disclosed herein, the terms "binding region", "binding site" or "interaction site" present on the amino acid sequences as disclosed herein shall herein have the meaning of a particular site, part, domain or stretch of amino acid residues present in the amino acid sequence as disclosed herein that is responsible for binding to a target molecule. In some embodiments, such binding region essentially consists of specific amino acid residues from the amino acid sequence as disclosed herein which are in contact with the target molecule.

The terms "competing (with)", "cross-blocking", "cross-binding" and "cross-inhibiting" as used interchangeably herein, generally refer to an amino acid sequence, in particular an antibody fragment, such as a $V_{HH}$, as disclosed herein that can interfere with the binding of other amino acid sequence(s) as disclosed herein to a target protein of interest, as measured using a suitable in vitro, cellular or in vivo assay. Thus, in some embodiments, "competing (with)", "cross-blocking", "cross-binding" and "cross-inhibiting" using amino acid sequence as disclosed herein may mean interfering with or competing with the binding of another amino acid sequence as disclosed herein with a target protein of interest, thereby reducing that binding by at least 10% but preferably at least 20%, for example by at least 50%, at least 60%, at least 70%, at least 80%, at least 90%, at least 95% or more, as measured using a suitable in vitro, cellular or in vivo assay, compared to the binding of that other amino acid sequence as disclosed herein with the target protein of interest but without using the "cross-blocking" amino acid sequence as disclosed herein.

An amino acid sequence, in particular an antibody fragment, such as a $V_{HH}$ or functional fragments thereof, as disclosed herein is said to show "cross-reactivity" for two different target proteins of interest if it is specific for (as defined herein) both of these different target proteins of interest.

In cases where all of the two or more binding sites of amino acid sequence, in particular an antibody fragment, such as a $V_{HH}$ or functional fragments thereof, as disclosed herein are directed against or specifically bind to the same site, determinant, part, domain or stretch of amino acid residues of the target of interest, the amino acid sequence as disclosed herein is said to be "bivalent" (in the case of two binding sites on the amino acid sequence) or multivalent (in the case of more than two binding sites on the amino acid sequence), such as for example trivalent.

As used herein, the term "monovalent" when referring to an antibody fragment, such as a $V_{HH}$ or functional fragment thereof, denotes an antibody fragment in monomeric form. A monovalent antibody fragment contains only one binding site. In this context, the binding site of an antibody fragment, such as a $V_{HH}$ or functional fragments thereof, encompasses the one or more "complementarity determining regions" or "CDRs" of an antibody fragment that are directed against or specifically bind to a particular site, determinant, part, domain or stretch of amino acid residues of a target of interest.

As used herein, the term 'untagged' when referring to an antibody fragment, such as a $V_{HH}$ or functional fragments thereof, denotes an antibody fragment that contains no extraneous polypeptide sequences (e.g., contains only a $V_{HH}$ sequence, or a fragment thereof, labeled with a radioisotope as described herein). Exemplary extraneous polypeptide sequences include carboxy-terminal polypeptide tags, e.g., a His-tag, a cysteine-containing tag (e.g., a GGC-tag), and/or a Myc-tag.

The term "bi-specific" when referring to an amino acid sequence, in particular an antibody fragment, such as a $V_{HH}$, as disclosed herein implies that either a) two or more of the binding sites of an amino acid sequence as disclosed herein are directed against or specifically bind to the same target of interest but not to the same (i.e. to a different) site, determinant, part, domain or stretch of amino acid residues of that target, the amino acid sequence as disclosed herein is said to be "bi-specific" (in the case of two binding sites on the amino acid sequence) or multispecific (in the case of more than two binding sites on the amino acid sequence) or b) two or more binding sites of an amino acid sequence as disclosed herein are directed against or specifically bind to different target molecules of interest. The term "multispecific" is used in the case that more than two binding sites are present on the amino acid sequence as disclosed herein.

In some embodiments, a "bispecific" amino acid sequence or antibody fragment, such as a "bispecific" $V_{HH}$ or a "multi-specific" amino acid sequence or antibody fragment, such as a "multispecific" $V_{HH}$ as used herein, shall have the meaning of an amino acid sequence, in particular an antibody fragment, such as a $V_{HH}$, as disclosed herein comprising respectively two or at least two binding sites, wherein these two or more binding sites have a different binding specificity. In some embodiments, an amino acid sequence, in particular an antibody fragment, such as a $V_{HH}$, as disclosed herein is considered "bispecific" or "multispecific" if respectively two or more than two different binding regions exist in the same, monomeric, amino acid sequence.

The "half-life" of an amino acid sequence, in particular an antibody fragment, such as a $V_{HH}$ or functional fragments thereof, as disclosed herein can generally be defined as the time that is needed for the in vivo serum concentration of the amino acid sequence as disclosed herein to be reduced by 50%. The in vivo half-life of an amino acid sequence as disclosed herein can be determined in any manner known to the person skilled in the art, such as by pharmacokinetic analysis. As will be clear to the skilled person, the half-life can be expressed using parameters such as the t1/2-alpha, t1/2-beta and the area under the curve (AUC). An increased half-life in vivo is generally characterized by an increase in one or more and preferably in all three of the parameters t1/2-alpha, t1/2-beta and the area under the curve (AUC).

The term "lifetime extended" when referring to an antibody fragment, such as a $V_{HH}$ or functional fragments thereof as disclosed herein, is used to denote that the antibody fragment has been modified to extend the half-life of the antibody fragment. Strategies for extending the half-life of antibodies and antibody fragments are well-known in the art and include for example, but without limitation, linkage (chemically or otherwise) to one or more groups or moieties that extend the half-life, such as polyethylene glycol (PEG), bovine serum albumin (BSA), human serum albumin (HSA), antibody Fc fragments, or antigen-binding antibody fragments targeting serum proteins such as serum albumin.

As used herein, the terms "inhibiting", "reducing" and/or "preventing" may refer to (the use of) an amino acid sequence, in particular an antibody fragment, such as a $V_{HH}$ or functional fragments thereof, as disclosed herein that specifically binds to a target antigen of interest and inhibits, reduces and/or prevents the interaction between that target antigen of interest, and its natural binding partner. The terms "inhibiting", "reducing" and/or "preventing" may also refer to (the use of) an amino acid sequence, in particular an antibody fragment, such as a $V_{HH}$ or functional fragments thereof, as disclosed herein that specifically binds to a target antigen of interest and inhibits, reduces and/or prevents a biological activity of that target antigen of interest, as measured using a suitable in vitro, cellular or in vivo assay. Accordingly, "inhibiting", "reducing" and/or "preventing" may also refer to (the use of) an amino acid sequence as disclosed herein that specifically binds to a target antigen of interest and inhibits, reduces and/or prevents one or more biological or physiological mechanisms, effects, responses, functions pathways or activities in which the target antigen of interest is involved. Such an action of the amino acid sequence as disclosed herein as an antagonist may be determined in any suitable manner and/or using any suitable (in vitro and usually cellular or in vivo) assay known in the art, depending on the target antigen of interest.

Thus, in some embodiments, "inhibiting", "reducing" and/or "preventing" using amino acid sequence, in particular an antibody fragment, such as a $V_{HH}$ or functional fragments thereof, as disclosed herein may mean either inhibiting, reducing and/or preventing the interaction between a target antigen of interest and its natural binding partner, or, inhibiting, reducing and/or preventing the activity of a target antigen of interest, or, inhibiting, reducing and/or preventing one or more biological or physiological mechanisms, effects, responses, functions pathways or activities in which the target antigen of interest is involved, such as by at least 10%, but preferably at least 20%, for example by at least 50%, at least 60%, at least 70%, at least 80%, at least 90%, at least 95% or more, as measured using a suitable in vitro, cellular or in vivo assay, compared to the activity of the target antigen of interest in the same assay under the same conditions but without using the amino acid sequence as disclosed herein. In addition, "inhibiting", "reducing" and/or "preventing" may also mean inducing a decrease in affinity, avidity, specificity and/or selectivity of a target antigen of interest for one or more of its natural binding partners and/or inducing a decrease in the sensitivity of the target antigen of interest for one or more conditions in the medium or surroundings in which the target antigen of interest is present (such as pH, ion strength, the presence of co-factors, etc.), compared to the same conditions but without the presence of the amino acid sequence as disclosed herein. In the context of the present disclosure, "inhibiting", "reducing" and/or "preventing" may also involve allosteric inhibition, reduction and/or prevention of the activity of a target antigen of interest.

As used herein, the terms "enhancing", "increasing" and/or "activating" may refer to (the use of) an amino acid sequence, in particular an antibody fragment, such as a $V_{HH}$ or functional fragments thereof, as disclosed herein that specifically binds to a target protein of interest and enhances, increases and/or activates the interaction between that target protein of interest, and its natural binding partner. The terms "enhancing", "increasing" and/or "activating" may also refer to (the use of) an amino acid sequence, in particular an antibody fragment, such as a $V_{HH}$ or functional fragments thereof, as disclosed herein that specifically binds to a target protein of interest and enhances, increases and/or activates a biological activity of that target protein of interest, as measured using a suitable in vitro, cellular or in vivo assay. Accordingly, "enhancing", "increasing" and/or "activating" may also refer to (the use of) an amino acid sequence as disclosed herein that specifically binds to a target protein of interest and enhances, increases and/or activates one or more biological or physiological mechanisms, effects, responses, functions pathways or activities in which the target protein of interest is involved. Such an action of the amino acid sequence as disclosed herein as an agonist may be determined in any suitable manner and/or using any suitable (in vitro and usually cellular or in vivo) assay known in the art, depending on the target protein of interest.

The inhibiting or antagonizing activity or the enhancing or agonizing activity of an amino acid sequence, in particular an antibody fragment, such as a $V_{HH}$ or functional fragments thereof, as disclosed herein may be reversible or irreversible, but for pharmaceutical and pharmacological applications will typically occur reversibly.

As used herein, the term "antibody" refers to polyclonal antibodies, monoclonal antibodies, humanized antibodies, single-chain antibodies, and fragments thereof such as Fab F(ab)2, Fv, and other fragments that retain the antigen binding function of the parent antibody. As such, an antibody may refer to an immunoglobulin or glycoprotein, or fragment or portion thereof, or to a construct comprising an antigen-binding portion comprised within a modified immunoglobulin-like framework, or to an antigen-binding portion comprised within a construct comprising a non-immunoglobulin-like framework or scaffold.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments and others that retain the antigen binding function of the antibody. Monoclonal antibodies of any mammalian species can be used in this disclosure. In practice, however, the antibodies will typically be of rat or murine origin because of the availability of rat or murine cell lines for use in making the required hybrid cell lines or hybridomas to produce monoclonal antibodies.

As used herein, the term "polyclonal antibody" refers to an antibody composition having a heterogeneous antibody population. Polyclonal antibodies are often derived from the pooled serum from immunized animals or from selected humans.

"Heavy chain variable domain of an antibody or a functional fragment thereof", as used herein, means (i) the variable domain of the heavy chain of a heavy chain antibody, which is naturally devoid of light chains (also indicated hereafter as $V_{HH}$), including but not limited to the variable domain of the heavy chain of heavy chain antibodies of camelids or sharks or (ii) the variable domain of the heavy chain of a conventional four-chain antibody (also indicated hereafter as $V_H$), including but not limited to a camelized (as further defined herein) variable domain of the heavy chain of a conventional four-chain antibody (also indicated hereafter as camelized $V_H$) or any functional fragments thereof, such as but not limited to one or more stretches of amino acid residues (i.e. small peptides) that are particularly suited for binding to a tumor antigen or an antigen present on cancer cells and which are present in, and/or may be incorporated into, the $V_{HH}$'s as disclosed herein (or may be based on and/or derived from CDR sequences of the $V_{HH}$'s as disclosed herein).

As further described hereinbelow, the amino acid sequence and structure of a heavy chain variable domain of an antibody can be considered, without however being limited thereto, to be comprised of four framework regions or "FR's," which are referred to in the art and hereinbelow as "framework region 1" or "FR1;" as "framework region 2" or "FR2;" as "framework region 3" or "FR3;" and as "framework region 4" or "FR4," respectively, which framework regions are interrupted by three complementary determining regions or "CDR's," which are referred to in the art as "complementarity determining region 1" or "CDR1"; as "complementarity determining region 2" or "CDR2;" and as "complementarity determining region 3" or "CDR3," respectively.

As used herein, the terms "complementarity determining region" or "CDR" within the context of antibodies refer to variable regions of either the H (heavy) or the L (light) chains (also abbreviated as VH and VL, respectively) and contain the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have 3 CDR regions, each non-contiguous with the others (termed L1, L2, L3, H1, H2, H3) for the respective light (L) and heavy (H) chains.

In some embodiments, as also further described hereinbelow, the total number of amino acid residues in a heavy chain variable domain of an antibody (including a $V_{HH}$ or a $V_H$) can be in the region of 110-130, is preferably 112-115, and is most preferably 113. It should however be noted that parts, fragments or analogs of a heavy chain variable domain of an antibody are not particularly limited as to their length and/or size, as long as such parts, fragments or analogs retain (at least part of) the functional activity, and/or retain (at least part of) the binding specificity of the original a heavy chain variable domain of an antibody from which these parts, fragments or analogs are derived from. Parts, fragments or analogs retaining (at least part of) the functional activity, and/or retaining (at least part of) the binding specificity of the original heavy chain variable domain of an antibody from which these parts, fragments or analogs are derived from are also further referred to herein as "functional fragments" of a heavy chain variable domain.

The amino acid residues of a variable domain of a heavy chain variable domain of an antibody (including a $V_{HH}$ or a $V_H$) are numbered according to the general numbering for heavy chain variable domains given by Kabat et al. ("*Sequence of proteins of immunological interest*", US Public Health Services, NIH Bethesda, Md., Publication No. 91), as applied to $V_{HH}$ domains from Camelids in the article of Riechmann and Muyldermans, referred to below (see for example FIG. 2 of said reference). According to this numbering, FR1 of a heavy chain variable domain comprises the amino acid residues at positions 1-30, CDR1 of a heavy chain variable domain comprises the amino acid residues at positions 31-35, FR2 of a heavy chain variable domain comprises the amino acids at positions 36-49, CDR2 of a heavy chain variable domain comprises the amino acid residues at positions 50-65, FR3 of a heavy chain variable domain comprises the amino acid residues at positions 66-94, CDR3 of a heavy chain variable domain comprises the amino acid residues at positions 95-102, and FR4 of a heavy chain variable domain comprises the amino acid residues at positions 103-113. In this respect, it should be noted that—as is well known in the art for $V_{HH}$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.

Alternative methods for numbering the amino acid residues of heavy chain variable domains are the method described by Chothia et al. (Nature 342, 877-883 (1989)), the so-called "AbM definition" and the so-called "contact definition". However, in the present description, claims and figures, the numbering according to Kabat as applied to $V_{HH}$ domains by Riechmann and Muyldermans will be followed, unless indicated otherwise.

For a general description of heavy chain antibodies and the variable domains thereof, reference is inter alia made to the following references, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx NV; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551 by Ablynx N V and the further published patent applications by Ablynx N V; Hamers-Casterman et al., Nature 1993 Jun. 3; 363 (6428): 446-8; Davies and Riechmann, FEBS Lett. 1994 Feb. 21; 339(3): 285-90; Muyldermans et al., Protein Eng. 1994 September; 7(9): 1129-3; Davies and Riechmann, Biotechnology (NY) 1995 May; 13(5): 475-9; Gharoudi et al., 9th Forum of Applied Biotechnology, Med. Fac. Landbouw Univ. Gent. 1995; 60/4a part I: 2097-2100; Davies and Riechmann, Protein Eng. 1996 June; 9(6): 531-7; Desmyter et al., Nat. Struct. Biol. 1996 September; 3(9): 803-11; Sheriff et al., Nat Struct Biol. 1996 September; 3(9): 733-6; Spinelli et al., Nat Struct Biol. 1996 September; 3(9): 752-7; Arbabi Ghahroudi et al., FEBS Lett. 1997 Sep. 15; 414(3): 521-6; Vu et al., Mol. Immunol. 1997 November-December; 34(16-17): 1121-31; Atarhouch et al., Journal of Camel Practice and Research 1997; 4: 177-182; Ngyuen et al., J. Mol. Biol. 1998 Jan. 23; 275(3): 413-8; Lauwereys et al., EMBO J. 1998 Jul. 1; 17(13): 3512-20; Frenken et al., Res Immunol. 1998 July-August; 149(6):589-99; Transue et al., Proteins 1998 Sep. 1; 32(4): 515-22; Muyldermans and Lauwereys, J. Mol. Recognit. 1999 March-April; 12 (2): 131-40; van der Linden et al., Biochim. Biophys. Acta 1999 Apr. 12; 1431(1): 37-46; Decanniere et al., Structure Fold. Des. 1999 Apr. 15; 7(4): 361-70; Ngyuen et al., Mol. Immunol. 1999 June; 36(8): 515-24; Woolven et al., Immunogenetics 1999 October; 50 (1-2): 98-101; Riechmann and Muyldermans, J. Immunol. Methods 1999 Dec. 10; 231 (1-2): 25-38; Spinelli et al., Biochemistry 2000 Feb. 15; 39(6): 1217-22; Frenken et al., J. Biotechnol. 2000 Feb. 28; 78(1): 11-21; Nguyen et al., EMBO J. 2000 Mar. 1; 19(5): 921-30; van der Linden et al., J. Immunol. Methods 2000 Jun. 23; 240 (1-2): 185-95; Decanniere et al., J. Mol. Biol. 2000 Jun. 30; 300 (1): 83-91; van der Linden et al., J. Biotechnol. 2000 Jul. 14; 80(3): 261-70; Harmsen et al., Mol. Immunol. 2000 August; 37(10): 579-90; Perez et al., Biochemistry 2001 Jan. 9; 40(1): 74-83; Conrath et al., J. Biol. Chem. 2001 Mar. 9; 276 (10): 7346-50; Muyldermans et al., Trends Biochem Sci. 2001 April; 26(4):230-5; Muyldermans S., J. Biotechnol. 2001 June; 74 (4): 277-302; Desmyter et al., J. Biol. Chem. 2001 Jul. 13; 276 (28): 26285-90; Spinelli et al., J. Mol. Biol. 2001 Aug. 3; 311 (1): 123-9; Conrath et al., Antimicrob Agents Chemother. 2001 October; 45 (10): 2807-12; Decanniere et al., J. Mol. Biol. 2001 Oct. 26; 313(3): 473-8; Nguyen et al., Adv Immunol. 2001; 79: 261-96; Muruganandam et al., FASEB J. 2002 February; 16 (2): 240-2; Ewert et al., Biochemistry 2002 Mar. 19; 41 (11): 3628-36; Dumoulin et al., Protein Sci. 2002 March; 11 (3): 500-15; Cortez-Retamozo et al., Int. J. Cancer. 2002 Mar. 20; 98 (3): 456-62; Su et al., Mol. Biol. Evol. 2002 March; 19 (3): 205-15; van der Vaart J M., Methods Mol. Biol. 2002; 178: 359-66; Vranken et al., Biochemistry 2002 Jul. 9; 41 (27): 8570-9; Nguyen et al., Immunogenetics 2002 April; 54 (1): 39-47; Renisio et al., Proteins 2002 Jun. 1; 47 (4): 546-55; Desmyter et al., J. Biol. Chem. 2002 Jun. 28; 277 (26): 23645-50; Ledeboer et al., J. Dairy Sci. 2002 June; 85 (6): 1376-82; De Genst et al., J. Biol. Chem. 2002 Aug. 16; 277 (33): 29897-907; Ferrat et al., Biochem. J. 2002 Sep. 1; 366 (Pt 2): 415-22; Thomassen et al., Enzyme and Microbial Technol. 2002; 30: 273-8; Harmsen et al., Appl. Microbiol. Biotechnol. 2002 December; 60 (4): 449-54; Jobling et al., Nat. Biotechnol. 2003 January; 21 (1): 77-80; Conrath et al., Dev. Comp. Immunol. 2003 February; 27 (2): 87-103; Pleschberger et al., Bioconjug. Chem. 2003 March-April; 14 (2): 440-8; Lah et al., J. Biol. Chem. 2003 Apr. 18; 278 (16): 14101-11; Nguyen et al., Immunology. 2003 May; 109 (1): 93-101; Joosten et al., Microb. Cell Fact. 2003 Jan. 30; 2 (1): 1; Li et al., Proteins 2003 Jul. 1; 52 (1): 47-50; Loris et al., Biol. Chem. 2003 Jul. 25; 278 (30): 28252-7; van Koningsbruggen et al., J. Immunol. Methods. 2003 August; 279 (1-2): 149-61; Dumoulin et al., Nature. 2003 Aug. 14; 424 (6950): 783-8; Bond et al., J. Mol. Biol. 2003 Sep. 19; 332 (3): 643-55; Yau et al., J. Immunol. Methods. 2003 Oct. 1; 281 (1-2): 161-75; Dekker et al., J. Virol. 2003 November; 77 (22): 12132-9; Meddeb-Mouelhi et al., Toxicon. 2003 December; 42 (7): 785-91; Verheesen et al., Biochim. Biophys. Acta 2003 Dec. 5; 1624 (1-3): 21-8; Zhang et al., J Mol Biol. 2004 Jan. 2; 335 (1): 49-56; Stijlemans et al., J Biol. Chem. 2004 Jan. 9; 279 (2): 1256-61; Cortez-Retamozo et al., Cancer Res. 2004 Apr. 15; 64 (8): 2853-7; Spinelli et al., FEBS Lett. 2004 Apr. 23; 564 (1-2): 35-40; Pleschberger et al., Bioconjug. Chem. 2004 May-June; 15 (3): 664-71; Nicaise et al., Protein Sci. 2004 July; 13 (7): 1882-91; Omidfar et al., Tumour Biol. 2004 July-August; 25 (4): 179-87; Omidfar et al., Tumour Biol. 2004 September-December; 25(5-6): 296-305; Szynol et al., Antimicrob Agents Chemother. 2004 September; 48(9):3390-5; Saerens et al., J. Biol. Chem. 2004 Dec. 10; 279 (50): 51965-72; De Genst et al., J. Biol. Chem. 2004 Dec. 17; 279 (51): 53593-601; Dolk et al., Appl. Environ. Microbiol. 2005 January; 71(1): 442-50; Joosten et al., Appl Microbiol Biotechnol. 2005 January; 66(4): 384-92; Dumoulin et al., J. Mol. Biol. 2005 Feb. 25; 346 (3): 773-88; Yau et al., J Immunol Methods. 2005 February; 297 (1-2): 213-24; De Genst et al., J. Biol. Chem. 2005 Apr. 8; 280 (14): 14114-21; Huang et al., Eur. J. Hum. Genet. 2005 Apr. 13; Dolk et al., Proteins. 2005 May 15; 59 (3): 555-64; Bond et al., J. Mol. Biol. 2005 May 6; 348(3):699-709; Zarebski et al., J. Mol. Biol. 2005 Apr. 21.

Generally, it should be noted that the term "heavy chain variable domain" as used herein in its broadest sense is not limited to a specific biological source or to a specific method of preparation. For example, as will be discussed in more detail below, the heavy chain variable domains derived from heavy chain antibodies (i.e. $V_{HH}$'s) as disclosed herein can be obtained (1) by isolating the $V_{HH}$ domain of a naturally occurring heavy chain antibody; (2) by expression of a nucleotide sequence encoding a naturally occurring $V_{HH}$ domain; (3) by "camelization" (as described below) of a naturally occurring $V_H$ domain from any animal species, in particular a species of mammal, such as from a human being, or by expression of a nucleic acid encoding such a camelized $V_H$ domain; (4) by "camelization" of a "domain antibody" or "Dab" as described by Ward et al (supra), or by expression of a nucleic acid encoding such a camelized $V_H$ domain (5) using synthetic or semi-synthetic techniques for preparing proteins, polypeptides or other amino acid sequences; (6) by preparing a nucleic acid encoding a $V_{HH}$ using techniques for nucleic acid synthesis, followed by expression of the nucleic acid thus obtained; and/or (7) by any combination of the foregoing. Suitable methods and techniques for performing the foregoing will be clear to the skilled person based on the disclosure herein and for example include the methods and techniques described in more detail hereinbelow.

The term "effective amount", as used herein, means the amount needed to achieve the desired result or results.

As used herein, the terms "determining", "measuring", "assessing", "monitoring", "detecting" and "assaying" are used interchangeably and include both quantitative and qualitative determinations.

As used herein, the term "treatment" comprises preventing and/or treating a certain disease and/or disorder, preventing the onset of a certain disease and/or disorder, slowing down or reversing the progress of a certain disease and/or disorder, preventing or slowing down the onset of one or more symptoms associated with a certain disease and/or disorder, reducing and/or alleviating one or more symptoms associated with a certain disease and/or disorder, reducing the severity and/or the duration of a certain disease and/or disorder, and generally any prophylactic or therapeutic effect of the amino acid sequences as disclosed herein that is beneficial to the subject or patient being treated.

As used herein, the terms "diagnosis", "prediction" and/or "prognosis" comprise diagnosing, predicting and/or prognosing a certain disease and/or disorder, thereby predicting the onset and/or presence of a certain disease and/or disorder, and/or predicting the progress and/or duration of a certain disease and/or disorder, and/or predicting the response of a patient suffering from of a certain disease and/or disorder to therapy.

As used herein, the terms "tumor-specific antigen", "tumor antigen", "target protein present on a cancer cell or solid tumor", "tumor-specific target (protein)", "tumor-associated antigen" are used interchangeably herein and include any protein which is present only on tumor cells and not on any other cell and also include any protein which is present on some tumor cells and also on some normal, healthy cells. Non-limiting examples of tumor antigens include tissue differentiation antigens, mutant protein antigens, oncogenic viral antigens, cancer-testis antigens and vascular or stromal specific antigens.

As used herein, the terms "tumor cell" or "cancer cell" are used interchangeably and refer to a cell that is present in a primary or metastatic tumor lesion. In some embodiments, tumors consist not only of cancer cells, but should be considered as organ-like structures in which a complex bidirectional interplay exists between transformed and non-transformed cells. In some embodiments, the malignant potential of transformed cells requires an apt support structure from the stroma, which can consist of fibroblasts, adipocytes, blood and lymph vessels, but may also be considerably infiltrated by a wide range of immune cells. In some embodiments, the tumor cell is a hematological tumor cell. In some embodiments, the tumor cell is a solid tumor cell.

As used herein, the term "radiolabelled" as in a "radiolabelled" amino acid sequence, "radiolabelled" antibody fragment, or "radiolabelled" $V_{HH}$, refers to the radioisotopic labeling of that amino acid sequence, antibody fragment or $V_{HH}$, wherein the amino acid sequence, antibody fragment or $V_{HH}$ is labelled by including, coupling, or chemically linking a radionuclide to its amino acid sequence structure. The radiolabelled antibody fragments disclosed herein can be derived from a naturally occurring polypeptide, or alternatively they can be entirely artificially designed. Non-limiting examples of such naturally occurring polypeptides which may be radiolabelled include heavy chain antibodies (hcAb), such as but not limited to camelid heavy chain antibodies.

As used herein, the terms "radionuclide", "radioactive nuclide", "radioisotope" or "radioactive isotope", are used interchangeably herein and refer to atoms with an unstable nucleus, characterized by excess energy available to be imparted either to a newly created radiation particle within the nucleus or via internal conversion. During this process, the radionuclide is said to undergo radioactive decay, resulting in the emission of gamma ray(s) and/or subatomic particles such as alpha or beta particles. These emissions constitute ionizing radiation. Radionuclides occur naturally, or can be produced artificially. In some embodiments, the radioisotope is both a "γ-emitter and β-emitter", meaning the radioisotope emits both gamma (γ) rays and beta (β) particles.

By "cancer" or "tumor(s)" are meant primary tumors and/or metastases (wherever located) such as but not limited to solid tumors or hematological cancers, or metastases of solid tumors or hematological cancers. In some embodiments, a "solid tumor" is a tumor that forms a discrete tumor mass, e.g., sarcomas and carcinomas. In some embodiments, a "hematological cancer" is a cancer of blood cells, such as leukemia, lymphoma, or myeloma. In some embodiments, the cancer is breast cancer, ovarian cancer, gastric cancer, multiple myeloma, or lymphoma.

As used herein, the term "cancer cell" refers to a cell that divides and reproduces abnormally (and, in some embodiments, limitlessly) with uncontrolled growth and which can break away and travel to other parts of the body and set up another site, referred to as metastasis.

A "lesion" as used herein can refer to any abnormal change in a body tissue or organ resulting from injury or disease. In cancer terminology, lesion typically refers to a tumor. As used herein, the term "HER-2 positive" as in "HER-2 positive (cancer) lesions", "HER-2 positive (breast) cancer", or "HER-2 positive tumor" refers to cancerous or malignant cells or tissue characterized by HER2 gene amplification or HER2 protein overexpression and thus have abnormally high levels of the HER2 gene and/or the HER2 protein compared to normal healthy cells. HER-2 positive breast cancer is characterized by cancerous breast cells characterized by HER2 gene amplification or HER2 protein overexpression. In about 1 of every 5 breast cancers, the cancer cells make an excess of HER2, mainly caused by HER2 gene amplification due to one or more gene mutations. The elevated levels of HER2 protein that it causes can occur in many types of cancer—and are thus not limited to breast cancer.

As used herein, the term "HER-2 negative" as in "HER-2 negative (cancer) lesions", "HER-2 negative (breast) cancer", "HER-2 negative tumor", "HER-2 negative cell(s)" can refer either to cancerous or malignant cells or tissue or to normal healthy cells or tissue, both of which are characterized by the absence of HER2 gene amplification or HER2 protein overexpression and thus by normal levels of the HER2 gene and/or the HER2 protein.

The term "in situ hybridization (ISH)" as used herein refers to a type of hybridization assay that uses a labeled complementary DNA or RNA strand (i.e., probe) to localize a specific DNA or RNA sequence in a portion or section of tissue (in situ), or, if the tissue is small enough (e.g. plant seeds, Drosophila embryos), in the entire tissue (whole mount ISH), in cells and in circulating tumor cells (CTCs). In situ hybridization is a powerful technique for identifying specific mRNA species within individual cells in tissue sections, providing insights into physiological processes and disease pathogenesis. In particular, in situ hybridization is used to reveal the location of specific nucleic acids sequences on chromosomes or in tissues, a crucial step for understanding the organization, regulation and function of genes. The key techniques currently in use include: in situ hybridization to mRNA with oligonucleotide and RNA probes (both radio labelled and hapten labelled); analysis with light and electron microscopes; whole mount in situ hybridization; double detection of RNAs and RNA plus protein; and fluorescent in situ hybridization to detect chromosomal sequences. DNA ISH can be used to determine the structure of chromosomes. Fluorescent DNA ISH (FISH) can, for example, be used in medical diagnostics to assess chromosomal integrity. RNA ISH (RNA in situ hybridization) is used to measure and localize RNAs (mRNAs, lncRNAs and miRNAs) within tissue sections, cells, whole mounts, and circulating tumor cells (CTCs).

The term "fluorescence in situ hybridization (FISH)" as used herein refers to a specific type of in situ hybridization assay that is used to detect and localize the presence or absence of specific DNA sequences on chromosomes. FISH uses fluorescent probes that bind to only those parts of the chromosome with which they show a high degree of sequence complementarity. Fluorescence microscopy can be used to find out where the fluorescent probe is bound to the chromosomes. FISH is often used for finding specific features in DNA for use in genetic counseling, medicine, and species identification. FISH can also be used to detect and localize specific RNA targets (mRNA, lncRNA and miRNA) in cells, circulating tumor cells, and tissue samples. In this context, it can help define the spatial-temporal patterns of gene expression within cells and tissues.

The term "immunohistochemistry (IHC)" as used herein refers to the process of detecting antigens (e.g., proteins) in cells of a tissue section by exploiting the principle of antibodies binding specifically to antigens in sections of biological tissues. Immunohistochemical staining is widely used in the diagnosis of abnormal cells such as those found in cancerous tumors. IHC is also widely used in basic research to understand the distribution and localization of biomarkers and differentially expressed proteins in different parts of a biological tissue.

"Trastuzumab" (Trade names: HERCLON®, Herceptin®) is a monoclonal antibody that interferes with the HER2/neu receptor. Its main use is to treat certain breast cancers.

"Pertuzumab" or "2C4" (Trade name: PERJETA®) is a monoclonal antibody that binds to HER2, more particularly domain II of HER2, thereby inhibiting the dimerization of HER2 with other HER receptors. Its main use is to treat HER2-positive breast cancers.

The term "primary tumor(s)" as used herein is a tumor growing at the anatomical site where tumor progression began and proceeded to yield a cancerous mass.

The term "metastatic lesion(s)" as used herein refers to malignant, or cancerous, tumors that have spread from their original location to other parts of the body. Related medical terms that might be used interchangeably include "late-stage cancer", "advanced cancer", or "metastatic disease". In general, metastatic lesions are considered to be incurable, although treatment is often available to control the spread of cancerous cells and potentially increase the individual's life expectancy.

Metastasis is the term for the spread of cancer beyond its originating site in the body. Thus, metastatic lesions are cancerous tumors that are found in locations apart from the original starting point of the primary tumor. Metastatic tumors occur when cells from the primary tumor break off and travel to distant parts of the body via the lymph system and blood stream. Alternately, cells from the original tumor could seed into new tumors at adjacent organs or tissues. "Metastatic disease" as used herein refers to late-stage cancer and to the medical classification of cancer as being in stage III, when cancer cells are found in lymph nodes near the original tumor, or in stage IV, when cancer cells have traveled far beyond the primary tumor site to distant parts of the body. Metastatic lesions are most commonly found in the brain, lungs, liver, or bones. An individual with metastatic cancer might or might not experience any symptoms, and the symptoms could be related to the area where metastasized cells have relocated. Once metastatic lesions are present in the body, the individual's cancer may be considered incurable for most cancer types. This means it is excessively difficult to eradicate every existing cancer cell with available treatments. In this case, the goal of treatment becomes slowing the growth of tumors to maintain the highest possible quality of life and potentially extend the individual's life expectancy. In some cases, people with metastatic lesions can live for a number of years with appropriate treatment for symptom management.

The "(calculated mean) effective dose" of radiation within a subject as used herein refers to the tissue-weighted sum of the equivalent doses in all specified tissues and organs of the body and represents the stochastic health risk, which the probability of cancer induction and genetic effects of ionizing radiation delivered to those body parts. It takes into account the type of radiation and the nature of each organ or tissue being irradiated. It is the central quantity for dose limitation in radiological protection in the international system of radiological protection devised by the International Commission on Radiological Protection (ICRP). The SI unit for effective dose is the sievert (Sv) which is one joule/kilogram (J/kg). The effective dose replaced the former "effective dose equivalent" in 1991 in the ICRP system of dose quantities. For procedures using radiopharmaceuticals, the effective dose is typically expressed per unit of injected activity, i.e. expressed in mSv/MBq. The effective dose for the individual patient will then depend upon the injected activity of the radiopharmaceutical, expressed in MBq, and the calculated mean effective dose, expressed in mSv/MBq.

The effective dose for radiopharmaceuticals is calculated using OLINDA/EXM® software, that was approved in 2004 by the FDA. The OLINDA/EXM® personal computer code performs dose calculations and kinetic modeling for radiopharmaceuticals (OLINDA/EXM stands for Organ Level INternal Dose Assessment/EXponential Modeling). OLINDA® calculates radiation doses to different organs of the body from systemically administered radiopharmaceuticals and performs regression analysis on user-supplied biokinetic data to support such calculations for nuclear medicine drugs. These calculations are used to perform risk/benefit evaluations of the use of such pharmaceuticals in diagnostic and therapeutic applications in nuclear medicine. The technology employs a number of standard body models for adults, children, pregnant women and others, that are widely accepted and used in the internal dose community. The calculations are useful to pharmaceutical industry developers, nuclear medicine professionals, educators, regulators, researchers and others who study the accepted radiation doses that should be delivered when radioactive drugs are given to patients or research subjects.

The calculated effective dose depends on the chosen standard body model and the chosen voiding bladder model. The values provided herein have been calculated using the female adult model and a voiding bladder interval of 1 h.

As used herein, a "screening dose" or a "biomarker dose" is a dose of an agent, such as a radiolabelled antibody fragment as described herein, that is sufficient for selecting a subject for treatment, such as a dose that can bind to a cancer cell or solid tumor in the subject and subsequently be detected at the location of the cancer cell or solid tumor, e.g., by imaging the subject using gamma camera imaging such as planar gamma camera imaging, single photon emission computed tomography or positron emission tomography, optionally combined with a non-nuclear imaging technique such as X-ray imaging, computed tomography and/or magnetic resonance imaging. In some embodiments, a screening dose is a dose that is not therapeutically effective. In some embodiments, the screening dose is different than (e.g., lower than) a therapeutic dose as described herein.

As used herein, a "therapeutic dose" is a dose of an agent, such as a radiolabelled antibody fragment as described herein, that is therapeutically effective in at least 1%, at least 5%, at least 10%, at least 20%, at least 30%, at least 40%, or at least 50% of subjects in need of such treatment (e.g., in subjects having cancer). In some embodiments, the therapeutic dose is higher than a screening dose as described herein.

As used herein, "imaging a subject" refers to capturing one or more images of a subject using a device that is capable of detecting a radiolabelled antibody fragment as described herein. The one or more images may be further altered by a computer program and/or a person skilled in the art in order to enhance the images (e.g., by adjusting contrast or brightness of the one or more images). Any device capable of detecting a radiolabelled antibody fragment as described herein is contemplated for use, such as a device for gamma camera imaging such as planar gamma camera imaging, for single photon emission computed tomography or for positron emission tomography, or a device able to combine a nuclear imaging technique with a non-nuclear imaging technique such as X-ray imaging, computed tomography and/or magnetic resonance imaging. For example, such device can be a device for single photon emission computed tomography/computed tomography (SPECT/CT) imaging. Such devices are known in the art and commercially available.

As used herein, the term "subject" generally refers to a mammal, such as a human, a non-human primate, a rat, a mouse, a rabbit, a dog, a cat, a pig, a horse, a goat, or a sheep. In some embodiments, the subject is a human subject. In some embodiments, the subject is a subject having cancer (e.g., a human subject having cancer). Methods for identifying subjects having cancer include detection of tumor antigens or other tumor biomarkers, genetic testing, MRI, X-ray, PET scan, biopsies, and combinations thereof.

As used herein, the term "linker" refers to a moiety that attaches one molecule to another molecule (e.g., attaches a radioisotope to an antibody fragment such as a $V_{HH}$ or functional fragment thereof). The linker may be a chemical linker, a nucleotide linker, a peptide linker, or any combination thereof.

II. Methods and Compositions for Stratification and Treatment of Subjects

In one aspect, the disclosure provides methods for stratifying and treating subjects, e.g., to select subjects for treatment and subsequently treating the selected subjects.

In some embodiments, the method comprises selecting a subject (e.g., a subject having cancer as described herein) for treatment on the basis of detection in the subject of a screening dose of a radiolabelled antibody fragment (e.g., a radiolabelled $V_{HH}$, or a functional fragment thereof), which specifically binds to a target protein that is present on a cancer cell or solid tumor; and administering to the subject a therapeutic dose of the radiolabelled antibody fragment. In some embodiments, the radiolabelled antibody fragment is radiolabelled with a radioisotope that is both a γ-emitter and β-emitter. Examples of suitable radioisotopes that are both β-emitters and γ-emitters include, for example, Iodine-131, Lutetium-177, Yttrium-90, Copper-67, Rhenium-186, and Rhenium-188. In some embodiments, the radioisotope is Iodine-131.

In some embodiments of any one of the methods provided, a screening dose is a dose that is not therapeutically effective. In some embodiments of any one of the methods provided, the screening dose is lower than a therapeutic dose as described herein (e.g., at least about 10 times, at least about 20 times, at least about 30 times, at least about 40 times, at least about 50 times, at least about 100 times, at least about 200 times, at least about 300 times, at least about 400 times, at least about 500 times or at least about 1000 times lower than a therapeutic dose as described herein, or at least about 10, at least about 20, at least about 30, at least about 40, at least about 50, at least about 60, at least about 70, at least about 80, at least about 90, at least about 100, at least about 120, at least about 130, at least about 140, at least about 150, at least about 160, at least about 170, at least about 180, at least about 190, at least about 200, at least about 210, at least about 220, at least about 230, at least about 240, at least about 250, at least about 260, at least about 270, at least about 280, at least about 290, at least about 300, at least about 320, at least about 340, at least about 360, at least about 380, at least about 400, at least about 450, at least about 500, at least about 1000, at least about 5000, at least about 10000, at least about 13000, at least about 15000, at least about 18000, or at least about 20000 MBq lower than a therapeutic dose as described herein). In some embodiments of any one of the methods provided, the screening dose is between 10 about MBq and about 400 MBq, between about 20 MBq and about 400 MBq, between about 30 MBq and about 400 MBq, about 40

MBq and about 400 MBq, between about 50 MBq and about 400 MBq, between about 100 MBq and about 400 MBq, between about 200 MBq and about 400 MBq, between about 300 MBq and about 400 MBq, between about 10 MBq and about 300 MBq, between about 20 MBq and about 300 MBq, between about 30 MBq and about 300 MBq, about 40 MBq and about 300 MBq, between about 50 MBq and about 300 MBq, between about 100 MBq and about 300 MBq, or between about 200 MBq and about 300 MBq. In some embodiments of any one of the methods provided, the screening dose is between 3 about 7 MBq and about 370 MBq. It is to be understood that any screening dose described herein may be combined with any therapeutic dose as described herein.

In some embodiments of any one of the methods provided, the therapeutic dose is higher than a screening dose as described herein (e.g., at least about 10 times, at least about 20 times, at least about 30 times, at least about 40 times, at least about 50 times, at least about 100 times, at least about 200 times, at least about 300 times, at least about 400 times, at least about 500 times or at least about 1000 times higher than a screening dose as described herein, or at least about 10, at least about 20, at least about 30, at least about 40, at least about 50, at least about 60, at least about 70, at least about 80, at least about 90, at least about 100, at least about 120, at least about 130, at least about 140, at least about 150, at least about 160, at least about 170, at least about 180, at least about 190, at least about 200, at least about 210, at least about 220, at least about 230, at least about 240, at least about 250, at least about 260, at least about 270, at least about 280, at least about 290, at least about 300, at least about 320, at least about 340, at least about 360, at least about 380, at least about 400, at least about 450, at least about 500, at least about 1000, at least about 5000, at least about 10000, at least about 13000, at least about 15000, at least about 18000, or at least about 20000 MBq higher than a screening dose as described herein). In some embodiments of any one of the methods provided, the therapeutic dose is between about 300 MBq and about 20000 MBq, between about 400 MBq and about 20000 MBq, between about 500 MBq and about 20000 MBq, between about 1000 MBq and about 20000 MBq, between about 2000 MBq and about 20000 MBq, between about 3000 MBq and about 20000 MBq, between about 4000 MBq and about 20000 MBq, between about 5000 MBq and about 20000 MBq, between about 10000 MBq and about 20000 MBq, between about 5000 MBq and about 20000 MBq, between about 10000 MBq and about 20000 MBq, between about 300 MBq and about 10000 MBq, between about 400 MBq and about 10000 MBq, between about 500 MBq and about 10000 MBq, between about 1000 MBq and about 10000 MBq, between about 2000 MBq and about 10000 MBq, between about 3000 MBq and about 10000 MBq, between about 4000 MBq and about 10000 MBq, or between about 5000 MBq and about 10000 MBq. In some embodiments of any one of the methods provided, the therapeutic dose is between about 370 MBq and about 18500 MBq.

The particular screening dose and therapeutic dose utilized may, in some embodiments, depend on the nature of the disease (e.g., type, grade, and stage of the tumor or cancer cell etc.) and the type of subject (e.g., species, constitution, age, gender, weight, etc.).

In some embodiments of any one of the methods provided, the method further comprises administering the screening dose to the subject and detecting the presence of the radiolabelled $V_{HH}$, or functional fragment thereof, at a tumor site in the subject prior to selecting the subject. The tumor site may be, e.g., a solid tumor site (e.g., one or more organs or tissues in a subject) or a hematological cancer site (e.g., in the circulatory system, or a portion thereof, of the subject). In some embodiments, the administration of the screening dose and the detection are separated by at least 1 about minute, at least 5 about minutes, at least about 10 minutes, at least about 20 minutes, at least about 30 minutes, at least about 40 minutes, at least about 50 minutes, at least about 1 hour, at least about 1.5 hours, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 24 hours, at least about 2 days, or at least about 7 days. In some embodiments, the administration of the screening dose and the detection are separated by between about 1 hour and about 24 hours.

In some embodiments of any one of the methods provided, detecting the presence of the radiolabelled $V_{HH}$, or functional fragment thereof, comprises imaging the subject. In some embodiments, the imaging is gamma camera imaging such as planar gamma camera imaging, single photon emission computed tomography or positron emission tomography, optionally combined with a non-nuclear imaging technique such as X-ray imaging, computed tomography and/or magnetic resonance imaging. In particular embodiments, the imaging is single photon emission computed tomography combined with computed tomography (SPECT/CT).

In some embodiments of any one of the methods provided, the screening dose and the therapeutic dose are administered at least about 1 day, at least about 2 days, at least about 3 days, at least about 4 days, at least about 5 days, at least about 6 days, at least about 1 week, at least about 2 weeks, at least about 3 weeks, at least one month, at least about 2 months, or at least about 6 months apart. In some embodiments of any one of the methods provided, the screening dose and the therapeutic dose are administered between about 1 day and about 6 months apart (e.g., between about 1 day and about 2 months, between about 1 day and about 1 month, or between about 1 day and about 1 week apart).

In some embodiments of any one of the methods provided, the radiolabelled $V_{HH}$, or functional fragment thereof, specifically binds to HER2. Such radiolabelled $V_{HH}$s, or functional fragments thereof, that specifically bind to HER2 are further described herein.

The screening dose and therapeutic dose may each independently be administered by any suitable route, such as systemically, locally or topically. Exemplary routes include intravenous, intraperitoneal, and intrathecal administration. The particular route utilized may, in some embodiments, depend on the nature of the disease (e.g., type, grade, location and stage of the tumor or cancer cell etc.) and the type of subject (e.g., species, constitution, age, gender, weight, etc.).

In yet a further aspect, one or more compositions are provided for use in a method described herein, the composition(s) comprising a radiolabelled antibody fragment as disclosed herein (e.g., a radiolabelled $V_{HH}$, or a functional fragment thereof) and/or nucleic acid sequences as envisaged herein and optionally at least one acceptable carrier. According to some embodiments, the composition(s) may further comprise at least one other compound. In some embodiments, a screening composition and a therapeutic composition are provided, where the screening composition and the therapeutic composition have different amounts of the radiolabelled antibody fragment as disclosed herein (e.g., different amounts of a radiolabelled $V_{HH}$, or a functional fragment thereof).

In some embodiments, the compositions as disclosed herein are pharmaceutical compositions.

The pharmaceutical composition(s) can be used in a method described herein (e.g., a method of stratifying and treating a subject as described herein, such as a human subject or other mammalian subject).

Generally, for pharmaceutical use, a radiolabelled antibody fragment as disclosed herein (e.g., a radiolabelled $V_{HH}$, or a functional fragment thereof) may be formulated as a pharmaceutical preparation or compositions comprising at least one radiolabelled antibody fragment (e.g., a radiolabelled $V_{HH}$, or a functional fragment thereof) as described herein and at least one pharmaceutically acceptable carrier, diluent or excipient and/or adjuvant, and optionally one or more further pharmaceutically active polypeptides and/or compounds. Such a formulation may be suitable, e.g., for intraperitoneal, intravenous, intrathecal, or other administration.

Pharmaceutical dosage forms suitable for injection or infusion can include sterile aqueous solutions or dispersions or sterile powders comprising the active ingredients which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof.

In some embodiments, the present disclosure provides a radiolabelled $V_{HH}$ or functional fragment thereof as disclosed herein in an amount of between 10 µg and 1000 µg, in particular in an amount of between about 10 µg and about 100 µg, more particularly in an amount of between about 20 µg and about 100 µg, such as in amount of about 50 µg, of $V_{HH}$ or functional fragment thereof. In some embodiments, the present disclosure provides a screening dose and a therapeutic dose as described herein each independently having an amount of between 10 µg and 1000 µg, in particular an amount of between about 10 µg and about 100 µg, more particularly an amount of between about 20 µg and about 100 µg, such as amount of about 50 µg, of $V_{HH}$ or functional fragment thereof as described herein. In some embodiments, the present disclosure provides a screening dose and a therapeutic dose as described herein each independently having an amount of between 10 µg and 1000 µg in particular an amount of between about 10 µg and about 100 µg, more particularly an amount of between about 20 µg and about 100 µg, such as amount of about 50 µg, of $V_{HH}$ or functional fragment thereof as described herein, wherein the screening dose has a lower specific activity than the therapeutic dose (e.g., a lower amount of radioactivity for the same or a similar amount, such as within 10 or 100 µg, of $V_{HH}$ or functional fragment thereof). In some embodiments, the present disclosure provides a screening dose of 37 MBq and 370 MBq of a radiolabelled $V_{HH}$ or functional fragment thereof as disclosed herein, wherein the amount of $V_{HH}$ or functional fragment thereof present in the dose is between 10 µg and 1000 µg, in particular between about 10 µg and about 100 µg, more particularly between about 20 µg and about 100 µg, such about 50 µg. In some embodiments, the present disclosure provides a therapeutic dose of 370 MBq and 18500 MBq of a radiolabelled $V_{HH}$ or functional fragment thereof as disclosed herein, where the amount of $V_{HH}$ or functional fragment thereof present in the dose is between 10 µg and 1000 µg, in particular between about 10 µg and about 100 µg, more particularly between about 20 µg and about 100 µg, such about 50 µg.

The screening and/or therapeutic dose may conveniently be presented in a single dose or as divided doses (which can again be sub-dosed) administered at appropriate intervals. An administration regimen of the therapeutic dose could include long-term (e.g., at least two weeks, and for example several months or years) or daily treatment. In some embodiments, an administration regimen of the therapeutic dose can vary between once a day to once a month, such as between once a day and once every two weeks, such as but not limited to once a week. Thus, in some embodiments, pharmaceutical compositions as disclosed herein may be administered once or several times, also intermittently, for instance on a daily basis for several days, weeks or months.

In some embodiments, a radiolabelled antibody fragment as disclosed herein (e.g., a radiolabelled $V_{HH}$, or a functional fragment thereof) may be used in combination with other pharmaceutically active compounds or principles that are or can be used for the prevention and/or treatment of the diseases and disorders cited herein, as a result of which a synergistic effect may or may not be obtained.

In some embodiments, a radiolabelled antibody fragment as disclosed herein (e.g., a radiolabelled $V_{HH}$, or a functional fragment thereof) comprising a $V_{HH}$ sequence as disclosed herein are applied together with one or more therapeutic antibodies or therapeutic antibody fragments. Thus, in some embodiments, the therapeutic dose of the radiolabelled antibody fragment as disclosed herein is combined with regular immunotherapy with one or more therapeutic antibodies or therapeutic antibody fragments. In some embodiments, the radiolabelled $V_{HH}$ sequences or functional fragments thereof as disclosed herein are used in a combination therapy or a combination treatment method with one or more therapeutic antibodies or therapeutic antibody fragments, such as but not limited to a combination treatment with Trastuzumab (Herceptin®) and/or Pertuzumab (Perjeta®). If the two drugs are administered at the same time, they may be formulated together in one single pharmaceutical preparation, or they may be mixed together immediately before administration from two different pharmaceutical preparations, for example by dissolving or diluting into one single infusion solution. In another embodiment, the two drugs are administered separately, i.e. as two independent pharmaceutical compositions.

The present disclosure also embraces the use of further agents, which are administered in addition to the combination as defined. This could be, for example, one or more further chemotherapeutic agent(s). It could also be one or more agent(s) applied to prevent, suppress, or ameliorate unwanted side effects of any of the other drugs given. For example, a cytokine stimulating proliferation of leukocytes may be applied to ameliorate the effects of leukopenia or neutropenia.

The efficacy of a radiolabelled antibody fragment as disclosed herein (e.g., a radiolabelled $V_{HH}$, or a functional fragment thereof), and of compositions comprising the same, can be tested using any suitable in vitro assay, cell-based assay, in vivo assay and/or animal model known in the art or described herein, or any combination thereof, depending on the specific disease or disorder involved. Suitable assays and animal models will be clear to the skilled person.

III. Radiolabelled Antibody Fragments

In one aspect, the present disclosure provides radiolabelled antibody fragments, such as $V_{HH}$ sequences or functional fragments thereof, specifically directed against a tumor antigen and/or a cancer cell antigen for use in the stratification and subsequent treatment of subjects, such as subjects having cancer.

The radiolabelled antibody fragments disclosed herein can be made using any method known in the art or described herein, e.g., the radiolabelled antibody fragments disclosed herein can be derived from a naturally occurring polypeptide, or alternatively they can be entirely artificially designed. Non-limiting examples of such naturally occurring polypeptides include heavy chain antibodies (hcAb), such as but not limited to camelid heavy chain antibodies.

In some embodiments, the heavy chain variable domains derived from heavy chain antibodies (i.e. the $V_{HH}$'s) as disclosed herein consist of a single polypeptide chain and are not post-translationally modified. In some embodiments, the $V_{HH}$'s or functional fragments thereof disclosed herein are derived from an innate or adaptive immune system, preferably from a protein of an innate or adaptive immune system. In some embodiments, the $V_{HH}$'s disclosed herein comprise 4 framework regions and 3 complementary determining regions, or any suitable fragment thereof (which will then usually contain at least some of the amino acid residues that form at least one of the complementary determining regions). In some embodiments, the $V_{HH}$'s disclosed herein are produced at high yield, preferably in a microbial recombinant expression system, and are isolated and/or purified subsequently.

According to particular embodiments, the disclosure provides a number of stretches of amino acid residues that are particularly suited for binding to a tumor antigen or a cancer cell antigen, such as but not limited to HER2. These stretches of amino acid residues may be present in, and/or may be incorporated into, the $V_{HH}$'s as disclosed herein, in particular in such a way that they form (part of) the antigen binding site of that $V_{HH}$. As these stretches of amino acid residues were first generated as CDR sequences of antibodies (or may be based on and/or derived from such CDR sequences, as further described herein), they will also generally be referred to herein as 'CDR sequences' (e.g., as CDR1 sequences, CDR2 sequences and CDR3 sequences, respectively). It should however be noted that the disclosure in its broadest sense is not limited to a specific structural role or function that these stretches of amino acid residues may have in the heavy chain variable domains as disclosed herein, as long as these stretches of amino acid residues allow the variable domains as disclosed herein to specifically bind to a tumor antigen and/or a cancer cell-specific antigen. Thus, in some embodiments, the disclosure relates to radiolabelled $V_{HH}$'s for use in the stratification and treatment of cancer, which $V_{HH}$'s comprise a combination of CDR sequences as described herein and are specifically directed to a tumor-specific or a cancer cell-specific target protein.

Thus, in particular, but non-limiting embodiments, the VHH's as disclosed herein comprise at least one amino acid sequence that is chosen from the group consisting of the CDR1 sequences, CDR2 sequences and CDR3 sequences that are described herein. In some embodiments, the $V_{HH}$'s as disclosed herein may comprise at least one antigen binding site, wherein said antigen binding site comprises at least one combination of a CDR1 sequence, a CDR2 sequence and a CDR3 sequence that are described herein.

Any $V_{HH}$ or fragment thereof as disclosed herein and having one of these CDR sequence combinations is preferably able to specifically bind (as defined herein) to a tumor-specific antigen and/or to a cancer-cell-specific antigen. In some embodiments, the $V_{HH}$ or fragment thereof specifically binds to a tumor-specific antigen and/or to a cancer-cell-specific antigen with dissociation constant ($K_D$) of $10^{-8}$ M or less of said variable domain in solution. In particular embodiments, a $V_{HH}$ or fragment thereof against HER2 as disclosed herein is such that it can specifically bind to HER2 with a dissociation constant ($K_D$) of less than 5 nM, such as between 1 to 5 nM, preferably between 2 and 3 nM.

Specific binding of a $V_{HH}$ to a tumor antigen or cancer cell antigen can be determined in any suitable manner known, including, for example biopanning, Scatchard analysis and/or competitive binding assays, such as radioimmunoassays (RIA), enzyme immunoassays (EIA) and sandwich competition assays, and the different variants thereof known in the art.

In further particular embodiments, the $V_{HH}$ or fragment thereof as disclosed herein comprises at least one combination of CDR sequences chosen from the group comprising:

a CDR1 region having SEQ ID NO: 1, a CDR2 region having has SEQ ID NO: 2, and a CDR3 region having SEQ ID NO: 3, and/or a CDR1 region having SEQ ID NO: 4, a CDR2 region having has SEQ ID NO: 5, and a CDR3 region having SEQ ID NO: 6.

Thus, in particular embodiments, the present disclosure provides heavy chain variable domains derived from heavy chain antibodies with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and are as further defined herein.

SEQ ID NOs: 7 and 8 (see Table 1) give the amino acid sequences of exemplary heavy chain variable domains that have been raised against HER2.

TABLE 1

| | | VHH sequences |
|---|---|---|
| Name | SEQ ID | VHH Amino acid sequence |
| 2Rs15d | 7 | QVQLQESGGGSVQAGGSLKLTCAASGYIFNSCGMGWYR QSPGRERELVSRISGDGDTWHKESVKGRFTISQDNVKK TLYLQMNSLKPEDTAVYFCAVCYNLETYWGQGTQVTVS S |
| 2Rb17c | 8 | QVQLQESGGGLVQPGGSLRLSCAASGFIFSNDAMTWVR QAPGKGLEWVSSINWSGTHTNYADSVKGRFTISRDNAK RTLYLQMNSLKDEDTALYYCVTGYGVTKTPTGQGTQVT VSS |

In some embodiments, the disclosure provides a radiolabelled $V_{HH}$ or fragment thereof directed against a tumor-specific or cancer cell-specific target antigen, which has at least 80%, at least 85%, such as 90% or 95% or more, sequence identity with at least one of the heavy chain variable domains of SEQ ID NOs: 7 or 8 (see Table 1), or functional fragments thereof. In some embodiments, a radiolabelled $V_{HH}$ or fragment thereof directed against a tumor-specific or cancer cell-specific target antigen is encoded by a nucleic acid that which has at least 80%, at least 85%, such as 90% or 95%, or more sequence identity with a nucleic acid sequence that encodes such heavy chain variable domains or functional fragments thereof.

In some embodiments, heavy chain variable domain sequences as disclosed herein are those which can bind to and/or are directed against HER2 and which have at least 90% amino acid identity with at least one of the heavy chain variable domains of SEQ ID NOs: 7 or 8 (see Table 1), in which for the purposes of determining the degree of amino acid identity, the amino acid residues that form the CDR sequences are disregarded.

In these exemplary heavy chain variable domains of SEQ ID NOs: 7 or 8, the CDR sequences (see Table 2) are generally as further defined herein.

TABLE 2

Specific combinations of CDR sequences (CDR sequences identified using IMGT numbering)

| Name | CDR1 sequence | SEQ ID | CDR2 sequence | SEQ ID | CDR3 sequence | SEQ ID |
|---|---|---|---|---|---|---|
| 2Rs15d | GYIFNSCG | 1 | ISGDGDT | 2 | AVCYNLETY | 3 |
| 2Rb17c | GFIFSNDA | 4 | INWSGTHT | 5 | VTGYGVTKTP | 6 |

It should be noted that the disclosure is not limited as to the origin of the $V_{HH}$ or fragment thereof disclosed herein (or of the nucleotide sequences to express these), nor as to the way that the $V_{HH}$ or fragment thereof or nucleotide sequences disclosed herein are (or have been) generated or obtained. Thus, the $V_{HH}$ or fragment thereof disclosed herein may be naturally occurring amino acid sequences (from any suitable species) or synthetic or semi-synthetic amino acid sequences. In a specific but non-limiting aspect of the disclosure, the amino acid sequence is a naturally occurring immunoglobulin sequence (from any suitable species) or a synthetic or semi-synthetic immunoglobulin sequence, including but not limited to "humanized" immunoglobulin sequences (such as partially or fully humanized mouse or rabbit immunoglobulin sequences, and in particular partially or fully humanized $V_{HH}$ sequences), "camelized" immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing. Also, a $V_{HH}$ or fragment thereof as disclosed herein may be suitably humanized, as further described herein, so as to provide one or more further (partially or fully) humanized amino acid sequences of the disclosure. Similarly, when an amino acid sequence comprises a synthetic or semi-synthetic sequence (such as a partially humanized sequence), said sequence may optionally be further suitably humanized, again as described herein, so as to provide one or more further (partially or fully) humanized amino acid sequences as disclosed herein.

In some embodiments, humanized amino acid sequences may be amino acid sequences in which at least one amino acid residue is present (and in particular, in at least one of the framework residues) that is and/or that corresponds to a humanizing substitution. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences or functional fragments thereof can be tested for affinity for the target, for stability, for ease and level of expression, and/or for other desired properties. In this way, by means of a limited degree of trial and error, other suitable humanizing substitutions (or suitable combinations thereof) can be determined by the skilled artisan.

In some embodiments, the $V_{HH}$ or functional fragment thereof, when linked to a radioisotope as described herein, is capable of killing a tumor cell or a cancer cell that expresses the antigen against which the $V_{HH}$ or functional fragment thereof as disclosed herein is directed against, or can reduce or slow the growth and/or proliferation of such a tumor cell or cancer cell.

In some embodiments, a $V_{HH}$ or functional fragment thereof as described herein is radiolabelled, such as with a radiolabel that is both a β-emitter and γ-emitter. Examples of suitable radioisotopes that are both β-emitters and γ-emitters which can be linked to a $V_{HH}$ or functional fragment thereof as disclosed herein include, for example, Iodine-131, Lutetium-177, Yttrium-90, Copper-67, Rhenium-186, and Rhenium-188. In some embodiments, the radiolabelled $V_{HH}$ or functional fragment thereof as disclosed herein is labelled with Iodine-131.

In some embodiments, the radiolabelled $V_{HH}$ domains or functional fragments thereof as disclosed herein may be optionally linked to one or more further groups, moieties, or residues via one or more linkers. These one or more further groups, moieties or residues can serve for binding to other targets of interest. It should be clear that such further groups, residues, moieties and/or binding sites may or may not provide further functionality to the heavy chain variable domains as disclosed herein and may or may not modify the properties of the heavy chain variable domain as disclosed herein. Such groups, residues, moieties or binding units may also for example be chemical groups which can be biologically active.

These groups, moieties or residues are, in some embodiments, linked N- or C-terminally to the heavy chain variable domain, in particularly C-terminally linked.

In some embodiments, the radiolabelled $V_{HH}$ domains or functional fragments thereof as disclosed herein may also be chemically modified. For example, such a modification may involve the introduction or linkage of one or more functional groups, residues or moieties into or onto the heavy chain variable domain. These groups, residues or moieties may confer one or more desired properties or functionalities to the heavy chain variable domain. Examples of such functional groups will be clear to the skilled person.

For example, the introduction or linkage of such functional groups to a heavy chain variable domain can result in an increase in the solubility and/or the stability of the heavy chain variable domain, in a reduction of the toxicity of the heavy chain variable domain, or in the elimination or attenuation of any undesirable side effects of the heavy chain variable domain, and/or in other advantageous properties.

In particular embodiments, the one or more groups, residues, moieties are linked to the heavy chain variable domain via one or more suitable linkers or spacers.

In some embodiments, the one or more groups, residues or moieties do not confer to the radiolabelled $V_{HH}$ or functional fragments thereof as disclosed herein an extended half-life. Accordingly, in some embodiments, the radiolabelled $V_{HH}$ or functional fragments thereof as disclosed herein are non-lifetime extended.

In some embodiments, the one or more groups, residues or moieties do not induce multimerization such as dimerization of the radiolabelled $V_{HH}$ or functional fragments thereof as disclosed herein. For example, $V_{HH}$s containing a carboxy-terminal cysteine-containing tag such as a GCC-tag result in an equilibrium mixture of monomeric and dimeric forms (Pruszyski et al. 2013 Nucl Med Biol. 40:52-59). Accordingly, in particular embodiments, the radio-labelled $V_{HH}$ or functional fragments thereof as disclosed herein are devoid of a tag that induces multimerization such as dimerization, more particularly a cysteine-containing tag, even more particularly a GGC-tag.

In some embodiments, the radiolabelled $V_{HH}$ or functional fragment thereof as disclosed herein is devoid of a C-terminal polypeptide tag such as a His-tag and/or a Myc-tag. In some embodiments, the radiolabelled $V_{HH}$ or functional fragment thereof as disclosed herein is untagged. As described herein, kidney retention was shown to be significantly reduced when using $V_{HH}$s without a carboxy-terminal polypeptide tag compared to polypeptide tagged, such as His-tagged and Myc-His-tagged, $V_{HH}$s.

While the radiolabelled $V_{HH}$ domains specifically binding to a tumor-specific antigen and/or a cancer cell-specific antigen as disclosed herein are generally in monomeric form (as further described herein), in particular alternative embodiments, two or more of the radiolabelled $V_{HH}$s or functional fragments thereof as disclosed herein may be linked to each other or may be interconnected. In particular embodiments, the two or more $V_{HH}$s or functional fragments thereof are linked to each other via one or more suitable linkers or spacers. Suitable spacers or linkers for use in the coupling of different $V_{HH}$s as disclosed herein will be clear to the skilled person and may generally be any linker or spacer used in the art to link peptides and/or proteins.

Some exemplary suitable linkers or spacers include, but are not limited to, polypeptide linkers such as glycine linkers, serine linkers, mixed glycine/serine linkers, glycine- and serine-rich linkers or linkers composed of largely polar polypeptide fragments, or homo- or heterobifunctional chemical crosslinking compounds such as glutaraldehyde or, optionally PEG-spaced, maleimides or NHS esters.

For example, a polypeptide linker or spacer may be a suitable amino acid sequence having a length between 1 and 50 amino acids, such as between 1 and 30, and in particular between 1 and 10 amino acid residues. It should be clear that the length, the degree of flexibility and/or other properties of the linker(s) may have some influence on the properties of the heavy chain variable domains, including but not limited to the affinity, specificity or avidity for the tumor target or the target on a cancer cell. It should be clear that when two or more linkers are used, these linkers may be the same or different. In the context and disclosure of the present disclosure, the person skilled in the art will be able to determine the optimal linkers for the purpose of coupling $V_{HH}$s or functional fragments thereof as disclosed herein.

IV. Functional Fragments, Analogs, Mutants, Variants, and/or Derivatives of Heavy Chain Variable Domains The present disclosure also encompasses fragments, analogs, mutants, variants, and/or derivatives of the radiolabelled $V_{HH}$ disclosed herein and/or polypeptides comprising or essentially consisting of one or more of such fragments, analogs, mutants, variants, and/or derivatives. Such fragments, analogs, mutants, variants, and/or derivatives according to the disclosure are generally functional. In some embodiments, such fragments, analogs, mutants, variants, and/or derivatives according to the disclosure are considered functional if they are still capable of specifically binding to the tumor-specific antigen and/or to the cancer cell-specific antigen.

For example, the disclosure provides a number of CDR sequences of the $V_{HH}$'s as disclosed herein, that are particularly suited for binding to a tumor antigen or cancer antigen. In some embodiments, CDR sequences may be regarded as being functional fragments of the $V_{HH}$'s as disclosed herein and may be present in, and/or may be incorporated into any suitable scaffold protein or $V_{HH}$ as disclosed herein, in particular in such a way that they form the antigen binding site, or a portion thereof, of that suitable scaffold protein or $V_{HH}$. It should however be noted that the disclosure in its broadest sense is not limited to a specific structural role or function that these CDR sequences may have in the scaffolds or $V_{HH}$'s as disclosed herein, as long as these CDR sequences allow these scaffolds or $V_{HH}$'s as disclosed herein to specifically bind to a tumor antigen or cancer antigen.

V. Nucleic Acid Sequences, Hosts, and Host Cells

In a further aspect, the present disclosure provides nucleic acid sequences encoding the antibody fragments, such as $V_{HH}$s or functional fragments thereof, as described herein. These nucleic acid sequences can be in the form of a vector or be integrated in a genome, such as the genome of a cell. The nucleic acid sequences as disclosed herein may be synthetic or semi-synthetic sequences, nucleotide sequences that have been isolated from a library (such as an expression library), nucleotide sequences that have been prepared by PCR using overlapping primers, or nucleotide sequences that have been prepared using techniques for DNA synthesis known in the art.

The nucleic acid sequences as disclosed herein may be DNA or RNA, such as double-stranded DNA. The nucleic acid sequences as disclosed herein may also be in a form suitable for transformation of a host cell or host organism in a form suitable for integration into the genomic DNA of the intended host cell or in a form suitable for independent replication, maintenance and/or inheritance in the intended host organism. For instance, the nucleic acid sequences of the disclosure may be in the form of a vector, such as for example a plasmid, cosmid, YAC, a viral vector or transposon. In some embodiments, the vector may be an expression vector, e.g., a vector that can provide for expression in vitro and/or in vivo (e.g., in a suitable host cell, host organism and/or expression system).

In still a further aspect, the disclosure provides hosts or host cells that express or are capable of expressing one or more amino acid sequences as disclosed herein. Suitable examples of hosts or host cells for expression of the $V_{HH}$ sequences, polypeptides of the disclosure will be clear to the skilled person.

VI. Polypeptides Comprising VHH Domains

In a further aspect, the present disclosure provides polypeptides that comprise or essentially consist of at least one $V_{HH}$ sequence of the present disclosure that specifically binds to a tumor-specific antigen and/or a cancer cell-specific antigen. The polypeptides of the disclosure may comprise at least one $V_{HH}$ or functional fragments thereof as disclosed herein and optionally one or more further groups, moieties, residues optionally linked via one or more linkers.

In some embodiments, the present disclosure provides polypeptides and pharmaceutical compositions comprising a $V_{HH}$ in its monomeric form, i.e. comprising only one $V_{HH}$ domain so as to minimize the in vivo half-life of said polypeptides and pharmaceutical compositions as much as possible.

In alternative embodiments, the present disclosure also provides polypeptides and pharmaceutical compositions comprising two or more identical or different $V_{HH}$ domains resulting in a bivalent (or multivalent) or a bispecific or (multispecific) polypeptide. The polypeptides as disclosed herein may at least contain one or more further groups, moieties or residues for binding to other targets or target proteins of interest. It should be clear that such further groups, residues, moieties and/or binding sites may or may not provide further functionality to the amino acid sequences as disclosed herein (and/or to the polypeptide or composition in which it is present) and may or may not modify the properties of the amino acid sequence as disclosed herein. Such groups, residues, moieties or binding units may also for example be chemical groups which can be biologically and/or pharmacologically active. These groups, moieties or residues are, in some embodiments, linked N- or C-terminally to the amino acid sequence as disclosed herein.

In some embodiments, the further groups, residues or moieties do not confer to the polypeptide an extended half-life. Accordingly, in some embodiments, the polypeptides as disclosed herein are non-lifetime extended.

In some embodiments, the further groups, residues or moieties do not induce multimerization such as dimerization of the polypeptides as disclosed herein. Accordingly, in particular embodiments, the polypeptides as disclosed herein are devoid of a tag that induces multimerization such as dimerization, more particularly a cysteine-containing tag, even more particularly a GGC-tag.

In some embodiments, the polypeptides as disclosed herein are devoid of a C-terminal polypeptide tag such as a His-tag and/or a Myc-tag. In some embodiments, the polypeptides as disclosed herein are untagged.

It should be noted that the disclosure is not limited as to the origin of the $V_{HH}$ sequences or functional fragments thereof, polypeptides or compositions of the disclosure (or of the nucleotide sequences of the disclosure used to express them). Furthermore, the present disclosure is also not limited as to the way that the $V_{HH}$ sequences, polypeptides or nucleotide sequences as disclosed herein have been generated or obtained. Thus, the amino acid sequences as disclosed herein may be synthetic or semi-synthetic amino acid sequences, polypeptides or proteins.

The amino acid sequences, polypeptides and compositions provided by the disclosure can be in essentially isolated form (as defined herein), or alternatively can form part of a polypeptide or composition as disclosed herein, which may comprise or essentially consist of at least one amino acid sequence as disclosed herein and which may optionally further comprise one or more other groups, moieties or residues (all optionally linked via one or more suitable linkers).

VII. Target Proteins

In some embodiments, $V_{HH}$ or functional fragments thereof disclosed herein are obtained by affinity selection against a particular target protein present on a solid tumor and/or a cancer cell. Obtaining suitable polypeptides by affinity selection against a particular solid tumor antigen or cancer cell may for example be performed by screening a set, collection or library of cells that express $V_{HH}$'s on their surface (e.g., bacteriophages) for binding against a tumor-specific antigen and/or a cancer cell-specific antigen. An exemplary method is provided in the following non-limiting steps: a) obtaining an isolated solution or suspension of a tumor-specific or cancer cell-specific protein target molecule, which molecule is known to be a target for a potential cancer drug; b) bio-panning phages or other cells from a $V_{HH}$ library against said protein target molecule; c) isolating the phages or other cells binding to the tumor-specific or cancer cell-specific protein target molecule; d) determining the nucleotide sequence encoding the $V_{HH}$ insert from individual binding phages or other cells; e) producing an amount of $V_{HH}$ according to this sequence using recombinant protein expression and f) determining the affinity of said $V_{HH}$ domain for said tumor-specific or cancer cell-specific protein target molecule and optionally g) testing the tumoricidal or anti-cancer activity of said $V_{HH}$ in a bio-assay. Various methods may be used to determine the affinity between a $V_{HH}$ and a tumor-specific or cancer cell-specific protein target molecule, including for example, enzyme linked immunosorbent assays (ELISA) or Surface Plasmon Resonance (SPR) assays, which are common practice in the art, for example, as described in Sambrook et al. (2001), Molecular Cloning, A Laboratory Manual. Third Edition. Cold Spring Harbor Laboratory Press, Cold Spring Harbor, N.Y. In some embodiments, the dissociation constant of the binding between the polypeptide and its target molecule is lower than $10^{-5}$ M, lower than $10^{-6}$ M, lower than $10^{-7}$ M, lower than $10^{-8}$ M, such as below $10^{-9}$ M, or below $0.5 \times 10^{-9}$ M, such as below $10^{-10}$ M.

In particular embodiments, the $V_{HH}$ as disclosed herein specifically binds to a tumor antigen (e.g., HER2) with a dissociation constant of less than $5 \times 10^{-9}$ M, such as between about $1 \times 10^{-9}$ M and about $5 \times 10^{-9}$ M, such as between about $2 \times 10^{-9}$ M and about $3 \times 10^{-9}$ M.

In some embodiments, tumor-specific antigens or cancer cell-specific antigens are molecules occurring specifically or being expressed specifically and/or abundantly on the surface of tumor cells or cancer cells, respectively, and, in some embodiments, not or only in relatively low concentration or density on the surface of normal healthy cells. In some embodiments, when these tumor-specific or cancer cell-specific antigens are bound to the radiolabelled $V_{HH}$'s or functional fragments as disclosed herein, the corresponding tumor or cancer cells onto which the antigens are expressed are killed or at least arrested, inhibited or reduced in their growth through the mechanism of radiotoxicity.

Suitable tumor-specific or cancer cell-specific target molecules are readily available from existing literature or patent databases for the skilled person and include, without limitation any protein produced in a tumor cell that has an abnormal structure due to mutation, including the abnormal products of ras and p53 genes, tissue differentiation antigens, mutant protein antigens, oncogenic viral antigens, cancer-testis antigens, oncofetal antigens and vascular or stromal specific antigens. Examples of specific tumor antigens include but are not limited to CTAG1B, MAGEA1, the enzyme tyrosinase, alphafetoprotein (AFP), carcinoembryonic antigen (CEA), EBV and HPV, abnormally structured cell surface glycolipids and glycoproteins and HER2, EGFR and variants thereof.

In some embodiments, the radiolabelled $V_{HH}$ or functional fragment as disclosed herein specifically binds to HER2. In some embodiments, the radiolabelled $V_{HH}$ or functional fragment as disclosed herein specifically binds to HER2 and is for use in a method described herein.

In certain non-limiting embodiments, the radiolabelled $V_{HH}$ or functional fragment thereof specifically binds to a binding site on HER2, which is different from the Trastuzumab (Herceptin®) binding site on HER2 and/or does not compete with Herceptin® for binding to HER2, as determined using a suitable competition assay.

In some embodiments, the radiolabelled $V_{HH}$ or functional fragment thereof specifically binds to a binding site on HER2, which is different from (i.e. is not) domain IV of HER2. In some embodiments, the radiolabelled $V_{HH}$ or functional fragment thereof specifically binds to a binding site on HER2, which is different from (i.e. is not) the C-terminus of domain IV of HER2.

In some embodiments, the radiolabelled $V_{HH}$ or functional fragment thereof does not compete with the monoclonal antibody Trastuzumab (Herceptin®) for binding to HER2, as determined using a suitable competition assay.

In some embodiments, the radiolabelled $V_{HH}$ or functional fragment thereof specifically binds to a binding site on HER2, which is different from the Perjeta® (Pertuzumab) binding site on HER2. In some embodiments, the radiolabelled $V_{HH}$ or functional fragment thereof specifically binds to a binding site on HER2, which is different from (i.e. is not) domain II of HER2.

In some embodiments, the radiolabelled $V_{HH}$ or functional fragment thereof does not compete with the monoclonal antibody Pertuzumab (Perjeta®) for binding to HER2, as determined using a suitable competition assay.

In some embodiments, the radiolabelled $V_{HH}$ or functional fragment thereof does not compete with the monoclonal antibody Trastuzumab (Herceptin®) and the monoclonal antibody Pertuzumab (Perjeta®) for binding to HER2, as determined using a suitable competition assay. In further embodiments, the radiolabelled $V_{HH}$ or functional fragment thereof specifically binds to a binding site on HER2, which is different from the Trastuzumab (Herceptin®) and Pertuzumab (Perjeta®) binding site on HER2. In some embodiments, the radiolabelled $V_{HH}$ or functional fragment thereof specifically binds to a binding site on HER2, which is different from (i.e. is not) domain IV of HER2, such as the C-terminus of domain IV of HER2, and domain II of HER2.

A suitable competition assay for determining whether or not an antigen-targeting (e.g. HER2-targeting) radiolabelled $V_{HH}$ or a functional fragment thereof competes with a binding agent, such as a monoclonal antibody, targeting the same antigen may be, for example but without limitation, an in vivo competition assay. In an in vivo competition assay, the biodistribution of the radiolabelled $V_{HH}$ or the functional fragment thereof is compared in a test animal that was administered the radiolabelled $V_{HH}$ or the functional fragment thereof alone and a test animal that was pre-treated with the binding agent prior to administration of the radiolabelled $V_{HH}$ or the functional fragment thereof, wherein substantially the same biodistribution profile indicates that the radiolabelled $V_{HH}$ or the functional fragment thereof does not compete with the binding agent for binding to the target antigen.

It will be appreciated based on the disclosure herein that, in some embodiments, the $V_{HH}$'s or functional fragments thereof, polypeptides and compositions as disclosed herein will in principle specifically bind to all forms of the tumor-specific antigen and/or a cancer cell-specific antigen. However, where the $V_{HH}$ or functional fragment thereof, polypeptide or composition as disclosed herein are intended for veterinary purposes, they will generally specifically bind to all forms of the tumor-specific antigen and/or a cancer cell-specific antigen from the species intended to be treated, or they will be at least cross-reactive with all forms of the tumor-specific antigen and/or a cancer cell-specific antigen from the species to be treated. Accordingly, $V_{HH}$'s or functional fragments thereof, polypeptides and compositions that specifically bind to all forms of the antigen from one subject species may or may not show cross-reactivity with all forms of the antigen from one or more other subject species. In some embodiments, in the context of the development of amino acid sequences for use in humans or animals, $V_{HH}$ sequences may be developed which bind to forms of the tumor-specific antigen and/or a cancer cell-specific antigen from another species than that which is to be treated for use in research and laboratory testing.

In some embodiments, it is also expected that the $V_{HH}$'s or functional fragments thereof, polypeptides and compositions of the disclosure will bind to a number of naturally occurring or synthetic analogs, variants, mutants, alleles, parts or fragments of the tumor-specific antigen and/or cancer cell-specific antigen. In some embodiments, it is expected that the $V_{HH}$'s or functional fragments thereof, polypeptides and compositions of the disclosure will bind at least to those analogs, variants, mutants, alleles, parts or fragments of the tumor-specific antigen and/or cancer cell-specific antigen that contain the binding site or a domain of the antigen to which those $V_{HH}$'s or functional fragments thereof, polypeptides and compositions bind.

In particular embodiments, where the disclosure provides $V_{HH}$'s or functional fragments thereof that specifically bind to HER2, it is within the scope of the disclosure that the VHH's as disclosed herein can only bind to HER2 in monomeric form, or can only bind to HER2 in multimeric form, or can bind to both the monomeric and the multimeric form of HER2. In some embodiments, the $V_{HH}$'s or functional fragments thereof as disclosed herein may bind to the monomeric form of HER2 with an affinity and/or specificity that are the same as, or that are different from (i.e. higher than or lower than), the affinity and specificity with which the $V_{HH}$'s as disclosed herein bind to the multimeric form.

In some embodiments, when HER2 can associate with other proteins or polypeptides (e.g. with other ERBB receptors, also referred to as heterodimerization) to form protein complexes (e.g. with multiple subunits), it is within the scope of the disclosure that the $V_{HH}$'s as disclosed herein can bind to HER2 in its non-associated state, or can bind HER2 in its associated state, or can bind to both.

In some embodiments, $V_{HH}$ sequences as disclosed herein will at least bind to those forms of HER2 (including monomeric, multimeric and associated forms) that are the most relevant from a biological and/or therapeutic point of view, as will be clear to the skilled person.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

VIII. Production and Manufacturing of Antibody Fragments and Pharmaceutical Compositions The disclosure further provides methods for preparing or generating an antibody fragment as described herein, such as a $V_{HH}$ or functional fragment thereof. The disclosure also provides methods for producing nucleic acids encoding an antibody fragment as described herein, such as a $V_{HH}$ or functional fragment thereof, as well as host cells, products and compositions comprising these an antibody fragment as described herein, such as a $V_{HH}$ or functional fragment thereof. Some non-limiting examples of such methods are described herein.

As will be clear to the skilled person, one exemplary method for preparing heavy chain variable domain sequences as disclosed herein generally comprises the steps of:
- (a) expressing a nucleotide sequence encoding a heavy chain variable domain sequence as disclosed herein or a vector or genetic construct a nucleotide sequence encoding that heavy chain variable domain sequence and
- (b) optionally isolating and/or purifying the heavy chain variable domain sequence.

In particular embodiments envisaged herein, the tumor-specific or cancer cell-specific a heavy chain variable domain sequences can be obtained by methods which involve generating a random library of $V_{HH}$ sequences and screening this library for an $V_{HH}$ sequence capable of specifically binding to a tumor-specific or cancer cell-specific target protein.

In some embodiments, methods for preparing a heavy chain variable domain sequence as disclosed herein comprise the steps of:
- a) providing a set, collection or library of amino acid sequences of $V_{HH}$ domains; and
- b) screening said set, collection or library of amino acid sequences for amino acid sequences that can bind to and/or have affinity for the tumor-specific or cancer cell-specific target.

and
- c) isolating the amino acid sequence(s) that can bind to and/or have affinity for the tumor-specific or cancer cell-specific target.

In such a method, the set, collection or library of $V_{HH}$ sequences may be any suitable set, collection or library of amino acid sequences. For example, the set, collection or library of amino acid sequences may be a set, collection or library of immunoglobulin fragment sequences (as described herein), such as a naïve set, collection or library of immunoglobulin fragment sequences; a synthetic or semi-synthetic set, collection or library of immunoglobulin fragment sequences; and/or a set, collection or library of immunoglobulin fragment sequences that have been subjected to affinity maturation.

In particular embodiments of this method, the set, collection or library of $V_{HH}$ sequences may be an immune set, collection or library of immunoglobulin fragment sequences, for example derived from a mammal that has been suitably immunized with a tumor-specific or cancer cell-specific target or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In some embodiments of the above methods, the set, collection or library of $V_{HH}$ sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art, for example on the basis of the further disclosure herein. Reference is also made to the review by Hoogenboom in Nature Biotechnology, 23, 9, 1105-1116 (2005).

In other embodiments, the methods for generating the heavy chain variable domain sequences as disclosed herein comprise at least the steps of:
- a) providing a collection or sample of cells expressing $V_{HH}$ domain amino acid sequences;
- b) screening said collection or sample of cells for cells that express an amino acid sequence that can bind to and/or have affinity for a tumor-specific or cancer cell-specific target;

and
- c) either (i) isolating said amino acid sequence; or (ii) isolating from said cell a nucleic acid sequence that encodes said amino acid sequence, followed by expressing said amino acid sequence.

The collection or sample of cells may, for example, be a collection or sample of B-cells. In some embodiments, in this method, the sample of cells may be derived from a mammal that has been suitably immunized with a tumor-specific or cancer cell-specific target or with a suitable antigenic determinant based thereon or derived therefrom, such as an antigenic part, fragment, region, domain, loop or other epitope thereof. In one particular embodiment, the antigenic determinant may be an extracellular part, region, domain, loop or other extracellular epitope(s).

In other embodiments, the method for generating a heavy chain variable domain sequence directed against a tumor-specific or cancer cell-specific target may comprise at least the steps of:
- a) providing a set, collection or library of nucleic acid sequences encoding a $V_{HH}$ domain amino acid sequence;
- b) screening said set, collection or library of nucleic acid sequences for nucleic acid sequences that encode an amino acid sequence that can bind to and/or has affinity for the tumor-specific or cancer cell-specific target;

and
- c) isolating said nucleic acid sequence, followed by expressing said amino acid sequence.

In some embodiments of the above methods, the set, collection or library of nucleic acid sequences encoding amino acid sequences may for example be a set, collection or library of nucleic acid sequences encoding a naïve set, collection or library of immunoglobulin fragment sequences; a set, collection or library of nucleic acid sequences encoding a synthetic or semi-synthetic set, collection or library of immunoglobulin fragment sequences; and/or a set, collection or library of nucleic acid sequences encoding a set, collection or library of immunoglobulin fragment sequences that have been subjected to affinity maturation.

In some embodiments, in such a method, the set, collection or library of nucleic acid sequences encodes a set, collection or library of $V_{HH}$ domains directed against a tumor-specific or cancer cell-specific antigen (as defined herein).

In some embodiments of the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to the review by Hoogenboom in Nature Biotechnology, 23, 9, 1105-1116 (2005).

The disclosure therefore provides $V_{HH}$ and functional fragments thereof that are obtainable or obtained by any of the above methods, or alternatively by a method that comprises one of the above methods and in addition at least the steps of determining the nucleotide sequence or amino acid sequence of said $V_{HH}$ sequence; and of expressing or synthesizing said $V_{HH}$ sequence in a manner known in the art, such as by expression in a suitable host cell or host organism or by chemical synthesis.

In some embodiments, the methods for producing the antibody fragments, such as $V_{HH}$ and functional fragments, as described herein may further comprise the step of isolating from the amino acid sequence library at least one $V_{HH}$ having detectable binding affinity for a tumor-specific or cancer cell-specific target.

In some embodiments, the methods may further comprise the step of amplifying a sequence encoding at least one $V_{HH}$ or functional fragment thereof having detectable binding affinity for a tumor-specific or cancer cell-specific target. For example, a phage clone displaying a particular amino acid sequence, obtained from a selection step of a method described herein, may be amplified by reinfection of a host bacteria and incubation in a growth medium.

In some embodiments, the methods may encompass determining the sequence of the one or more amino acid sequences capable of binding to a tumor-specific or cancer cell-specific target.

Where a heavy chain variable domain sequence, comprised in a set, collection or library of amino acid sequences, is displayed on a suitable cell or phage or particle, it is possible to isolate from said cell or phage or particle, the nucleotide sequence that encodes that amino acid sequence. In this way, the nucleotide sequence of the selected amino acid sequence library member(s) can be determined by a routine sequencing method.

In further particular embodiments, the methods for producing a $V_{HH}$ or functional fragment thereof as envisaged herein comprise the step of expressing said nucleotide sequence(s) in a host organism under suitable conditions, so as to obtain the desired amino acid sequence. This step can be performed by methods known to the person skilled in the art.

In addition, the obtained $V_{HH}$ or functional fragment having detectable binding affinity for a tumor-specific or cancer cell-specific target, may be synthesized as a soluble protein construct, optionally after their sequence has been identified.

For instance, the $V_{HH}$ or functional fragment obtained, obtainable or selected by the above methods can be synthesized using recombinant or chemical synthesis methods known in the art. Also, the amino acid sequences obtained, obtainable or selected by the above methods can be produced by genetic engineering techniques. Thus, in some embodiments, methods for synthesizing the $V_{HH}$ or functional fragment obtained, obtainable or selected by the above methods may comprise transforming or infecting a host cell with a nucleic acid or a vector encoding an amino acid sequence having detectable binding affinity for a tumor-specific or cancer cell-specific target. Accordingly, the $V_{HH}$ sequences having detectable binding affinity for a tumor-specific or cancer cell-specific target can be made by recombinant DNA methods. DNA encoding the amino acid sequences can be readily synthesized using conventional procedures. Once prepared, the DNA can be introduced into expression vectors, which can then be transformed or transfected into host cells such as *E. coli* or any suitable expression system, in order to obtain the expression of amino acid sequences in the recombinant host cells and/or in the medium in which these recombinant host cells reside.

In some embodiments, the $V_{HH}$ or functional fragment produced from an expression vector using a suitable expression system may be tagged (typically at the N-terminal or C-terminal end of the amino acid sequence) with e.g., a His-tag or other sequence tag for easy purification.

Transformation or transfection of nucleic acids or vectors into host cells may be accomplished by a variety of means known to the person skilled in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Suitable host cells for the expression of the desired $V_{HH}$ or functional fragment thereof may be any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic plant or animal.

Thus, the disclosure also provides methods for the production of a $V_{HH}$ or functional fragment thereof having detectable binding affinity for a tumor- or cancer cell-specific antigen comprising transforming, transfecting or infecting a host cell with nucleic acid sequences or vectors encoding such $V_{HH}$ or functional fragment sequences and expressing their amino acid sequences under suitable conditions.

In some embodiments, the disclosure further provides methods for the manufacture or the production of a pharmaceutical composition as disclosed herein.

In particular embodiments, the disclosure provides methods for producing a pharmaceutical composition as disclosed herein, at least comprising the steps of:
  obtaining at least one $V_{HH}$ or a functional fragment thereof, which specifically binds to a tumor or cancer cell-specific antigen, and
  formulating said $V_{HH}$ or functional fragment thereof in a pharmaceutical composition.

In particular embodiments of these methods, the step of obtaining at least one $V_{HH}$ or a functional fragment thereof, which specifically binds to a tumor-specific or cancer cell-specific antigen comprises:
  (a) expressing a nucleotide sequence encoding a $V_{HH}$ or functional fragment thereof, which specifically binds to a tumor-specific or cancer cell-specific antigen, and optionally
  (b) isolating and/or purifying the $V_{HH}$ or functional fragment thereof.

In other particular embodiments of these methods, the step of obtaining at least one $V_{HH}$ or functional fragment thereof, which specifically binds to a tumor-specific or cancer cell-specific protein target comprises:
  (a) providing a set, collection or library of $V_{HH}$ domain sequences or functional fragments of $V_{HH}$ sequences;
  (b) screening said set, collection or library of $V_{HH}$ domain sequences or sequences of functional fragments thereof for sequences that specifically bind to and/or have affinity for a tumor antigen, and optionally
  (c) isolating the $V_{HH}$ sequences or sequences of functional fragments thereof that specifically bind to and/or have affinity for a tumor-specific or cancer cell-specific antigen.

IX. Radiolabelling of Antibody Fragments

In some embodiments, the antibody fragments, such as $V_{HH}$'s or functional fragments thereof, as disclosed herein are linked to or coupled to, such as chemically coupled to, a radionuclides (also referred to herein as radioisotopes). In some embodiments, the radionuclide is both a β-emitter and γ-emitter. Examples of suitable radioisotopes that are both β-emitters and γ-emitters which can be linked to a $V_{HH}$ or functional fragment thereof as disclosed herein include, for example, Iodine-131, Lutetium-177, Yttrium-90, Copper-67, Rhenium-186, and Rhenium-188. In some embodiments, the radiolabelled $V_{HH}$ or functional fragment thereof as disclosed herein is labelled with Iodine-131.

There are various radiolabeling strategies available to incorporate a radionuclide into a protein, such as a $V_{HH}$ or functional fragment thereof. The choice of technique for a radiochemist depends primarily on the radionuclide used. The radioactive isotopes of iodine possess the ability to be directly integrated into a molecule by electrophilic substitution or indirectly via conjugation. Radioactive metals on the other hand may be labeled via complexation with a chelating agent. Many metallic radionuclides possess the ability to form stable complexes with chelating agents, thus allowing for conjugation with a protein, such as a $V_{HH}$ or functional fragment thereof.

Generally there are two basic approaches of protein radioiodination. One approach is direct protein labeling using electrophilic substitution at tyrosine and histidine residues. The radioiodide is oxidized in situ creating the electrophile *I$^+$. This is done using oxidizing agents like chloramine T, Iodogen® and N-halosuccinimides. The generated electrophile attacks the electron rich of aromatic ring of the amino acid tyrosine, forming a σ-complex. This substitution is performed at the tyrosine residue due to the electron donating hydroxyl group which stabilizes the σ-complex. As the labeling of proteins must take place under mild conditions, the attachment of iodine to the tyrosine is suitable. This method is performed under mild conditions, which is optimal for the labeling of proteins. This is however only possible when the protein contains accessible tyrosine or histidine residues.

Indirect iodination of proteins via conjugation, such as using a linker, is an alternative method. In this approach iodine is incorporated by the application of prosthetic groups containing two functional groups to enable both radioiodination and incorporation in the protein. There are a variety of prosthetic groups used for radioiodination, such as N-succinimidyl 5-[* 1]iodo-3-pyridinecarboxyl ([$^{131}$I]SIPC) and N-succinimidyl-3-[*I]-iodobenzoate ([*I]SIB). Both active esters are conjugated to amino groups of the protein and exhibit a high in vivo stability. Another exemplary prosthetic group for the acylation of aromatic groups is N-succinimidyl-4-guanidinomethyl-3-[I-131]iodobenzbate ([I-131]SG-MIB).

In some embodiments, the radiolabelled $V_{HH}$'s or functional fragments thereof as disclosed herein are labelled with Iodine-131 using N-succinimidyl-4-guanidinomethyl-3-[I-131]iodobenzbate ([I-131]SGMIB) or suitable derivatives or variants thereof.

Detailed protocols for radiotherapy are readily available to the skilled artisan (see, e.g., Cancer Radiotherapy: Methods and Protocols (Methods in Molecular Medicine), Huddart RA Ed., Human Press 2002).

X. KITS

In some aspects, the disclosure provides kits, such as a kit for carrying out a method as described herein. In some embodiments, the kit comprises a screening dose of a radiolabelled antibody fragment as described herein (e.g., a radiolabelled $V_{HH}$, or functional fragment thereof), and a therapeutic dose of the radiolabelled antibody fragment. Screening doses and therapeutic doses are described herein. In some embodiments of any one of the kits, the antibody fragment is radiolabelled with a radioisotope that is both a γ-emitter and β-emitter (e.g., Iodine-131). Suitable radioisotopes are described herein.

In some embodiments of any one of the kits, the kit further comprises one or more means for injection of the screening dose and the therapeutic dose. In some embodiments, the screening dose and therapeutic dose are each individually housed in a means for injection. In some embodiments, the means for injection is a syringe. In some embodiments of any one of the kits, the kit further comprises instructions for carrying out a method as described herein (e.g., a method of stratifying and treating a subject as described herein). The instructions may be in any suitable form, e.g., in printed form (e.g., as a paper or laminated insert or label) or in electronic form (e.g., on a disc or USB stick).

XI. Other Exemplary Aspects

Other non-limiting aspects of the disclosure are provided below.

Aspect 1: A radiolabelled, heavy chain variable domain derived from a heavy chain antibody ($V_{HH}$), or a functional fragment thereof, which specifically binds to a target protein that is present on a cancer cell or solid tumor for use in the treatment of cancer, wherein a subject having cancer is selected for treatment on the basis of detection in the subject of a screening dose of the radiolabeled $V_{HH}$, or functional fragment thereof and wherein the radiolabelled $V_{HH}$, or functional fragment thereof is subsequently administered at a "therapeutic dose" to the selected subject, and wherein the $V_{HH}$, or functional fragment thereof, is radiolabelled with a radioisotope that is both a γ-emitter and β-emitter.

Aspect 2: The radiolabelled $V_{HH}$, or functional fragment thereof for use according to aspect 1, wherein the radiolabelled $V_{HH}$, or functional fragment thereof is administered at the screening dose to the subject and detected at a tumor site in the subject prior to selecting the subject.

Aspect 3: The radiolabelled $V_{HH}$, or functional fragment thereof for use according to aspect 2, wherein the detection of the radiolabelled $V_{HH}$, or functional fragment thereof comprises imaging the subject.

Aspect 4: The radiolabelled $V_{HH}$, or functional fragment thereof for use according to aspect 3, wherein the imaging is gamma camera imaging such as planar gamma camera imaging, single photon emission computed tomography or positron emission tomography, optionally combined with a non-nuclear imaging technique such as X-ray imaging, computed tomography and/or magnetic resonance imaging.

Aspect 5: The radiolabelled $V_{HH}$, or functional fragment thereof for use according to any one of aspects 1 to 4, wherein the radioisotope is Iodine-131, Lutetium-177, Yttrium-90, Copper-67, Rhenium-186, or Rhenium-188.

Aspect 6: The radiolabelled $V_{HH}$, or functional fragment thereof for use according to any one of aspects 1 to 5, wherein the radioisotope is attached to the $V_{HH}$, or functional fragment thereof, via a linker.

Aspect 7: The radiolabelled $V_{HH}$, or functional fragment thereof for use according to any one of aspects 1 to 6, wherein the $V_{HH}$, or functional fragment thereof, is radiolabelled with Iodine-131 using N-succinimidyl-4-guanidinomethyl-3-[I-131]iodobenzbate ([I-131]-SGMIB) or a suitable derivative or variant thereof.

Aspect 8: The radiolabelled $V_{HH}$, or functional fragment thereof for use according to any one of aspects 1 to 7, wherein the screening dose is between 37 MBq and 370 MBq and the therapeutic dose is between 370 MBq and 18500 MBq.

Aspect 9: The radiolabelled $V_{HH}$, or functional fragment thereof for use according to any one of aspects 1 to 7, wherein the radiolabelled $V_{HH}$, or functional fragment thereof, specifically binds to HER2.

Aspect 10: The radiolabelled $V_{HH}$, or functional fragment thereof for use according to aspect 9, wherein the radiolabelled $V_{HH}$, or functional fragment thereof, does not compete with the monoclonal antibody Trastuzumab (Herceptin®) or the monoclonal antibody Pertuzumab (Perjeta®) for binding to HER2, as determined using a competition assay.

Aspect 11: The radiolabelled $V_{HH}$, or functional fragment thereof for use according to aspect 9 or 10, wherein the radiolabelled $V_{HH}$, or a functional fragment thereof, comprises one of the CDR combinations chosen from the group comprising:
a CDR1 region having SEQ ID NO:1, a CDR2 region having SEQ ID NO:2, and a CDR3 region having SEQ ID NO:3, and
a CDR1 region having SEQ ID NO:4, a CDR2 region having SEQ ID NO:5, and a CDR3 region having SEQ ID NO:6.

Aspect 12: The radiolabelled $V_{HH}$, or functional fragment thereof for use according to any one of aspects 9 to 11, wherein the radiolabelled $V_{HH}$, or the functional fragment thereof, has at least 80% amino acid identity with at least one of the amino acid sequences of SEQ ID NOs:7 and 8.

Aspect 13: The radiolabelled $V_{HH}$, or functional fragment thereof for use according to aspect 12, wherein the radiolabelled $V_{HH}$, or the functional fragment thereof, is identical with at least one of the amino acid sequences of SEQ ID NOs: 7 and 8.

Aspect 14: The radiolabelled $V_{HH}$, or functional fragment thereof for use according to any one of aspects 1 to 13, wherein the screening dose and the therapeutic dose of the radiolabelled $V_{HH}$, or functional fragment thereof, are each independently administered to the subject intravenously, intraperitoneally, or intrathecally.

Aspect 15: The radiolabelled $V_{HH}$, or functional fragment thereof for use according to any one of aspects 1 to 14, wherein the radiolabelled $V_{HH}$, or functional fragment thereof, is present in a monovalent format.

Aspect 16: The radiolabelled $V_{HH}$, or functional fragment thereof for use according to any one of aspects 1 to 15, wherein the radiolabelled $V_{HH}$, or functional fragment thereof, is devoid of a cysteine-containing tag, preferably a GGC-tag.

Aspect 17: The radiolabelled $V_{HH}$, or functional fragment thereof for use according to any one of aspects 1 to 16, wherein the radiolabelled $V_{HH}$, or functional fragment thereof, is non-lifetime extended.

Aspect 18: The radiolabelled $V_{HH}$, or functional fragment thereof for use according to any one of aspects 1 to 17, wherein the radiolabelled $V_{HH}$, or functional fragment thereof, is untagged.

Aspect 19: The radiolabelled $V_{HH}$, or functional fragment thereof for use according to any one of aspects 1 to 18, wherein the cancer is a solid tumor.

Aspect 20: The radiolabelled $V_{HH}$, or functional fragment thereof for use according to any one of aspects 1 to 18, wherein the cancer is a hematological cancer.

Aspect 21: The radiolabelled $V_{HH}$, or functional fragment thereof for use according to any one of aspects 1 to 18, wherein the cancer is breast cancer, ovarian cancer, gastric cancer, multiple myeloma, or lymphoma.

EXAMPLES

The present invention is further illustrated by the following examples which should not be construed as further limiting.

Example 1

Iodine-131 Radiolabelling of Anti-HER2 VHH's

Radiochemical Procedure

The established procedure for radioiodination of $V_{HH}$'s was performed as follows: the necessary amount of sodium [I*] iodide was transferred to a mixture of 3% (v/v) Acetic Acid, 30% (v/v) tert-butylhydroperoxide, and N-succinimidyl 4-[$N^1,N^2$-bis(tert-butyloxycarbonyl) guanodinomethyl]-3-(trimethylstannyl)benzoate, all dissolved in chloroform. While stirring, the mixture was incubated for 50 min at room temperature. Subsequently, [I*]SGMIB-BisBoc was purified on normal phase HPLC, using an ethyl acetate/hexane gradient. Deprotection was achieved after a 15 minute incubation at room temperature with trifluoroacetic acid. Finally, the deprotected [I*]SGMIB was reacted with 100 μg of the anti-HER2 $V_{HH}$ sequence in borate buffer pH 8.5 during 20 min at room temperature. His-tagged [$^{131}$I] SGMIB-bivalent(2Rb17c-2Rb17c), His-tagged [$^{131}$I]SGMIB-monovalent(2Rb17c), and His-tagged [$^{131}$I]SGMIB-monovalent(2Rs15d) $V_{HH}$'s were purified on a PD-10 column equilibrated in PBS.

Quality Control

Quality control was performed by instant thin layer chromatography (iTLC), using glass microfiber sheets impregnated silica gel strips (Varian, Lake Forest, Calif., USA), ran with PBS, pH 7.4. In parallel, analytical radio-HPLC, using a polystyrene divinylbenzene copolymer reversed-phase column (PLRP-S 300 Å, 5 μm, 250/4 mm, Agilent, Diegem, Belgium) was performed. A mixture of 0.1% TFA in water and acetonitrile was used in the following protocol: 0-5 min 25% acetonitrile; 5-7 min 25-34% acetonitrile; 7-10 min 75-100% acetonitrile; 10-25 min 100% acetonitrile at a flow rate of 1 ml/min.

Example 2

Lutitium-177 Radiolabelling of Anti-HER2 VHH's

Conjugation of 1B4M-DTPA and CHX-A"-DTPA to $V_{HH}$'s
Anti-HER2 $V_{HH}$'s 2Rs15d, 2Rb17c and 1R136b were produced with 3 types of C-terminal amino acid tags: untagged ($V_{HH}$), His-tag ($V_{HH}$-HHHHHH (SEQ ID NO:9)), and Myc-His-tag ($V_{HH}$-AAAEQKLISEEDLNGAA-HHHHHH (SEQ ID NO:10)). A 10-fold molar excess of bifunctional chelator 1B4M-DTPA (for $^{177}$Lu) was conjugated for 3 h at RT to the free ε-amino-groups of lysines in the $V_{HH}$'s in 600 μl of 0.05 M sodium carbonate buffer (pH 8.5). The conjugation reaction was quenched by reducing the pH of the mixture to pH 7.0. $V_{HH}$-chelator was purified on Superdex 75 10/30 (GE Healthcare) in 0.1 M ammonium acetate buffer pH 7.0. The mean degree of conjugation was evaluated with ESI-Q-ToF-MS (Waters, Micromass), in positive mode.

Preparation of $^{177}$Lu-DTPA-V$_{HH}$'s

V$_{HH}$'s were labeled with $^{177}$Lu as previously described (20). Carrier-free $^{177}$Lu was obtained from ITG (Garching, Germany) as a chloride solution, with a specific activity of 3000 GBq/mg. The necessary amount of $^{177}$Lu was added to a test vial containing metal-free 0.1 M ammonium acetate buffer pH 5.0, to reach an end volume of 200 µL. Then, 25-100 µg of V$_{HH}$-DTPA (1 mg/mL) was added and incubated for 30 min at RT. The radiolabeled V$_{HH}$ solution was purified on a disposable Nap-5 gel filtration column (GE Healthcare) and pushed through a 0.22 µm filter. Radiochemical purity was assessed using iTLC with 0.2 M citric acid as mobile phase, and with either analytical radio-HPLC or radio-SEC. Radio-HPLC was performed using a polystyrene divinylbenzene copolymer reversed-phase column (PLRP-S 300 Å, 5 µm, 250/4 mm, Agilent, Diegem, Belgium). Here, a mixture of 0.1% TFA in H$_2$O and ACN was used as eluent with the following gradient: 0-5 min 25% ACN; 5-7 min 25-34% ACN; 7-10 min 75-100% ACN; 10-25 min 100% ACN at a flow rate of 1 ml/min. Radio-SEC was done on Superdex 75 5/150GL using PBS as mobile phase at a flow rate of 0.3 mL/min.

Example 3

Blood-Clearance of Monovalent, Non-Lifetime Extended, Untagged, [$^{131}$I]SGMIB-Labeled Anti-HER2 V$_{HH}$ 2Rs15d in C57bl/6 Mice Materials & Methods Six normal male C57bl/6 mice were used to assess blood clearance. Each animal received an intravenous injection of 2500 kBq untagged monovalent [$^{131}$I]SGMIB-labeled anti-HER2 VHH 2Rs15d (approximately 4 µg). Blood samples were collected with a microcapillary at 2, 5, 10, 15, 20, 40, 60 and 120 and 180 min post injection. Results were expressed in percentage of injected activity per total blood volume (% IA/TBV). The total blood volume was estimated as 7% of the total body weight. The blood half-life was determined through a biphasic nonlinear regression fit using GraphPad Prism.

Results

Untagged monovalent [$^{131}$I]SGMIB-labeled anti-HER2 VHH 2Rs15d was cleared following a biphasic blood curve. The calculated half-lives for the initial fast washout phase was about 1.93 min. After 60 min, less than 2% IA/TBV (percentage of injected activity per total blood volume) was measured in blood.

Example 4

Biodistribution and Dosimetry of Monovalent, Non-Lifetime Extended, Untagged, [$^{131}$I]SGMIB-Labeled Anti-HER2 VHH 2Rs15d in HER2$^+$ Tumor Xenografted Mice, and Radiation Dose Estimates in Adult Female Human Materials & Methods Female six weeks old CRL:Nu-FoxN1nu athymic mice were implanted with 60-day continuous release 17-β-estradiol pellets (0.72 mg, Innovative Research of America: Sarasota, Fla., USA) on their back one day prior to tumor implantation. HER2+BT474/M1 human breast cancer cells (10×10$^6$) in 50% Matrigel (BD Biosciences, Bedford, Mass., USA) were injected subcutaneously into the right flank and grown until they reached a volume of 250-350 mm$^3$.

The biodistribution profile of untagged monovalent [$^{131}$I] SGMIB-labeled anti-HER2 VHH 2Rs15d was determined. The animals (n=3) were injected with 1185 kBq of untagged monovalent [$^{131}$I]SGMIB-labeled anti-HER2 VHH 2Rs15d (2.0 µg). At 1, 3, 6, 24, 48, 72, 96, 120, 144 h after injection, the mice were euthanized by halothane overdose, dissected, and their organs collected. Tissues of interest were weighed and counted in a γ-counter for $^{131}$I radioactivity along with injection standards (Table 1). The obtained data (expressed as % IA/g) were used to calculate the corresponding tumor to healthy tissue ratios (Table 2).

In addition, the biodistribution values of untagged monovalent $^{131}$I-SGMIB-anti-HER2 VHH 2Rs15d were used for dosimetric calculations (Table 3). The values were time integrated to obtain the residence time per gram tissue. Briefly, the integration between time 0 and 144 h was made using the trapezoid method. Next, the absorbed doses were calculated. In the absorbed dose calculations, S values for $^{131}$I were obtained from RADAR phantoms (Unit Density Spheres) published on the internet. The S value for a 1 g sphere (0.0000304 Gy·Kg/MBq·s) was used generally to calculate all organ doses. This simplified dosimetry calculation is motivated by the fact that the low-energy β-particles in the $^{131}$I decay are locally absorbed, and photons and other penetrating radiations are contributing to a low extent, which means that the cross-talk between different organs in the mouse is negligible.

An estimation of organ-absorbed doses in adult female humans was performed by extrapolation of the biodistribution data of untagged monovalent [$^{131}$I]SGMIB-labeled anti-HER2 VHH 2Rs15d at different time points in mice to the adult female phantom using OLINDA software, using a voiding bladder interval of 1 h (Table 4). The calculations were based on time-activity curves to determine the number of disintegrations in organs. Organ doses and effective dose were calculated using the appropriate weighting factors for the various organs.

Results

Extremely high tumor to healthy tissue ratios were achieved (Table 2), highlighting the very low uptake in healthy tissues and thus the low toxicity. Tumor to tissue ratios of this extent as observed using the untagged monovalent [$^{131}$I]SGMIB-labeled anti-HER2 VHH 2Rs15d have never been published for other radioimmunobiologicals so far. In particular, these ratios were significantly higher compared to the HER2-targeting cysteine-tagged VHH termed 5F7GGC (Pruszynski et al., 2014; J. Nucl. Med. 55(4):650-656). Tumor to lungs, heart, liver, kidney, stomach, spleen, muscle and blood ratios were all significantly higher at time points 1 and 24 h for untagged monovalent [$^{131}$I]SGMIB-labeled anti-HER2 VHH 2Rs15d versus 5F7GGC VHH. It was especially surprising to detect the very low uptake value in the kidneys for the untagged monovalent [$^{131}$I]SGMIB-labeled anti-HER2 VHH 2Rs15d. This kidney uptake value was even lower than what had been reported for 5F7GGC VHH.

TABLE 1

After injection of the untagged monovalent [131I]SGMIB-labeled anti-HER2 VHH 2Rs15d, 21 different tissues of interest are counted for 131I activity in an automated gamma counter. Uptake values are expressed as % injected Activity/gram tissue (% IA/g), except for thyroid, adrenals and gallbladder for which % IA is used. Values represent an average (n = 3) ± SD.

| Organ/tissue | 1 H MEAN | 1 H SD | 3 H MEAN | 3 H SD | 6 H MEAN | 6 H SD | 24 H MEAN | 24 H SD | 48 H MEAN | 48 H SD |
|---|---|---|---|---|---|---|---|---|---|---|
| Brain | 0.08 | 0.08 | 0.49 | 0.44 | 0.01 | 0.003 | 0.002 | 0.001 | 0.0004 | 0.0001 |
| Lungs | 0.94 | 0.17 | 0.30 | 0.11 | 0.19 | 0.04 | 0.05 | 0.02 | 0.02 | 0.01 |
| Heart | 0.43 | 0.07 | 0.15 | 0.02 | 0.08 | 0.004 | 0.02 | 0.001 | 0.01 | 0.003 |
| Liver | 1.05 | 0.18 | 0.39 | 0.12 | 0.24 | 0.09 | 0.04 | 0.01 | 0.05 | 0.003 |
| Kidneys | 55.63 | 8.47 | 12.5 | 2.73 | 7.15 | 1.95 | 0.94 | 0.52 | 0.52 | 0.13 |
| Stomach | 0.94 | 0.39 | 0.71 | 0.76 | 0.12 | 0.06 | 0.01 | 0.04 | 0.01 | 0.004 |
| Pancreas | 0.18 | 0.04 | 0.05 | 0.01 | 0.02 | 0.005 | 0.01 | 0.002 | 0.003 | 0.001 |
| Spleen | 0.39 | 0.07 | 0.21 | 0.02 | 0.09 | 0.04 | 0.02 | 0.004 | 0.01 | 0.002 |
| Skin | 0.86 | 0.26 | 0.43 | 0.11 | 0.31 | 0.11 | 0.02 | 0.005 | 0.01 | 0.007 |
| Muscle | 0.62 | 0.15 | 0.24 | 0.15 | 0.08 | 0.01 | 0.01 | 0.01 | 0.004 | 0.002 |
| Bone | 1 | 0.08 | 0.53 | 0.30 | 0.28 | 0.2 | 0.04 | 0.01 | 0.02 | 0.01 |
| S. intestines | 0.37 | 0.09 | 0.58 | 0.58 | 0.16 | 0.01 | 0.01 | 0.003 | 0.004 | 0.001 |
| L. intestines | 0.3 | 0.12 | 0.36 | 0.34 | 0.1 | 0.02 | 0.01 | 0.01 | 0.004 | 0.002 |
| Lymphnodes | 0.44 | 0.15 | 0.19 | 0.03 | 0.1 | 0.02 | 0.02 | 0.01 | 0.01 | 0.003 |
| Blood | 0.83 | 0.02 | 0.19 | 0.06 | 0.07 | 0.01 | 0.02 | 0.002 | 0.01 | 0.003 |
| Uterus | 1.1 | 0.21 | 0.02 | 0.005 | 0.34 | 0.38 | 0.02 | 0.03 | 0.01 | 0.002 |
| Thyroid* | 0.01 | 0.002 | 0.001 | 0.001 | 0.001 | 0.0002 | 0.0001 | 0.00005 | 0.0001 | 0.00011 |
| Adenals* | 0.02 | 0.02 | 0.002 | 0.001 | 0.001 | 0.0001 | 0.0001 | 0.0001 | 0.0001 | 0.0001 |
| Galbladder* | 0.01 | 0.004 | 0.003 | 0.002 | 0.001 | 0.001 | 0.0002 | 0.00002 | 0.0001 | 0.00011 |
| Tumor | 20.22 | 1.64 | 17.77 | 1.87 | 7.16 | 1.18 | 5.1 | 1.9 | 1.16 | 0.16 |
| Bladder | 6.65 | 5.57 | 2.43 | 1.38 | 1.18 | 1.4 | 0.03 | 0.01 | 0.02 | 0.005 |

| Organ/tissue | 72 H MEAN | 72 H SD | 96 H MEAN | 96 H SD | 120 H MEAN | 120 H SD | 144 H MEAN | 144 H SD |
|---|---|---|---|---|---|---|---|---|
| Brain | 0.0014 | 0.0005 | 0.0003 | 0.0004 | 0.0008 | 0.0007 | 0.01 | 0.02 |
| Lungs | 0.0089 | 0.0024 | 0.02 | 0.01 | 0.01 | 0.003 | 0.03 | 0.02 |
| Heart | 0.0058 | 0.0009 | 0.01 | 0.002 | 0.004 | 0.0003 | 0.003 | 0.002 |
| Liver | 0.0112 | 0.0023 | 0.02 | 0.01 | 0.01 | 0.003 | 0.02 | 0.01 |
| Kidneys | 0.2413 | 0.1426 | 0.13 | 0.06 | 0.09 | 0.02 | 0.1 | 0.02 |
| Stomach | 0.0083 | 0.0016 | 0.01 | 0.01 | 0.004 | 0.0005 | 0.004 | 0.002 |
| Pancreas | 0.0014 | 0.0012 | 0.002 | 0.001 | 0.001 | 0.001 | 0.002 | 0.002 |
| Spleen | 0.005 | 0.0008 | 0.01 | 0.002 | 0.01 | 0.001 | 0.01 | 0.005 |
| Skin | 0.0181 | 0.0073 | 0.01 | 0.002 | 0.01 | 0.003 | 0.01 | 0.004 |
| Muscle | 0.002 | 0.0009 | 0.002 | 0.002 | 0.003 | 0.001 | 0.004 | 0.003 |
| Bone | 0.0159 | 0.0105 | 0.02 | 0.01 | 0.01 | 0.01 | 0.05 | 0.04 |
| S. intestines | 0.0078 | 0.0073 | 0.003 | 0.001 | 0.002 | 0.001 | 0.01 | 0.01 |
| L. intestines | 0.0071 | 0.0039 | 0.02 | 0.03 | 0.002 | 0.001 | 0.01 | 0.01 |
| Lymphnodes | 0.0086 | 0.0046 | 0.004 | 0.003 | 0.004 | 0.002 | 0.02 | 0.01 |
| Blood | 0.0098 | 0.0017 | 0.01 | 0.001 | 0.01 | 0.0003 | 0.01 | 0.001 |
| Uterus | 0.0063 | 0.002 | 0.01 | 0.002 | 0.004 | 0.001 | 0.003 | 0.002 |
| Thyroid* | 0.00001 | 0.00002 | 0.0001 | 0.0001 | 0.0001 | 0.0001 | 0.0001 | 0.00004 |
| Adenals* | 0.00011 | 0.00005 | 0.0001 | 0.0001 | 0.00003 | 0.00004 | 0.0001 | 0.0002 |
| Galbladder* | 0.0001 | 0.0001 | 0.00001 | 0.00001 | 0.00007 | 0.00006 | 0.0002 | 0.0003 |
| Tumor | 0.3952 | 0.0531 | 0.14 | 0.01 | 0.11 | 0.03 | 0.01 | 0.01 |
| Bladder | 0.0185 | 0.0074 | 0.01 | 0.01 | 0.01 | 0.002 | 0.01 | 0.01 |

TABLE 2

Calculated tumor to healthy tissue ratios. Values represent an average (n = 3) ± SD.

| Tumor to tissue | 1 H MEAN | 1 H SD | 3 H MEAN | 3 H SD | 6 H MEAN | 6 H SD | 24 H MEAN | 24 H SD | 48 H MEAN | 48 H SD |
|---|---|---|---|---|---|---|---|---|---|---|
| T/Brain | 435.35 | 278.36 | 57.59 | 36.68 | 830.65 | 351.38 | 3573.01 | 1848.90 | 2967.91 | 741.27 |
| T/Lungs | 21.95 | 3.96 | 63.55 | 18.44 | 38.24 | 13.02 | 95.01 | 12.86 | 99.92 | 58.70 |
| T/Heart | 47.37 | 4.31 | 122.36 | 10.13 | 93.48 | 10.06 | 332.65 | 129.69 | 121.73 | 15.44 |
| T/Liver | 19.76 | 3.95 | 49.12 | 16.93 | 31.71 | 10.07 | 139.18 | 44.97 | 23.76 | 2.96 |
| T/Kidney | 0.34 | 0.06 | 1.47 | 0.39 | 1.06 | 0.38 | 6.48 | 4.45 | 2.28 | 0.44 |
| T/Stomach | 24.73 | 11.98 | 47.70 | 32.92 | 68.30 | 26.79 | 434.72 | 203.18 | 203.02 | 135.91 |
| T/Pancreas | 112.78 | 20.65 | 398.68 | 103.12 | 380.57 | 31.62 | 1129.96 | 577.80 | 467.06 | 189.90 |
| T/Spleen | 53.66 | 14.59 | 85.43 | 7.36 | 103.47 | 80.11 | 336.61 | 172.00 | 107.51 | 23.59 |
| T/Skin | 25.42 | 9.73 | 42.48 | 8.31 | 23.89 | 4.70 | 232.89 | 43.89 | 98.33 | 46.17 |
| T/Muscle | 34.56 | 12.32 | 112.45 | 95.38 | 91.22 | 2.19 | 499.42 | 249.18 | 383.10 | 233.29 |
| T/Bone | 20.30 | 2.80 | 41.83 | 23.00 | 31.98 | 13.43 | 121.67 | 46.99 | 78.78 | 41.41 |

TABLE 2-continued

Calculated tumor to healthy tissue ratios. Values represent an average (n = 3) ± SD.

| | | | | | | | | | | |
|---|---|---|---|---|---|---|---|---|---|---|
| T/Small intestine | 56.73 | 11.52 | 57.89 | 45.42 | 46.28 | 11.40 | 1107.06 | 986.14 | 281.88 | 104.41 |
| T/Large intestine | 74.99 | 28.66 | 76.35 | 45.49 | 72.43 | 11.17 | 819.79 | 591.78 | 365.73 | 165.39 |
| T/Lymphnodes | 49.66 | 17.83 | 97.34 | 22.84 | 75.39 | 20.89 | 376.44 | 298.04 | 146.48 | 55.22 |
| T/Blood | 24.35 | 1.39 | 96.84 | 20.56 | 107.23 | 29.37 | 258.66 | 93.60 | 86.21 | 22.81 |
| T/Uterus | 18.77 | 3.29 | 773.99 | 150.39 | 43.43 | 29.74 | 260.55 | 53.85 | 107.01 | 21.00 |

| Tumor to tissue | 72 H | | 96 H | | 120 H | | 144 H | |
|---|---|---|---|---|---|---|---|---|
| | MEAN | SD | MEAN | SD | MEAN | SD | MEAN | SD |
| T/Brain | 305.22 | 69.97 | 1777.55 | 1503.79 | 800.14 | 1246.53 | 127.20 | 218.68 |
| T/Lungs | 46.84 | 13.85 | 14.05 | 8.15 | 23.92 | 19.31 | 1.38 | 1.94 |
| T/Heart | 70.57 | 20.95 | 29.61 | 10.39 | 27.94 | 5.13 | 6.29 | 6.49 |
| T/Liver | 36.22 | 9.22 | 7.53 | 3.27 | 13.19 | 6.27 | 1.14 | 0.68 |
| T/Kidney | 1.46 | 0.14 | 1.17 | 0.40 | 1.13 | 0.12 | 0.15 | 0.06 |
| T/Stomach | 48.35 | 5.77 | 20.07 | 9.04 | 27.86 | 7.02 | 3.95 | 2.21 |
| T/Pancreas | 401.81 | 238.60 | 99.27 | 41.36 | 122.83 | 49.57 | 208.69 | 347.90 |
| T/Spleen | 82.13 | 25.18 | 22.91 | 9.53 | 18.67 | 3.30 | 5.25 | 6.42 |
| T/Skin | 26.37 | 17.02 | 16.51 | 4.28 | 12.58 | 4.83 | 1.30 | 0.59 |
| T/Muscle | 209.72 | 55.17 | 397.50 | 619.22 | 37.80 | 7.76 | 11.12 | 15.97 |
| T/Bone | 34.05 | 23.93 | 8.63 | 2.38 | 9.68 | 6.90 | 1.25 | 1.91 |
| T/Small intestine | 85.01 | 55.60 | 56.79 | 27.42 | 54.00 | 18.94 | 6.88 | 9.13 |
| T/Large intestine | 70.39 | 41.52 | 19.75 | 14.92 | 92.04 | 60.83 | 4.41 | 4.81 |
| T/Lymphnodes | 54.48 | 23.58 | 216.58 | 326.69 | 28.43 | 7.59 | 0.97 | 0.32 |
| T/Blood | 41.65 | 12.01 | 17.69 | 0.40 | 16.53 | 4.75 | 2.78 | 0.87 |
| T/Uterus | 65.95 | 18.96 | 25.56 | 4.91 | 30.62 | 11.81 | 5.22 | 2.58 |

Using the same method as described in Pruszynski et al. for calculating radiation absorbed doses to the kidneys and based on the % IA/g tissue values (Table 1) a value of 835.96 cGy/mCi was obtained for untagged monovalent [$^{131}$I]SGMIB-labeled anti-HER2 VHH 2Rs15d (Table 3), which was less than half the value obtained for 5F7GGC VHH, based on dosimetry data from Pruszynski et al. Also much lower values were observed to liver, spleen, lungs, stomach and blood for untagged monovalent [$^{131}$I]SGMIB-labeled anti-HER2 VHH 2Rs15d.

The obtained value for untagged monovalent [$^{131}$I]SGMIB-labeled anti-HER2 VHH 2Rs15d (835.96 cGy/mCi) was surprisingly lower than the absorbed dose to kidneys for the his-tagged monovalent [$^{131}$I]SGMIB-labeled anti-HER2 VHH 2Rs15d (1055 cGy/mCi).

TABLE 3

Dosimetry calculations for untagged monovalent
[$^{131}$I]SGMIB-labeled anti-HER2 VHH 2Rs15d in
female HER2$^+$ tumor xenografted mice.

| Organ/tissue | Dose (cGy/mCi) |
|---|---|
| Brain | 9.38 |
| Lungs | 26.66 |
| Heart | 11.50 |
| Liver | 31.13 |
| Kidneys | 835.96 |
| Stomach | 24.94 |
| Pancreas | 3.75 |
| Spleen | 13.22 |
| Skin | 28.38 |
| Muscle | 11.37 |
| Bone | 32.24 |
| S intestines | 20.79 |
| L intestines | 15.79 |
| Lymphnodes | 13.11 |
| Blood | 14.72 |
| Galbladder | 0.18 |
| Tumor | 1188.34 |
| Urinary Bladder | 119.53 |

Radiation dose estimates for adult females were calculated from the biodistribution data of untagged monovalent [$^{131}$I]SGMIB-labeled anti-HER2 VHH 2Rs15d in mice using OLINDA 1.0 software. The calculations were based on time-activity curves to determine the number of disintegrations in 20 source organs. Organ doses, effective dose, and effective dose equivalent were calculated using the appropriate weighting factors for the various organs. Table 10 summarizes the calculated organ-absorbed doses. The effective dose was estimated at 0.0273 mSv/MBq.

TABLE 4

Radiation dose estimates to different organs for
adult female human based on OLINDA calculations.

| Target organ | Total (mSv/MBq) |
|---|---|
| Adrenals | 2.17E−04 |
| Brain | 7.27E−07 |
| Breasts | 5.84E−05 |
| Gallbladder wall | 7.33E−04 |
| Lower large intestine Wall | 7.99E−03 |
| Small Intestine | 3.17E−03 |
| Stomach wall | 3.52E−04 |
| Upper large intestine wall | 2.45E−03 |
| Heart wall | 7.12E−05 |
| Kidneys | 4.43E−04 |
| Liver | 2.62E−04 |
| Lungs | 6.49E−05 |

TABLE 4-continued

Radiation dose estimates to different organs for adult female human based on OLINDA calculations.

| Target organ | Total (mSv/MBq) |
|---|---|
| Muscle | 1.83E−03 |
| Ovaries | 7.45E−03 |
| Pancreas | 2.66E−04 |
| Red Marrow | 1.27E−03 |
| Osteogenic cells | 8.93E−04 |
| Skin | 6.16E−04 |
| Spleen | 2.63E−04 |
| Thymus | 3.93E−05 |
| Thyroid | 8.87E−06 |
| Urinary bladder wall | 4.91E−01 |
| Uterus | 1.58E−02 |
| Total Body | 1.86E−03 |
| Effective dose Equivalent | 3.33E−02 |
| Effective dose | 2.73E−02 |

Example 5

Biodistribution of Untagged Monovalent [$^{131}$I]SGMIB-Labeled anti-HER2 VHH 2Rs15d, in Competition with Trastuzumab and/or Pertuzumab in HER2$^+$ Tumor Xenografted Mice The biodistribution profile of untagged monovalent [$^{131}$I] SGMIB-labeled anti-HER2 VHH 2Rs15d was evaluated in HER2$^+$ tumor xenografted mice, after pretreatment with Trastuzumab, pertuzumab, or a combination of both. Trastuzumab (trade names: Herclon®, Herceptin®) and pertuzumab (Trade name: Perjeta®) are monoclonal antibodies that interfere with the HER2/neu receptor. Their main use is to treat certain breast cancers.

Materials and Methods

Female six weeks old CRL:Nu-FoxN1nu athymic mice were implanted with 60-day continuous release 17-β-estradiol pellets (0.72 mg, Innovative Research of America: Sarasota, Fla., USA) on their back one day prior to tumor implantation. HER2$^+$ BT474/M1 human breast cancer cells (5×10$^6$) in 50% Matrigel (BD Biosciences, Bedford, Mass., USA) were injected subcutaneously into the right flank and grown until they reached a volume of 150-250 mm$^3$. 72 h prior to untagged monovalent [$^{131}$I]SGMIB-labeled anti-HER2 VHH 2Rs15d administration, animals (n=3) were pretreated with a 100 molar excess of anti-HER2 mAbs. Next, they received 1185 kBq of untagged monovalent [$^{131}$I]SGMIB-labeled anti-HER2 VHH 2Rs15d (5.0 µg). 1 h after injection, the mice were euthanized by halothane overdose, dissected, and their organs collected. Tissues of interest were weighed and counted in a γ-counter for $^{131}$I radioactivity along with injection standards. Results were expressed as percentage injected activity per gram of tissue (% IA/g).

Results

The results are shown in Table 5. No significant difference in tumor uptake was observed between the animal group that only received untagged monovalent [$^{131}$I]SGMIB-labeled anti-HER2 VHH 2Rs15d, and the animal groups that received a pretreatment of Herceptin® and/or Perjeta®.

Thus, the untagged monovalent [$^{131}$I]SGMIB-labeled anti-HER2 VHH 2Rs15d does not compete with the monoclonal antibodies Herceptin® and Perjeta® for binding to HER2, as shown by the presented in vivo competition assay.

TABLE 5

Biodistribution data for untagged monovalent [$^{131}$I]SGMIB-labeled anti-HER2 VHH 2Rs15d in female HER2$^+$ tumor xenografted mice with and without competition of Trastuzumab, Pertuzumab, or a combination of both anti-HER2 mAbs. Values are expressed as % Injected Activity/gram tissue (% IA/g), except for thyroid, for which % IA is used. Values represent an average (n = 3) ± SD.

| Organ/tissue | 2Rs15d | | 2Rs15d + Trastuzumab | | 2Rs15d + Pertuzumab | | 2Rs15d + Trastuzumab and Pertuzumab | |
|---|---|---|---|---|---|---|---|---|
| Brain | 0.03 | 0.01 | 0.03 | 0.01 | 0.04 | 0.02 | 0.05 | 0.03 |
| Lungs | 0.94 | 0.33 | 0.59 | 0.22 | 0.75 | 0.21 | 0.97 | 0.46 |
| Heart | 0.34 | 0.03 | 0.35 | 0.04 | 0.39 | 0.03 | 0.47 | 0.06 |
| Liver | 1.58 | 0.26 | 1.82 | 0.78 | 0.95 | 0.49 | 1.38 | 0.29 |
| Kidney | 78.08 | 26.88 | 60.31 | 17.08 | 66.21 | 15.71 | 75.74 | 11.28 |
| Stomach | 0.54 | 0.15 | 0.58 | 0.19 | 0.51 | 0.19 | 0.87 | 0.28 |
| Pancreas | 0.13 | 0.03 | 0.14 | 0.01 | 0.21 | 0.14 | 0.18 | 0.01 |
| Spleen | 0.43 | 0.1 | 0.49 | 0.15 | 0.44 | 0.05 | 0.7 | 0.1 |
| Muscle | 0.53 | 0.16 | 0.87 | 0.7 | 0.34 | 0.06 | 0.87 | 0.53 |
| Bone | 0.95 | 0.19 | 0.78 | 0.06 | 1.14 | 0.46 | 1.1 | 0.1 |
| S. intestines | 0.27 | 0.1 | 0.25 | 0.06 | 0.24 | 0.08 | 0.45 | 0.1 |
| L. intestines | 0.32 | 0.14 | 0.16 | 0.03 | 0.25 | 0.12 | 0.41 | 0.09 |
| Lymphnodes | 0.56 | 0.12 | 0.46 | 0.08 | 0.55 | 0.13 | 0.91 | 0.21 |
| Blood | 0.77 | 0.11 | 0.57 | 0.06 | 0.66 | 0.14 | 0.82 | 0.09 |
| Uterus | 0.69 | 0.22 | 0.58 | 0.28 | 0.62 | 0.27 | 0.9 | 0.32 |
| Thyroid* | 0.01 | 0.002 | 0.002 | 0.001 | 0.002 | 0.001 | 0.002 | 0.001 |
| Tumor | 11.00 | 3.94 | 9.31 | 2.35 | 8.91 | 2.06 | 8.59 | 2.85 |

Example 6

Therapeutic Efficacy of Untagged Monovalent [$^{131}$I]SGMIB-Labeled Anti-HER2 VHH 2Rs15d in HER2$^+$ Tumor Xenografted Mice The therapeutic efficacy of untagged monovalent [$^{131}$I] SGMIB-labeled anti-HER2 VHH 2Rs15d was assessed by measuring its capacity to inhibit tumor growth in HER2$^+$ tumor xenografted mice. The specificity of its therapeutic efficacy was evaluated by including 2 controls; (1) administration of an untagged monovalent [$^{131}$I]SGMIB-labeled non-targeting control VHH and (2) administration of the vehicle solution PBS.

Materials and Methods

19 CRL:Nu-FoxN1nu mice were inoculated in the right hind leg with $5 \times 10^6$ HER2+ BT474/M1 tumor cells in 50/50 Matrigel/cell culture medium. Tumors were grown until $50 \pm 30$ mm$^3$, as determined by caliper measurements. Next, animals were randomly divided into 3 treatment groups; Treatment group 1 (n=6): untagged monovalent [$^{131}$I]SGMIB-labeled anti-HER2 VHH 2Rs15d (250±50 µCi/treatment), treatment group 2 (n=6): untagged monovalent [$^{131}$I]SGMIB-labeled non-targeting control VHH (250±50 µCi/treatment), and treatment group 3 (n=7): vehicle solution. Animals were treated five times (once a week during five weeks). Tumor volume and animal weight was measured every week. Animals were euthanized when tumors reached 1 cm$^3$ or when a weight reduction of >20% was observed. After 150 days, the results were combined in a survival curve, after which statistical analysis was performed (Log-rank (Mantel-Cox) test).

Results

Mice bearing small HER2$^+$ BT474/M1 tumors (50±30 mm$^3$) were intravenously injected with either untagged monovalent [$^{131}$I]SGMIB-labeled anti-HER2 VHH 2Rs15d, untagged monovalent [$^{131}$I]SGMIB-labeled non-targeting control VHH or the vehicle solution PBS. All animals of the PBS-treated (n=7) and all except for 1 animal in the group treated with untagged monovalent [$^{131}$I]SGMIB-labeled non-targeting control VHH (n=6), were euthanized at day 150 due to the development of large tumors (>1 cm$^3$) (FIG. 1). No statistically significant difference was observed in event-free survival between both control groups.

In contrast, tumor growth was delayed significantly in the group treated with untagged monovalent [$^{131}$I]SGMIB-labeled anti-HER2 VHH 2Rs15d compared to the two control animal groups (FIG. 1). Moreover, up to day 150, half of the treated animal group showed complete absence of tumor burden. Overall, survival was significantly longer for the treated group compared to the control groups that received PBS (P<0.05) or untagged monovalent [$^{131}$I]SGMIB-labeled non-targeting control VHH (P<0.05), respectively. In other words, [$^{131}$I]SGMIB-labeled anti-HER2 2Rs15d VHH is able to slow down and even prevent tumor growth progression when binding to HER2 protein. This finding is remarkably surprising as it is shown that a radiolabeled untagged, non-lifetime extended, monovalent VHH has a therapeutic effect, while it is commonly accepted that for a therapeutic effect, lifetime extension and multivalency are required.

Example 7

Determination of Screening Dose and Therapeutic Dose

An Iodine-131 labeled VHH is administered in a screening dose (e.g., up to 185 MBq) in patients to measure targeting to the cancer lesions and its retention in healthy tissues.

For this purpose, a total body planar gamma camera imaging or single photon emission tomography is performed between one hour and twenty-four hours after administration of the Iodine-131 labeled VHH. If the cancer lesions show uptake of the Iodine-131 labeled VHH, the patient is eligible for Iodine-131 labeled VHH treatment. Based on the scan results it is possible to determine the ideal total treatment dose for this patient and also determine the maximum dose that can be administered without toxic effects to healthy tissues.

A first treatment dose of Iodine-131 labeled VHH can be administered as soon as the uptake is confirmed in the cancer lesions (based on the scan). Typical radioactive doses range between 1110-5550 MBq. This dose can be repeated on a weekly basis as long as required to obtain the ideal total dose for effective cancer treatment, however a typical cycle of treatments is 5 to 6 doses.

Example 8

Phase I Study to Evaluate the Safety,
Biodistribution, Radiation Dosimetry and Tumor
Imaging Potential of [$^{131}$I]SGMIB-Labeled
Anti-HER2 VHH 2Rs15d in Healthy Volunteers
and Breast Cancer Patients A single center, open, non-randomized first-in-man clinical trial is performed. This study is conducted in 2 parts:

Part I is in healthy volunteers to evaluate the safety, biodistribution and radiation dosimetry of [$^{131}$I]SGMIB-labeled anti-HER2 VHH 2Rs15d.

Part II is in patients with HER2+ breast cancer to evaluate the safety and biodistribution, and to evaluate the tumor uptake of [$^{131}$I]SGMIB-labeled anti-HER2 VHH 2Rs15d.

Inclusion and exclusion criteria for the healthy volunteer subjects and patients are as follows:

Healthy volunteers included in the study have given informed consent, have agreed
not to drink alcoholic beverages or use any drugs during the study, have blood parameters within normal ranges, and are at least 18 years old.

Pregnant subjects, breast feeding subjects, subjects with occupational exposure to ionizing irradiation, subjects with clinical significant disease or on concomitant therapy (except contraception), subjects with previous thyroid disorders, subjects that received radiolabeled compounds with a long half-life (>7 h) for diagnostic or therapeutic purposes within the last 2 days, subjects with absolute contra-indications for thyroid blockage with potassium iodide, subjects with abnormal liver (i.e. ALT/AST>2 times normal values; bilirubin>1.5 time normal values), sSubjects with abnormal kidney function (i.e. <50 ml/min/1.73 m2), subjects with recent (<1 week) gastrointestinal disorders (CTCAE v4.0 grade 3 or 4) with diarrhea as major symptom, subjects with any serious active infection, subjects who have any other life-threatening illness or organ system dysfunction, which in the opinion of the investigator would either compromise subject safety or interfere with the evaluation of the safety of the test radiopharmaceutical, subjects who cannot communicate reliably with the investigator, subjects who are unlikely to cooperate with the requirements of the study, subjects at increased risk of death from a pre-existing concurrent illness, subjects who participated already in the study and subjects who participated in a previous trial with Anti-HER2 2Rs15d are not included in the study.

Patients included in the study have given informed consent, have agreed not to drink alcoholic beverages or use any drugs during the study, are at least 18 years old, and have local, locally advanced or metastatic HER2+ breast carcinoma as diagnosed on biopsied tissue by immunohistochemistry or fluorescence in situ hybridization (FISH).

Pregnant patients, breast feeding patients, patients with occupational exposure to ionizing irradiation, patients with previous thyroid disorders, patients that received radiolabeled compounds with a long half-life (>7 h) for diagnostic or therapeutic purposes within the last 2 days, patients with absolute contra-indications for thyroid blockage with potassium iodide, patients with abnormal liver (i.e. ALT/AST>2 times normal values; bilirubin>1.5 time normal values), patients with abnormal kidney function (i.e. <50 ml/min/1.73 m2), patients with recent (<1 week) gastrointestinal disorders (CTCAE v4.0 grade 3 or 4) with diarrhea as major symptom, patients with any serious active infection, patients who have any other life-threatening illness or organ system dysfunction, which in the opinion of the investigator would either compromise patient safety or interfere with the evaluation of the safety of the test radiopharmaceutical, patients who cannot communicate reliably with the investigator, patients who are unlikely to cooperate with the requirements of the study, patients at increased risk of death from a pre-existing concurrent illness, patients who participated already in the study, and patients who participated in a previous trial with Anti-HER2 2Rs15d are not included in the study.

All healthy subjects and patients receive an intravenous injection of 50±40 μg [$^{131}$I]SGMIB-labeled anti-HER2 VHH 2Rs15d with radioactivity of 111±74 MBq using an infusion pump within 5±3 min via an intravenous line inserted in a vein or port-a-cath. The product is administered as a single dose with a radioactivity of 55±18 MBq for healthy volunteers; in HER2+ breast cancer patients the product is administered as a single dose with a radioactivity of 148±37 MBq.

24±6 h before [$^{131}$I]SGMIB-labeled anti-HER2 VHH 2Rs15d administration and continued until 48±12 h after administration of [$^{131}$I]SGMIB-labeled anti-HER2 VHH 2Rs15d, all healthy subjects and patients are orally administered 130 mg potassium iodide for thyroid blockage dosed as 1 ingestion daily.

Outcome Measures of Safety and Tolerability

Tolerability and safety of [$^{131}$I]SGMIB-labeled anti-HER2 VHH 2Rs15d is assessed by the collection and evaluation of data pertaining to all adverse events experienced by subjects during the study.

Pre-administration, subjects undergo a physical examination including vital signs (arterial blood pressure and pulse rate) and are asked about changes in concomitant diseases and general physical and emotional state using open, non-leading questions. Additionally, the vital signs are monitored at 5±10 min post-administration. A second physical exam is performed at 4.5±1 h post-administration for the healthy subjects and at 3±1 h for the HER2+ breast cancer patients.

Blood is collected for hematology and clinical chemistry before and at 24±4 h post-administration. Any clinically relevant change from a baseline laboratory value is recorded as an adverse even unless it can reasonably be assumed to result from improper handling, a measurement error or some other technical cause.

In addition, blood samples are taken from the healthy volunteers before and at 5±3 min, 10±3 min, 20±5 min, 30±5 min, 60±15 min, 105±30 min, 225±30 min, 23.75±4 h, 71.75±4 h post-administration for activity measurements, so as to obtain the time-activity curve of [$^{131}$I]SGMIB-labeled anti-HER2 VHH 2Rs15d in blood. Whole blood and plasma samples are counted against appropriate standards of known dilution in an automatic gamma well counter and, after correction for decay and background activity, expressed as a percentage of the injected activity (% IA). The blood volume of each volunteer is estimated according to body weight and height, using Nadler's formula and the subject's hematocrit.

Urine is sampled from the healthy volunteers at 60±15 min, 225±30 min, 23.75±4 h, and 71.75±4 h post-administration to measure the fraction of un-metabolized product by size-exclusion chromatography (SEC) or reverse-phase high pressure liquid chromatography (RP-HPLC).

Human biodistribution is assessed for the healthy volunteers using a dynamic scan that is taken at 0-30±10 min post-administration and planar total body scans that are taken at 40±10 min, 120±30 min, 240±30 min, 24±4, and 72±4 h post-administration.

Human dosimetry is quantified using region of interest measurements on the total body scans of the different subjects using OLINDA/EXM software 1.0.

Outcome Measures of Tumor Targeting

The tumor targeting potential is visually scored as positive (intense, moderate or low) or negative on SPECT/CT scans of the patients taken 2.5±1 h and 24.5±4 h post-administration. The activity per unit of volume is quantified.

Example 9

Non-Clinical Toxicology Study of [$^{131}$I]SGMIB-Labeled Anti-HER2 VHH 2Rs15d

Material and Methods

[$^{127}$I]SGMIB-labeled anti-HER2 VHH 2Rs15d is defined as the non-radioactive reference material of [$^{131}$I]SGMIB-labeled anti-HER2 VHH 2Rs15d.

The toxicity profile of [$^{127}$I]SGMIB-labeled anti-HER2 VHH 2Rs15d was assessed following single microdose intravenous administration to Swiss Albino Mice. A single dose of [$^{127}$I]SGMIB-labeled anti-HER2 VHH 2Rs15d formulation was administered through intravenous route to group (G2) of 15 mice per sex at the dose of 1.4 mg/kg. The dose level of 1.4 mg/kg is 1000 times the expected dose in human as required by the microdosing toxicity guideline of EMEA (CPMP/ICH/286/95).

The concurrent vehicle control group (G1) consisted of 15 mice per sex and received vehicle (Phosphate Buffered Saline) only. The dose volume administered to each mouse was 6 mL/kg body weight. Parameters evaluated were clinical signs, mortality, changes in body weight and food intake, haematology and clinical chemistry parameters, organ weights and gross pathology. The treated mice were sacrificed on Day 2 (10 mice/sex/group) and on Day 15 (remaining 5 mice/sex/group).

Results

No test item-related mortality or clinical signs, changes in body weights, body weight gains and food consumption were observed throughout the experimental period. There were no test item-related changes in haematology, clinical chemistry, terminal fasting body weights, organ weights/ratios and gross pathology.

Therefore, it is concluded that the single microdose intravenous administration of [$^{127}$I]SGMIB-labeled anti-HER2 VHH 2Rs15d at the dose level of 1.4±10% mg/kg body weight to Swiss Albino Mice has caused no toxicity under the test conditions.

Example 10

Non-Clinical, In Vitro Studies with [$^{131}$I]SGMIB-Labeled Anti-HER2 VHH 2Rs15d Material and Methods Stability of [$^{131}$I]SGMIB-Labeled Anti-HER2 VHH 2Rs15d in PBS and in Human Serum

[$^{131}$I]SGMIB-labeled anti-HER2 VHH 2Rs15d was incubated in phosphate-buffered saline (PBS) at 25° C. during 144 h. Aliquots were taken at 0, 1, 48, 72 and 144 h and analyzed with radio-HPLC. Stability in human serum was analyzed by incubating [$^{131}$I]SGMIB-labeled anti-HER2 VHH 2Rs15d with human serum at 37° C. during 168 h. Aliquots were taken at 0, 3, 24, 48, 72, 96 and 168 h, and subsequently analyzed with radio-SEC.

HER2-Expressing Tumor Cell Binding: Specificity

To assess the specificity of the [$^{131}$I]SGMIB-labeled anti-HER2 VHH 2Rs15d against HER2-expressing tumor cells, cell-binding studies were performed. To demonstrate that the binding is receptor specific, 1000-fold excess cold starting anti-HER2 VHH 2Rs15d was added to HER2+cells in the control experiments to saturate the HER2 receptors.

HER2-Expressing Tumor Cell Binding: Affinity

The binding affinity of [$^{131}$I]SGMIB-labeled anti-HER2 VHH 2Rs15d on HER2-expressing tumor cells was evaluated. Here, HER2-expressing tumor cells were incubated with serial dilutions ranging from 0 to 300 nM of [$^{131}$I]SGMIB-labeled anti-HER2 VHH 2Rs15d. A 100-fold excess of unlabeled anti-HER2 VHH 2Rs15d (blocked HER2-expressing tumor cells) was added in parallel to assess non-specific binding.

HER2-Expressing Tumor Cell Binding: Internalization

Cellular retention of [$^{131}$I]SGMIB-labeled anti-HER2 VHH 2Rs15was evaluated at different time points on HER2-expressing tumor cells. The cells were incubated with 25 nM of [$^{131}$I]SGMIB-labeled anti-HER2 VHH 2Rs15and incubated at 37° C. during 0, 1, 2, 4, 6, and 24 h. A 100-fold excess of unlabeled anti-HER2 VHH1 (blocked HER2-expressing tumor cells) was added in parallel to assess non-specific binding. Four fractions were characterized: supernatans, cell membrane-bound, internalized, and total cell associated (membrane bound+internalized).

Results

Figure 2:
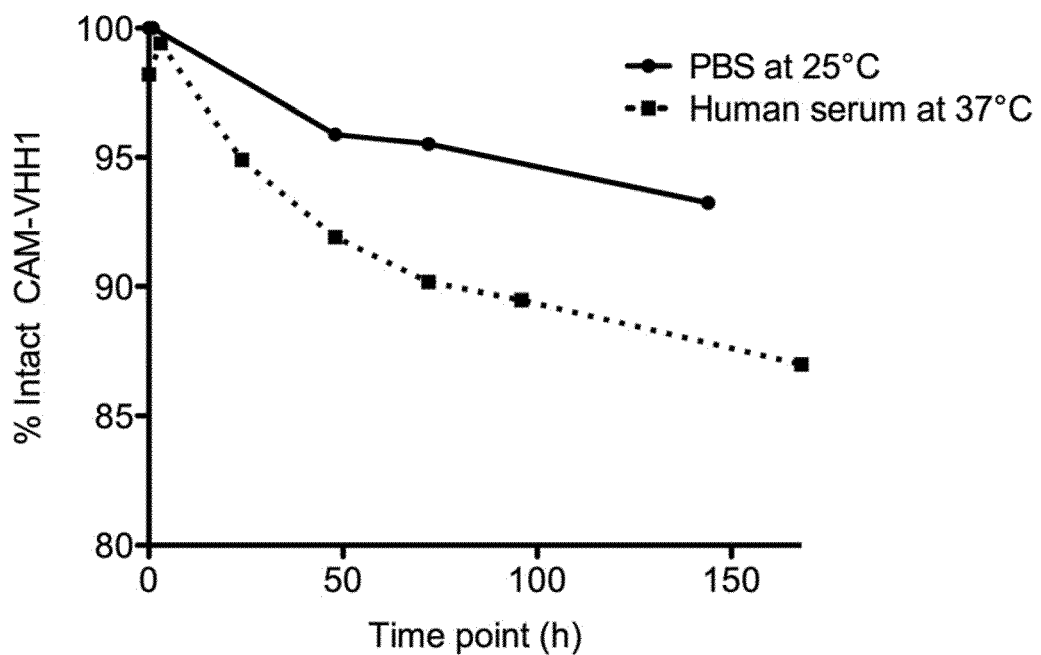
FIG. 2 The stability of [$^{131}$I]SGMIB-labeled anti-HER2 VHH 2Rs15d (CAM-VHH1) in PBS at 25° C. up to 144 h and in human serum at 37° C. up to 168 h. More than 96% of the activity was found in the protein fraction after 72 h while incubating in PBS, and about 95% after 24 while incubating in human serum.

[$^{131}$I]SGMIB-labeled anti-HER2 VHH 2Rs15d was stable for at least 72 h in phosphate-buffered saline (PBS) at 25° C., with >96% intact [$^{131}$I]SGMIB-labeled anti-HER2 VHH 2Rs15d (FIG. 2). In human serum, 95% of [$^{131}$I]SGMIB-labeled anti-HER2 VHH 2Rs15d was still intact after 24 h, and it gradually decreased to 87% after 168 h (FIG. 2).

Figure 3:
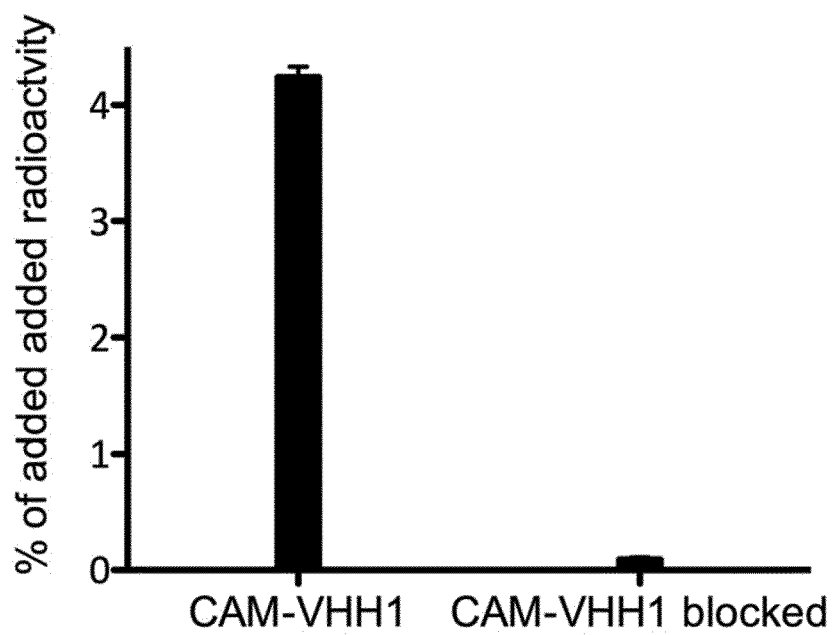
FIG. 3 Specific binding of [$^{131}$I]SGMIB-labeled anti-HER2 VHH 2Rs15d (CAM-VHH1) on HER2-expressing and blocked HER2-expressing tumor cells. Data are presented as mean±SD (n=6).

Results of the binding specificity experiments showed that the binding of [$^{131}$I]SGMIB-labeled anti-HER2 VHH 2Rs15d was receptor mediated and could be prevented by receptor saturation (FIG. 3).

Figure 4:
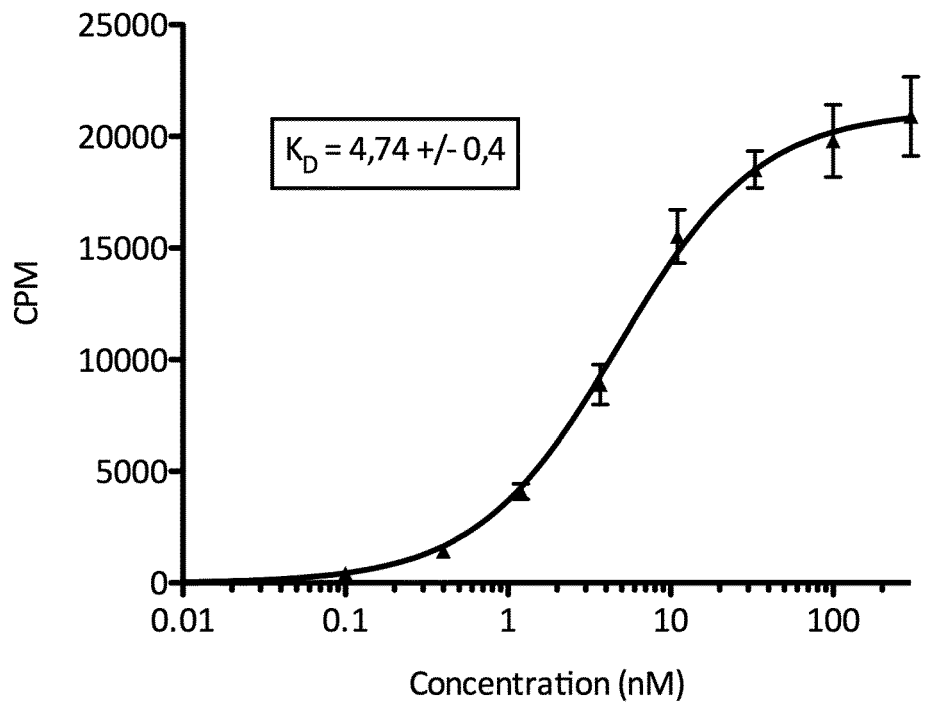
FIG. 4 Binding affinity of [$^{131}$I]SGMIB-labeled anti-HER2 VHH 2Rs15d (CAM-VHH1) on HER2-expressing tumor cells. Data are presented as mean±SD (n=3), resulting in a $K_D$ of 4.74±0.4 nM.

[$^{131}$I]SGMIB-labeled anti-HER2 VHH 2Rs15d bound on HER2-expressing tumor cells with an affinity of 4.74±0.4 nM (FIG. 4).

Figure 5:
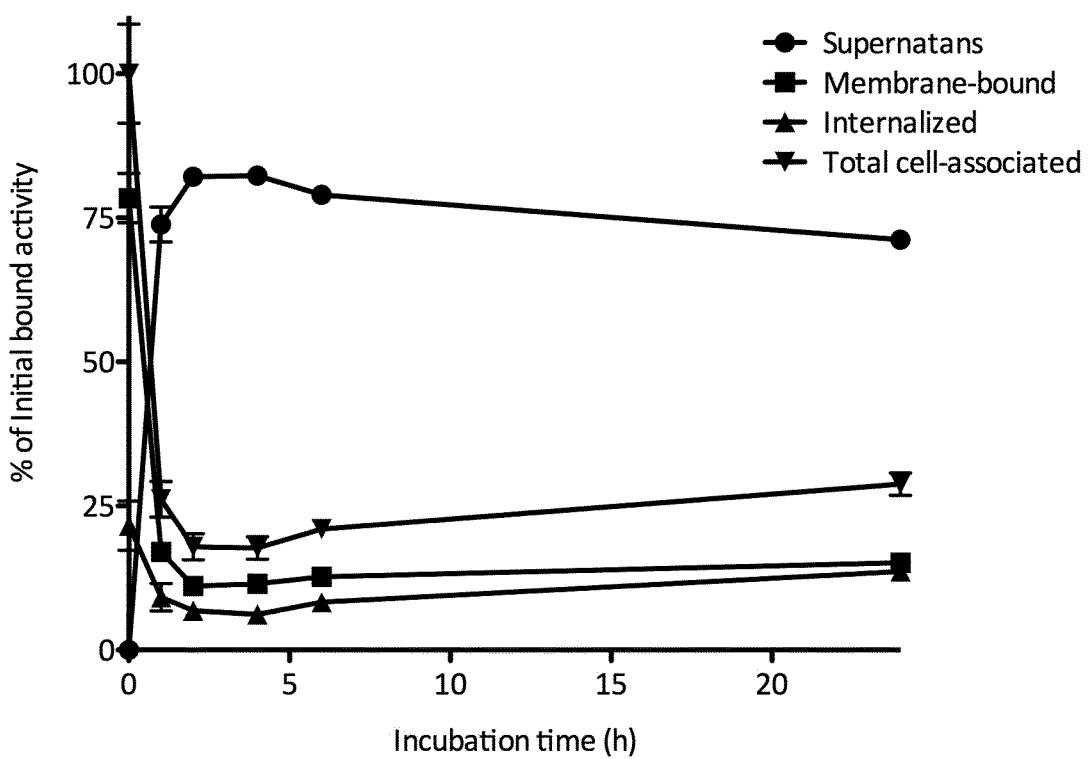
FIG. 5 Internalization profile of [$^{131}$I]SGMIB-labeled anti-HER2 VHH 2Rs15d (CAM-VHH1) in HER2-expressing tumor cells. Data are presented as mean±SD (n=3), at time points 0, 1, 2, 4, 6, and 24 h.

After 24 h about 25% of initial bound intact [$^{131}$I]SGMIB-labeled anti-HER2 VHH 2Rs15d is still interacting with the tumor cells, of which half is bound to the membrane, and half is internalized in the cells (FIG. 5).

Example 11

Formulation of [$^{131}$I]SGMIB-Labeled Anti-HER2 VHH 2Rs15d for Intravenous Administration Manufacture of [$^{131}$I]SGMIB-Labeled Anti-HER2 VHH 2Rs15d For the manufacture of [$^{131}$I]SGMIB-labeled anti-HER2 VHH 2Rs15d, the radioiodinating agent N-succinimidyl 4-guanidinomethyl-3-$^{131}$I-iodobenzoate ($^{131}$I-SGMIB) was synthesized first.

The radiosynthesis of $^{131}$I-SGMIB was performed via an electrophilic radioiodination of 50 micrograms tin precursor of SGMIB (SnMe$_3$-BisBoc-SGMIB), followed by deprotection under anhydrous conditions and purification by semi-prep HPLC. The collected HPLC fraction was diluted with water. The intermediate product was trapped on a tC18 Plus cartridge, rinsed with water and eluted with acidified ethanol.

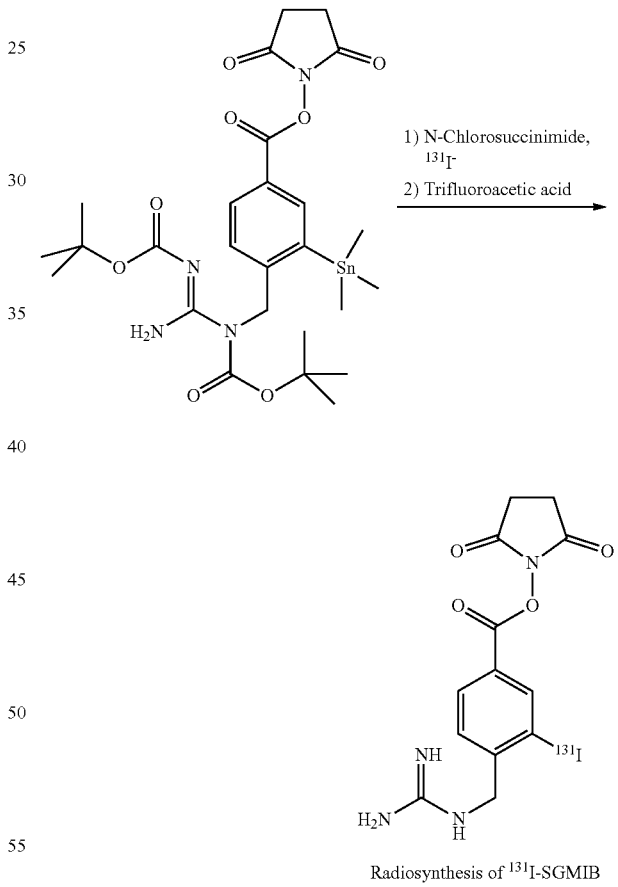

Radiosynthesis of $^{131}$I-SGMIB

The synthesis or conjugation of [$^{131}$I]SGMIB-labeled anti-HER2 VHH 2Rs15d was carried out via a nucleophilic substitution at room temperature using $^{131}$I-SGMIB as substrate and anti-HER2 VHH 2Rs15d (Innogenetics) as nucleophile. For obtaining an optimal conjugation, the anti-HER2 VHH 2Rs15d was first desalted from its PBS-buffer (pH 7.4) and dissolved in borate buffer (pH 8.5), using a Vivaspin centrifugal concentrator. After the conjugation, the reaction mixture was purified on a Pd-10 column.

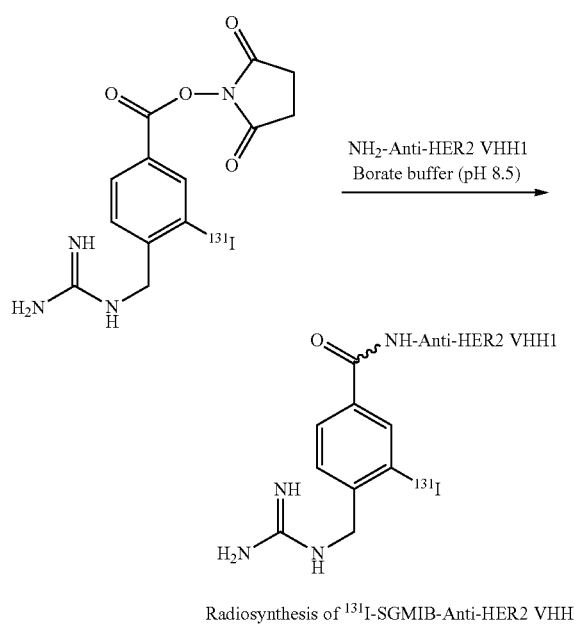

Radiosynthesis of $^{131}$I-SGMIB-Anti-HER2 VHH1

Formulation of [$^{131}$I]SGMIB-Labeled Anti-HER2 VHH 2Rs15d

After elution of [$^{131}$I]SGMIB-labeled anti-HER2 VHH 2Rs15d in 13 mL clinical buffer (PBS buffer) from the PD-10 column, the amount of radioactivity was measured. The purified and diluted [$^{131}$I]SGMIB-labeled anti-HER2 VHH 2Rs15d was filter sterilized in a closed isolator class A in a class C background. For this filling and sterile filtration step the formulated product was passed from the formulation vial to an analysis vial (used for quality control) through a sterile 0.2 μm Sartorius filter and subsequently from the analysis vial to the product vial through a second sterile 0.2 μm Sartorius filter. A vacuum pump was used as motive force. Finally, the product vial was transferred to a labelled container. A settle plate was opened during the filtration process.

Equipment used during filtration process were sterile needles, sterile tubing with long needles, sterile 0.2 μm Sartorius filters and sterile, closed, empty vials. Using aseptic assembly techniques, sterile needles were attached to the Sartorius filters.

The composition of the formulation is shown in Table 6 and the specifications in Table 7.

TABLE 6

Composition of a batch (approx.. 15 ml) formulation of [131I]SGMIB-labeled anti-HER2 VHH 2Rs15d for intravenous administration.

| Name of ingredient | Concentration | Function |
|---|---|---|
| Active ingredients | | |
| $^{131}$I-SGMIB-Anti-HER2 VHH1 | 10-33.3 MBq/ml | Active ingredient |
| Other ingredients | | |
| Cold Anti-HER2 VHH1 | 0.0067 mg/ml | Solvent |
| Sterile Isotonic Phosphate Buffered | 15 ml | |
| NaCl | 8.2 mg/ml | |
| Na$_2$HPO$_4$•12H$_2$O | 3.1 mg/ml | |
| NaH$_2$PO$_4$•2H$_2$O | 0.3 mg/ml | |

TABLE 7

Specifications for of [131I]SGMIB-labeled anti-HER2 VHH 2Rs15d

| General | Requirements |
|---|---|
| Appearance | Clear, colourless fluid |
| pH | 6.4-8.4 |
| HPLC | |
| Chemical Purity | Next to injection peak and carrier no other UV peaks compared to the blank. |
| Radiochemical Identity | Rt of the product is within 1 minute of the reference - Rt 6.9-8.9 |
| Radiochemical Purity | ≥97.0% |
| i-TLC | |
| Radiochemical purity | ≥97.0% |
| Integrity filter | Filter Integrity test Sterilisation filter ≥2.0 Bar |
| Sterility (Media Fill) | Sterile |
| Bacterial endotoxin content | Sample value ≤2.5 EU/ml Sample rxn time CV <25.0% Spike rxn time CV <25.0% Spike recovery (50-200%) |
| Antigen binding (SKOV cells) | ≥70.0% |
| Stability | Radiochemical purity after (24) h. ≥95.0% (at RT) |

Example 12

In Vivo Imaging and Biodistribution Measurements with [$^{131}$I]SGMIB-Labeled Anti-HER2 VHH 2Rs15d Four female CRL:Nu-FoxN1nu mice were implanted with a 60-day slow-release estrogen pellet, after which they were inoculated in the right hind leg with $10 \times 10^6$ HER2+ tumor cells in 50/50 matrigel/cell culture medium. Tumors were grown until 450±200 mm³, determined through caliper measurement.

Next, mice were injected intravenously in the tail vein with 248±1 μCi [$^{131}$I]SGMIB-labeled anti-HER2 2Rs15d VHH, followed by micro-SPECT/CT imaging after 1, 4 and 24 h. During the scans, animals were anaesthetized using 2% isoflurane (at a 1.5 L/min oxygen flow), and kept warm using a heating pad. Micro-SPECT/CT imaging was performed using a Vector⁺/CT MILabs system. For this experiment, imaging was performed using a PET collimator and a spiral scan mode of 94 bed positions (19 s per position). For CT, a normal scan mode of only one position was used. The obtained SPECT data were reconstructed with a 0.6 voxel size, 2 subsets and 7 iterations, after which images were fused and corrected for attenuation based on the CT scan. Images were analyzed using a medical image data analysis tool (AMIDE) and OsiriX. Uptake values of [$^{131}$I]SGMIB-labeled anti-HER2 2Rs15d VHH in a selection of organs and tissues were analyzed and expressed as % injected activity (% IA)/cc.

1 h after injection, the highest fraction of [$^{131}$I]SGMIB-labeled anti-HER2 2Rs15d VHH was found in bladder, and to a lesser extend in kidneys and tumor. After 4 and 24 h, the fraction in kidneys dropped significantly to a value of below 0.3% IA/cc after 24 h, while in tumor the drop was less pronounced (still>1% IA/cc after 24 h). After 24 h only tumor and bladder was seen on the micro-SPECT/CT images (data not shown). Very low uptake values were registered for thyroid, which indicates good in vivo stability of the compound. The extremely low uptake values in control tissues like muscle support its exceptional specificity of binding.

The obtained tumor-to-tissue ratios are in agreement with the ratios obtained through ex vivo biodistribution measurements (see example 4).

TABLE 8

Uptake values of [131I]SGMIB-labeled anti-HER2 2Rs15d VHH in a selection of organs and tissues, expressed as % injected activity (% IA)/cc. Each data point presents an average (n = 4).

| Organ/Tissue | 1 h | | 4 h | | 24 h | |
| --- | --- | --- | --- | --- | --- | --- |
| | MEAN | SD | MEAN | SD | MEAN | SD |
| Kidney | 9.64 | 0.74 | 2.33 | 0.28 | 0.22 | 0.06 |
| Bladder | 32.92 | 12.16 | 12.77 | 15.48 | 0.48 | 0.72 |
| Thyroid | 0.01 | 0.002 | 0.01 | 0.005 | 0.01 | 0.01 |
| Muscle | 0.004 | 0.001 | 0.002 | 0.001 | 0.001 | 0.0003 |
| Tumor | 2.07 | 3.45 | 1.82 | 3.04 | 1.07 | 1.30 |

TABLE 9

Calculated tumor-to-tissue ratios of [$^{131}$I]SGMIB-labeled anti-HER2 2Rs15d VHH from values described in Table 8. Each data point presents an average (n = 4).

| Tumor/tissue ratio | 1 h | | 4 h | | 24 h | |
| --- | --- | --- | --- | --- | --- | --- |
| | MEAN | SD | MEAN | SD | MEAN | SD |
| Kidney | 0.23 | 0.38 | 0.81 | 1.36 | 5.58 | 6.47 |
| Bladder | 0.07 | 0.11 | 0.25 | 0.31 | 13.37 | 17.64 |
| Thyroid | 278.95 | 440.78 | 120.08 | 168.04 | 78.31 | 78.72 |
| Muscle | 615.96 | 1073.44 | 925.98 | 1164.10 | 1669.89 | 2061.07 |

In conclusion, the [$^{131}$I]SGMIB-labeled anti-HER2 2Rs15d VHH can be used for both imaging and therapy in one and the same format.

What is claimed is:

1. A method of treating a HER2-expressing cancer, the method comprising:
   (a) selecting a subject having cancer for treatment on the basis of detection in the subject of a screening dose of a radiolabelled, heavy chain variable domain derived from a heavy chain antibody ($V_{HH}$), or a functional fragment thereof, which specifically binds to HER2 that is present on a cancer cell or solid tumor
   wherein the $V_{HH}$ or functional fragment thereof comprises a CDR1 comprising the amino acid sequence of SEQ ID NO:1,
   a CDR2 comprising the amino acid sequence of SEQ ID NO:2, and
   a CDR3 comprising the amino acid sequence of SEQ ID NO:3; and
   (b) administering to the subject a therapeutic dose of the radiolabelled $V_{HH}$, or functional fragment thereof, wherein the $V_{HH}$, or functional fragment thereof, of both the screening dose and the therapeutic dose is radiolabelled with Iodine-131 using N-succinimidyl-4-guanidinomethyl-3-[I-131] iodobenzoate ([I-131]-SGMIB).

2. The method of claim 1, further comprising:
   administering the screening dose to the subject and detecting the presence of the radiolabelled $V_{HH}$, or functional fragment thereof, at a tumor site in the subject prior to selecting the subject.

3. The method of claim 2, wherein detecting the presence of the radiolabelled $V_{HH}$, or functional fragment thereof, comprises imaging the subject.

4. The method of claim 3, wherein the imaging is gamma camera imaging.

5. The method of claim 1, wherein the screening dose is between about 37 MBq and about 370 MBq and the therapeutic dose is between about 370 MBq and about 18500 MBq.

6. The method of claim 1, wherein the radiolabelled $V_{HH}$, or the functional fragment thereof, has at least 80% amino acid identity with the amino acid sequences of SEQ ID NO:7.

7. The method of claim 1, wherein the radiolabelled $V_{HH}$, or functional fragment thereof, is present in a monovalent format.

8. The method of claim 1, wherein the radiolabelled $V_{HH}$, or functional fragment thereof, is devoid of a cysteine-containing tag.

9. The method of claim 1, wherein the cancer is a solid tumor or a hematological cancer.

10. The method of claim 9, wherein the HER2-expressing cancer is a HER2-expressing solid cancer.

11. The method of claim 10, wherein the HER2-expressing solid cancer is selected from the group consisting of breast cancer, ovarian cancer and gastric cancer.

12. The method of claim 9, wherein the HER2-expressing cancer is a HER2-expressing hematological cancer.

13. The method of claim 10, wherein the HER2-expressing cancer is a HER2-positive breast cancer.

14. The method of claim 13, wherein the HER2-positive breast cancer is locally advanced or metastatic.

15. The method of claim 14, wherein the HER2-positive breast cancer is metastatic and present in the brain of the subject.

16. The method of claim 10, wherein the HER2-expressing cancer is gastric cancer.

17. The method of claim 16, wherein the gastric cancer is locally advanced or metastatic.

18. The method of claim 17, wherein the gastric cancer is metastatic and present in the brain of the subject.

19. The method of claim 4, wherein the gamma camera imaging is selected from the group consisting of one or any combination of planar gamma camera imaging, single photon emission computed tomography and positron emission tomography.

20. The method of claim 4, wherein the imaging is selected from the group consisting of one or any combination of X-ray imaging, computed tomography and magnetic resonance imaging.

21. The method of claim 8, wherein the radiolabelled $V_{HH}$, or functional fragment thereof, is devoid of a GGC-tag.

22. The method of claim 8, wherein the radiolabeled $V_{HH}$, or functional fragment thereof, is untagged.

23. The method of claim 1, wherein the therapeutic dose is between about 3000 MBq and about 20000 MBq, between about 10000 MBq and about 20000 MBq, or between about 3000 MBq and about 10000 MBq.

24. The method of claim 1, wherein the radiolabelled $V_{HH}$ comprises the amino acid sequence of SEQ ID NO: 7.

25. A method of treating a HER2-expressing cancer, the method comprising:
  (a) selecting a subject having breast cancer for treatment on the basis of detection in the subject of a screening dose of between about 37 MBq and about 370 MBq of a radiolabelled, heavy chain variable domain derived from a heavy chain antibody ($V_{HH}$), or a functional fragment thereof, which specifically binds to HER2 that is present on the cancer
  wherein the $V_{HH}$ or functional fragment thereof comprises a CDR1 comprising the amino acid sequence of SEQ ID NO:1,
  a CDR2 comprising the amino acid sequence of SEQ ID NO:2, and
  a CDR3 comprising the amino acid sequence of SEQ ID NO:3; and
  (b) administering to the subject a therapeutic dose of between about 3000 MBq and about 20000 MBq of the radiolabelled $V_{HH}$, or functional fragment thereof,
  wherein the radiolabelled $V_{HH}$, or functional fragment thereof, of both the screening dose and the therapeutic dose comprises N-succinimidyl-4-guanidinomethyl-3-[I-131]iodobenzoate ([I-131]-SGMIB).

26. The method of claim 25, wherein the HER2-expressing cancer is a solid tumor.

27. The method of claim 25, wherein HER2 expression is detected in the cancer.

28. The method of claim 27, wherein HER2 expression is detected in the cancer by in situ hybridization or by immunohistochemistry.

29. The method of claim 25, wherein the $V_{HH}$ comprises the amino acid sequence of SEQ ID NO: 7.

30. A method of treating a HER2-expressing breast cancer, the method comprising:
  (a) selecting a subject having breast cancer for treatment on the basis of detection in the subject of a screening dose of between about 37 MBq and about 370 MBq of a radiolabelled, heavy chain variable domain derived from a heavy chain antibody ($V_{HH}$), or a functional fragment thereof, which specifically binds to HER2 that is present on the breast cancer;
  wherein the $V_{HH}$ or functional fragment thereof comprises a CDR1 comprising the amino acid sequence of SEQ ID NO:1,
  a CDR2 comprising the amino acid sequence of SEQ ID NO:2, and
  a CDR3 comprising the amino acid sequence of SEQ ID NO:3; and
  (b) administering to the subject a therapeutic dose of between about 3000 MBq and about 20000 MBq of the radiolabelled $V_{HH}$, or functional fragment thereof,
  wherein the radiolabelled $V_{HH}$, or functional fragment thereof, of both the screening dose and the therapeutic dose comprises N-succinimidyl-4-guanidinomethyl-3 [I-131]iodobenzoate ([I-131]-SGMIB).

31. The method of claim 30, wherein the $V_{HH}$ comprises the amino acid sequence of SEQ ID NO: 7.

32. A method of treating a HER2-expressing gastric cancer, the method comprising:
  (a) selecting a subject having gastric cancer for treatment on the basis of detection in the subject of a screening dose of between about 37 MBq and about 370 MBq of a radiolabelled, heavy chain variable domain derived from a heavy chain antibody ($V_{HH}$), or a functional fragment thereof, which specifically binds to HER2 that is present on the gastric cancer
  wherein the $V_{HH}$ or functional fragment thereof comprises a CDR1 comprising the amino acid sequence of SEQ ID NO:1,
  a CDR2 comprising the amino acid sequence of SEQ ID NO:2, and
  a CDR3 comprising the amino acid sequence of SEQ ID NO:3; and
  (b) administering to the subject a therapeutic dose of between about 3000 MBq and about 20000 MBq of the radiolabelled $V_{HH}$, or functional fragment thereof,
  wherein the radiolabelled $V_{HH}$, or functional fragment thereof, of both the screening dose and the therapeutic dose comprises N-succinimidyl-4-guanidinomethyl-3-[I-131]iodobenzoate ([I-131]-SGMIB).

33. The method of claim 32, wherein the $V_{HH}$ comprises the amino acid sequence of SEQ ID NO: 7.

* * * * *

SEQUENCE LISTING

```
<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: CDR1 sequence of VHH 2Rs15d

<400> SEQUENCE: 1

Gly Tyr Ile Phe Asn Ser Cys Gly
1               5

<210> SEQ ID NO 2
<211> LENGTH: 7
<212> TYPE: PRT
<213> ORGANISM: Artificial Sequence
<220> FEATURE:
<223> OTHER INFORMATION: CDR2 sequence of VHH 2Rs15d

<400> SEQUENCE: 2

Ile Ser Gly Asp Gly Asp Thr
1               5

<210> SEQ ID NO 3
<211> LENGTH: 9
<212> TYPE: PRT
<213> ORGANISM: Artificial Sequence
<220> FEATURE:
<223> OTHER INFORMATION: CDR3 sequence of VHH 2Rs15d

<400> SEQUENCE: 3

Ala Val Cys Tyr Asn Leu Glu Thr Tyr
1               5

<210> SEQ ID NO 4
<211> LENGTH: 8
<212> TYPE: PRT
<213> ORGANISM: Artificial Sequence
<220> FEATURE:
<223> OTHER INFORMATION: CDR1 sequence of VHH 2Rb17c

<400> SEQUENCE: 4

Gly Phe Ile Phe Ser Asn Asp Ala
1               5
```

```
<210> SEQ ID NO 5
<211> LENGTH: 8
<212> TYPE: PRT
<213> ORGANISM: Artificial Sequence
<220> FEATURE:
<223> OTHER INFORMATION: CDR2 sequence of VHH 2Rb17c

<400> SEQUENCE: 5

Ile Asn Trp Ser Gly Thr His Thr
1               5

<210> SEQ ID NO 6
<211> LENGTH: 10
<212> TYPE: PRT
<213> ORGANISM: Artificial Sequence
<220> FEATURE:
<223> OTHER INFORMATION: CDR3 sequence of VHH 2Rb17c

<400> SEQUENCE: 6

Val Thr Gly Tyr Gly Val Thr Lys Thr Pro
1               5                   10

<210> SEQ ID NO 7
<211> LENGTH: 115
<212> TYPE: PRT
<213> ORGANISM: Artificial Sequence
<220> FEATURE:
<223> OTHER INFORMATION: VHH sequence 2Rs15d

<400> SEQUENCE: 7

Gln Val Gln Leu Gln Glu Ser Gly Gly Gly Ser Val Gln Ala Gly Gly
1               5                   10                  15

Ser Leu Lys Leu Thr Cys Ala Ala Ser Gly Tyr Ile Phe Asn Ser Cys
            20                  25                  30

Gly Met Gly Trp Tyr Arg Gln Ser Pro Gly Arg Glu Arg Glu Leu Val
        35                  40                  45

Ser Arg Ile Ser Gly Asp Gly Asp Thr Trp His Lys Glu Ser Val Lys
    50                  55                  60

Gly Arg Phe Thr Ile Ser Gln Asp Asn Val Lys Lys Thr Leu Tyr Leu
65                  70                  75                  80

Gln Met Asn Ser Leu Lys Pro Glu Asp Thr Ala Val Tyr Phe Cys Ala
                85                  90                  95

Val Cys Tyr Asn Leu Glu Thr Tyr Trp Gly Gln Gly Thr Gln Val Thr
            100                 105                 110

Val Ser Ser
        115

<210> SEQ ID NO 8
<211> LENGTH: 117
<212> TYPE: PRT
<213> ORGANISM: Artificial Sequence
<220> FEATURE:
<223> OTHER INFORMATION: VHH sequence 2Rb17c

<400> SEQUENCE: 8

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ile Phe Ser Asn Asp
            20                  25                  30

Ala Met Thr Trp Val Arg Gln Ala Pro Gly Lys Gly Leu Glu Trp Val
        35                  40                  45
```

```
Ser Ser Ile Asn Trp Ser Gly Thr His Thr Asn Tyr Ala Asp Ser Val
    50                  55                  60

Lys Gly Arg Phe Thr Ile Ser Arg Asp Asn Ala Lys Arg Thr Leu Tyr
65              70                  75                  80

Leu Gln Met Asn Ser Leu Lys Asp Glu Asp Thr Ala Leu Tyr Tyr Cys
                85                  90                  95

Val Thr Gly Tyr Gly Val Thr Lys Thr Pro Thr Gly Gln Gly Thr Gln
            100                 105                 110

Val Thr Val Ser Ser
            115

<210> SEQ ID NO 9
<211> LENGTH: 6
<212> TYPE: PRT
<213> ORGANISM: Artificial Sequence
<220> FEATURE:
<223> OTHER INFORMATION: His-tag

<400> SEQUENCE: 9

His His His His His His
1               5

<210> SEQ ID NO 10
<211> LENGTH: 23
<212> TYPE: PRT
<213> ORGANISM: Artificial Sequence
<220> FEATURE:
<223> OTHER INFORMATION: Myc-His-tag

<400> SEQUENCE: 10

Ala Ala Ala Glu Gln Lys Leu Ile Ser Glu Glu Asp Leu Asn Gly Ala
1               5                   10                  15

Ala His His His His His His
            20
```